US012760337B2

(12) United States Patent
Zhao et al.

(10) Patent No.: US 12,760,337 B2
(45) Date of Patent: Oct. 13, 2026

(54) SUCCINIC ACID PRODUCTION USING *ISSATCHENKIA*

(71) Applicant: The Board of Trustees of the University of Illinois, Urbana, IL (US)

(72) Inventors: Huimin Zhao, Champaign, IL (US); Vinh Tran, Urbana, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 677 days.

(21) Appl. No.: 18/302,290

(22) Filed: Apr. 18, 2023

(65) Prior Publication Data

US 2023/0365998 A1 Nov. 16, 2023

Related U.S. Application Data

(60) Provisional application No. 63/332,267, filed on Apr. 18, 2022.

(51) Int. Cl.

| | |
|---|---|
| ***C12P 7/46*** | (2006.01) |
| ***C12N 9/00*** | (2006.01) |
| ***C12N 9/02*** | (2006.01) |
| ***C12N 9/04*** | (2006.01) |
| ***C12N 9/26*** | (2006.01) |
| ***C12N 9/88*** | (2006.01) |
| ***C12N 15/52*** | (2006.01) |
| ***C12N 15/81*** | (2006.01) |

(52) U.S. Cl.

CPC .............. *C12P 7/46* (2013.01); *C12N 9/0006* (2013.01); *C12N 9/001* (2013.01); *C12N 9/2431* (2013.01); *C12N 9/88* (2013.01); *C12N 9/93* (2013.01); *C12N 15/52* (2013.01); *C12N 15/815* (2013.01); *C12Y 101/01029* (2013.01); *C12Y 101/01037* (2013.01); *C12Y 103/01006* (2013.01); *C12Y 302/01026* (2013.01); *C12Y 402/01002* (2013.01); *C12Y 604/01001* (2013.01); *C12N 2800/102* (2013.01)

(58) Field of Classification Search

None

See application file for complete search history.

(56) References Cited

U.S. PATENT DOCUMENTS

| | | | | |
|---|---|---|---|---|
| 9,689,006 | B2 | 6/2017 | Burk et al. | |
| 10,287,611 | B2 | 5/2019 | Zhang et al. | |
| 11,041,176 | B2 * | 6/2021 | Rush | C12P 7/42 |
| 11,072,807 | B2 | 7/2021 | Yocum et al. | |
| 11,085,015 | B2 | 8/2021 | Pharkya et al. | |
| 2012/0040422 | A1 | 2/2012 | Jansen et al. | |
| 2012/0225461 | A1 | 9/2012 | Dole et al. | |
| 2014/0363862 | A1 * | 12/2014 | Rush | C12N 15/52 435/145 |
| 2018/0142269 | A1 | 5/2018 | Burk et al. | |
| 2021/0348175 | A1 | 11/2021 | Zhao et al. | |

FOREIGN PATENT DOCUMENTS

| | | | | |
|---|---|---|---|---|
| WO | WO 2007/030830 A2 | | 3/2007 | |
| WO | WO-2014018757 A1 | * | 1/2014 | C12N 9/0006 |
| WO | WO-2017091610 A1 | * | 6/2017 | C12Y 302/01026 |

OTHER PUBLICATIONS

Boles et al., Identification and Characterization of MAE1, the *Saccharomyces cerevisiae* Structural Gene Encoding Mitochondrial Malic Enzyme, J. Bacteriol. 180, 1988, 2875-82. (Year: 1988).*

Uniprot, Accession No. P50537, 2021, www.uniprot.org. (Year: 2021).*

Tran et al., An end-to-end pipeline for succinic acid production at an industrially relevant scale using Issatchenkia orientalis, Nature Comm. 14, 2023, 6152. (Year: 2023).*

Uniprot, Accession No. Q6BC32, 2020, www.uniprot.org. (Year: 2020).*

Shen et al., Economical Succinic Acid Production from Sugarcane Juice by Actinobacillus succinogenes Supplemented with Corn Steep, Sugar Tech 18, 2016, 292-98. (Year: 2016).*

Kawai et al., Identification of metabolic engineering targets for improving glycerol assimilation ability of *Saccharomyces cerevisiae* based on adaptive laboratory evolution and transcriptome analysis, J. Biosci. Bioeng. 2, 2019, 162-69. (Year: 2019).*

Xiberras et al., Engineering *Saccharomyces cerevisiae* for Succinic Acid Production From Glycerol and Carbon Dioxide, Frontiers Bioeng. Biotechnol. 8, 2020, 566. (Year: 2020).*

Costas et al., Lipolytic activity in submerged cultures of Issatchenkia orientalis, Process Biochem. 39, 2004, 2109-14. (Year: 2004).*

Suthers et al., Examining organic acid production potential and growth coupled strategies in Issatchenkia orientalis using constraint-based modeling, Biotechnol. Progress, 2022, e3276. (Year: 2022).*

Ahn et al., "Enhanced succinic acid production by Mannheimia employing optimal malate dehydrogenase", Nat. Commun., 2020, 11(1), 1970.

Ahn et al., "Production of succinic acid by metabolically engineered microorganisms", Curr. Opin, Biotechnol., Mar. 15, 2016, 42: 54-66.

Alexandri et al., "Downstream separation and purification of succinic acid from fermentation broths using spent sulfite liquor as feedstock", Sep. Purif. Technol., Jan. 31, 2019, 209: 666-675.

Argonne National Laboratory, Apr. 30, 2022. GREET 2022 Model. Retrieved online from: https://greet.es.anl.gov/.

Bhagwat et al., "Sustainable Production of Acrylic Acid via 3-Hydroxypropionic Acid from Lignocellulosic Biomass", ACS Sustainable Chem., Nov. 29, 2021, 9(49):16659-16669.

BioSTEAM Development Group. Bioindustrial-Park: BioSTEAM's Premier Repository for Biorefinery Models and Results [WWW Document], 2023. Retrieved online from: github.com/yoelcortes/Bioindustrial-Park.

(Continued)

*Primary Examiner* — Todd M Epstein

(74) *Attorney, Agent, or Firm* — Lathrop GPM LLP; Lisa Hillman

(57) ABSTRACT

Provided herein are genetically modified *Issatchenkia* yeast and fermentation methods for producing succinic acid.

22 Claims, 16 Drawing Sheets

Specification includes a Sequence Listing.

(56) References Cited

OTHER PUBLICATIONS

Cao et al., "A genetic toolbox for metabolic engineering of Issatchenkia orientalis", Metab. Eng., May 2020, 59: 87-97.
Chen et al., "Toward glycerol biorefinery: metabolic engineering for the production of biofuels and chemicals from glycerol", Biotechnol. Biofuels, Oct. 3, 2016, 9: 205. eCollection 2016.
Claypool et al., "Development and validation of a technoeconomic analysis tool for early-stage evaluation of bio-based chemical production processes", Bioresource Technology, Dec. 2013, 150: 486-495.
Cok et al., "Succinic acid production derived from carbohydrates: An energy and greenhouse gas assessment of a platform chemical toward a bio-based economy", Biofuels, Bioprod. Bioref., Jan./Feb. 2014, 8(1): 16-29.
Cordova et al., "Direct production of fatty alcohols from glucose using engineered strains of Yarrowia lipolytica", Metab. Eng. Commun., Oct. 31, 2019, 10: e00105. eCollection Jun. 2020.
Cortes-Pena et al., "BioSTEAM: A Fast and Flexible Platform for the Design, Simulation, and Techno-Economic Analysis of Biorefineries under Uncertainty", ACS Sustain. Chem. & Eng., Jan. 30, 2020, 8(8) 3302-3310.
Cui et al., "Engineering of unconventional yeast Yarrowia lipolytica for efficient succinic acid production from glycerol at low pH", Metab. Eng., Jul. 2017, 42: 126-133.
Dai et al., "Bio-based succinic acid: an overview of strain development, substrate utilization, and downstream purification", Biofuels, Bioprod. Biorefin., Sep./Oct. 2020, 14(5): 965-985.
Darbani et al., "Engineering Energetically Efficient Transport of Dicarboxylic Acids in Yeast *Saccharomyces cerevisiae*", PNAS USA, Sep. 24, 2019, 116(39): 19415-19420.
Dickson et al., "Sustainable bio-succinic acid production: superstructure optimization, techno-economic, and lifecycle assessment", Energy Environ. Sci., Apr. 23, 2021, 14(6): 3542-3558.
Dogbe et al., "Revitalizing the sugarcane industry by adding value to A-molasses in biorefineries", Biofuels, Bioprod, Bioref., Sep./Oct. 2020, 14(5): 1089-1104.
Douglass et al., "Population genomics shows no distinction between pathogenic Candida krusei and environmental Pichia kudriavzevii: One species, four names", PLoS Pathog, Jul. 2018, 14(7): e1007138. Published online Jul. 29, 2018.
Du et al., "Engineering microbial factories for synthesis of value-added products", J. Ind. Microbiol. Biotechnol., Aug. 2011, 38(8): 873-890.
Dunn et al., "Life-cycle Analysis of Bioproducts and Their Conventional Counterparts in GREET (No. ANL/ESD-14/9 Rev.)", Argonne National Lab. (ANL), Argonne, IL (United States), Sep. 1, 2015. Retrieved online at: https://doi.org/10.2172/1250468.
E4tech, Re-Cord and Wageningen UR, "From the Sugar Platform to biofuels and biochemicals : Final report for the European Commission Directorate-General Energy", Contract No. ENER/C2/423-2012/SI2.673791, Apr. 2015, Version 2.1.
Efe et al., "Techno-economic analysis of succinic acid production using adsorption from fermentation medium", Biomass and Bioenerg., Sep. 2013, 56: 479-492.
Engler et al., "A one pot, one step, precision cloning method with high throughput capability", PloS one, 2008, 3(11): e3647. Epub Nov. 5, 2008.
Gibson et al., "Enzymatic assembly of DNA molecules up to several hundred kilobases", Nat. Methods, May 2009, 6(5): 343-345. Epub Apr. 12, 2009.
Gietz et al., "Studies on the transformation of intact yeast cells by the LiAc/SS-DNA/PEG procedure", Yeast, Apr. 15, 1995, 11(4): 355-360.
Gupta et al., "Economic assessment of continuous processing for manufacturing of biotherapeutics", Biotechnology Progress, Dec. 10, 2020, 37(2): e3108.
Ioannidou et al., "Techno-economic evaluation and life cycle assessment of a biorefinery using winery waste streams for the production of succinic acid and value-added co-products", Bioresour. Technol., Mar. 2022, 348: 126295.
Isono, "A comparative study of ethanol production by Issatchenkia orientalis strains under stress conditions", J. Biosci. Bioeng, Jan. 2012, 113(1): 76-78.
Jansen et al., "Towards large scale fermentative production of succinic acid", Curr. Opin. Biotechnol., Dec. 2014, 30: 190-197.
Jiang et al., "Engineering of Yarrowia lipolytica transporters for high-efficient production of biobased succinic acid from glucose", Biotechnol. Biofuels, Jun. 27, 2021, 14(1): 145.
Jokodola et al., "Process optimization for production and recovery of succinic acid using xylose-rich hydrolysates by Actinobacillus succinogenes", Bioresour. Technol., Jan. 2022, 344(Part B): 126224. Epub Oct. 28, 2021.
Karp et al., "Post-Fermentation Recovery of Biobased Carboxylic Acids", ACS Sustain. Chem. & Eng., Oct. 16, 2018, 6(11): 15273-15283.
Klein et al. "Process development and techno-economic analysis of bio-based succinic acid derived from pentoses integrated to a sugarcane biorefinery", Biofuels, Bioprod. Bioref., Nov./Dec. 2017, 11(6): 1051-1064.
Klein et al., "Towards the exploitation of glycerol's high reducing power in *Saccharomyces cerevisiae*-based bioprocesses", Metab. Eng., Nov. 2016, 38: 464-472. Epub Oct. 14, 2016.
Kumar et al., "Sustainable production and purification of succinic acid: A review of membrane-integrated green approach", J. Clean. Prod., Dec. 20, 2020, 277: 123954.
Ladakis et al., "Biorefinery development, techno-economic evaluation and environmental impact analysis for the conversion of the organic fraction of municipal solid waste into succinic acid and value-added fractions", Bioresour. Technol., Jun. 2022, 354: 127172. Epub Apr. 18, 2022.
Lane et al, "Glucose repression can be alleviated by reducing phosphorylation rate in *Saccharomyces cerevisiae*", Sci. Rep., Feb. 8, 2018, 8(10): 2613.
Li et al, "Recovery processes of organic acids from fermentation broths in the biomass-based industry", J. Microbiol. Biotechnol., Jan. 2016, 26(1): 1-8.
Li et al., "Efficient metabolic evolution of engineered Yarrowia lipolytica for succinic acid production using a glucose-based medium in an in situ fibrous bioreactor under low-pH condition", Biotechnol. Biofuels, Aug. 30, 2018, 11: 236. eCollection 2018.
Li et al., "Green and sustainable succinic acid production from crude glycerol by engineered Yarrowia lipolytica via agricultural residue-based in situ fibrous bed bioreactor", Bioresour. Technol, Feb. 2018, 249: 612-619. Epub Oct. 12, 2017.
Li et al., "One step recovery of succinic acid from fermentation broths by crystallization", Sep. Purif. Technol., May 11, 2010, 72(3): 294-300.
Lian et al., "Recent advances in metabolic engineering of *Saccharomyces cerevisiae*: new tools and their applications", Metab. Eng., Nov. 2018, 50: 85-108. Epub Apr. 25, 2018.
Lin et al., "Novel resin-based vacuum distillation-crystallization method for recovery of succinic acid crystals from fermentation broths", Green Chem., Feb. 20, 2010, 12(4): 666-667.
Litsanov et al., "Toward homosuccinate fermentation: metabolic engineering of Corynebacterium glutamicum for anaerobic production of succinate from glucose and formate", Appl. Environ. Microbiol., May 2012, 78(9): 3325-3337.
Liu et al., "Glycerol/glucose co-fermentation: one more proficient process to produce propionic acid by Propionibacterium acidipropionici", Curr. Microbiol., Jan. 2011, 62(1): 152-158. Epub Jun. 11, 2010.
Luthfi et al., "Multiple crystallization as a potential strategy for efficient recovery of succinic acid following fermentation with immobilized cells", Bioprocess Biosyst. Eng., Jul. 2020, 43(7): 1153-1169.
Okino et al., "An efficient succinic acid production process in a metabolically engineered Corynebacterium glutamicum strain", Appl. Microbiol. Biotechnol., Dec. 2008, 81(3): 459-464.

(56) References Cited

OTHER PUBLICATIONS

Padi et al., "Feasibility of commercial waste biorefineries for cassava starch industries: Techno-economic assessment", Bioresource Technology, Feb. 2020, 297: 122461.
Park et al., "Low-pH production of d-lactic acid using newly isolated acid tolerant yeast Pichia kudriavzevii NG7", Biotechnol. Bioeng., Sep. 2018, 115(9): 2232-2242. Epub Jul. 6, 2018.
Shaji et al., "Economic and Environmental Assessment of Succinic Acid Production from Sugarcane Bagasse", ACS Sustain, Chem. & Eng., Sep. 15, 2021, 9(38): 12738-12746.
Shao et al., "DNA assembler, an in vivo genetic method for rapid construction of biochemical pathways", Nucleic Acids Res., Feb. 2009, 37(2): e16. Epub Dec. 12, 2008.
Skorokhodova et al., "Manipulating pyruvate to acetyl-CoA conversion in *Escherichia coli* for anaerobic succinate biosynthesis from glucose with the yield close to the stoichiometric maximum", J. Biotechnol., Nov. 20, 2015, 214: 33-42. Epub Sep. 8, 2015.
Stylianou et al., "Bioprocess development using organic biowaste and sustainability assessment of succinic acid production with engineered Yarrowia lipolytica strain", Biochem. Eng. J., Oct. 2021, 174: 108099.
Suthers et al., "Genome-scale metabolic reconstruction of the non-model yeast Issatchenkia orientalis SD108 and its application to organic acids production", Metab. Eng. Commun., Oct. 8, 2020, 11: e00148. eCollection Dec. 2020.
Tran et al., "Development of a CRISPR/Cas9-Based Tool for Gene Deletion in Issatchenkia orientalis", mSphere, Jun. 26, 2019, 4(3): e00345-19.
Tran et al., "Engineering robust microorganisms for organic acid production". J. Ind. Microbiol. Biotechnol., Apr. 14. 2022, 49(2): kuab067.
Volk et al., "Metabolic Engineering: Methodologies and Applications", Chemical Reviews, May 10, 2023, 123(9): 5521-5570. Epub Dec. 30, 2022.
Wang et al. "High cell density fermentation via a metabolically engineered *Escherichia coli* for the enhanced production of succinic acid", J. Chem. Technol. Biotechnol., Apr. 2011, 86(4): 512-518.
Wang et al., "A novel riboregulator switch system of gene expression for enhanced microbial production of succinic acid", J. Ind. Microb. Biotechnol., Apr. 2018, 45(4): 253-269. Epub Feb. 5, 2018.
Wang et al., "Peak annotation and verification engine for untargeted LC-MS metabolomics", Anal. Chem., Feb. 5, 2019, 91(3): 1838-1846. Epub Jan. 10, 2019.
Xi et al., "Characterization of JEN family carboxylate transporters from the acid-tolerant yeast Pichia kudriavzevii and their applications in succinic acid production", Microb. Biotechnol., May 2021, 14(3): 1130-1147. Epub Feb. 25, 2021.
Xiao et al., "Exploiting Issatchenkia orientalis SD108 for succinic acid production", Microb. Cell Factories, Aug. 27, 2014, 13: 121.
Xun et al., "The stepwise endonuclease activity of a thermophilic Argonaute protein", bioRxiv, Oct. 29, 2019, 821280.
Yan et al., "Construction of reductive pathway in *Saccharomyces cerevisiae* for effective succinic acid fermentation at low pH value", Bioresour. Technol., Mar. 2014, 156: 232-239. Epub Jan. 24, 2014.
Young, "INCA: a computational platform for isotopically non-stationary metabolic flux analysis", Bioinformatics, May 1, 2014, 30(9): 1333-1335. Epub Jan. 11, 2014.
Zale et al., "Metabolic engineering of sugarcane to accumulate energy-dense triacylglycerols in vegetative biomass", Plant Biotechnol. J., Feb. 2016, 14(2): 661-669. Epub Jun. 8, 2015.
Zhang et al., "n-Butanol production from sucrose and sugarcane juice by engineered Clostridium tyrobutyricum overexpressing sucrose catabolismgenes and adhE2", Bioresour. Technol., Jun. 2017, 233: 51-57. Epub Feb. 21, 2017.

* cited by examiner

| Genetic modifications | | | | | | | | |
|---|---|---|---|---|---|---|---|---|
| *PYC, MDH, FUMR, FRD* | + | + | + | + | + | + | + | + |
| *SpMAE1* | + | + | + | + | + | + | + | + |
| *pdcΔ, gpdΔ* | - | - | + | + | + | + | + | + |
| g3473Δ | - | - | - | - | - | + | + | + |
| *ndeΔ* | - | - | - | - | - | - | + | - |
| *PaGDH, DAK* | - | - | - | - | - | - | - | + |
| **Substrate** | | | | | | | | |
| glucose | + | + | + | + | + | + | + | + |
| glycerol | - | - | - | + | + | + | + | + |
| **Aeration** | | | | | | | | |
| oxygen-limited | + | + | + | - | - | - | - | - |
| aerobic | - | - | - | + | + | + | + | + |

A

B

SUCCINIC ACID PRODUCTION USING *ISSATCHENKIA*

PRIORITY

This application claims the benefit of U.S. Ser. No. 63/332,267, which was filed Apr. 18, 2022, and which is incorporated by reference herein in its entirety.

STATEMENT REGARDING FEDERALLY SPONSORED RESEARCH OR DEVELOPMENT

This invention was made with government support under contract numbers DE-SC0018420 awarded by the Department of Energy. The government has certain rights in the invention.

SEQUENCE LISTING

This document incorporates by reference herein an electronic sequence listing text file, which is filed in electronic format via EFS-Web. The text file is named 741074_SL.xml is 76,000 bytes, and was created on Jul. 18, 2023.

BACKGROUND

To reduce the global reliance on fossil fuels, microbial conversion of renewable biomass into everyday products is being developed as a sustainable alternative to the conventional petroleum-based production processes. The US Department of Energy described succinic acid (SA) as one of the top 12 bio-based building blocks that can be produced using microorganisms. It is an industrially important platform chemical with diverse applications in food, pharmaceutical, and agriculture industries. SA is also used as a precursor to produce high-value chemicals, such as 1,4-butanediol and tetrahydrofuran, and as a monomer for the synthesis of biodegradable polymers, such as polybutylene succinate.

Metabolically engineered bacterial species such as *Escherichia coli, Corynebacterium glutamicum*, and *Mannheimia succiniciproducens* can produce SA with impressive performance. Nevertheless, because of the toxicity exerted by low pH conditions on bacterial growth, utilization of neutralizing agents, such as lime ($CaCO_3$) or base (NaOH), is necessary to maintain neutral pH environment. After fermentation, strong acids, such as $H_2SO_4$, are used for reacidification, converting succinate, the salt form, into SA, the undissociated form (FIG. 16A). As a result, the conventional downstream processing (DSP) steps generate a considerable amount of gypsum ($CaSO_4$), which needs proper disposal and has environmental concerns. Producing SA in low pH fermentation would be an economical solution to lower operating costs and environmental footprint.

SUMMARY

Provided herein are recombinant yeast, e.g., Issatchenkia. The recombinant yeast can comprise: heterologous polynucleotides encoding pyruvate carboxylase (PYC), malate dehydrogenase (MDH), fumarase (FUMR) and fumarate reductase (FDR); a heterologous polynucleotide encoding dicarboxylic acid transporter (MAE1); a deleted or non-functional pyruvate decarboxylase (PDC) gene; a deleted or non-functional glycerol 3-phosphate dehydrogenase (GPD) gene. The recombinant yeast can further comprise a deleted or non-functional JEN carboxylate transporter gene. The recombinant yeast can further comprise a deleted or non-functional NADH dehydrogenase (NDE) gene. The recombinant yeast can further comprise a heterologous polynucleotide encoding glycerol dehydrogenase (GDH). The heterologous polynucleotide encoding glycerol dehydrogenase (GDH) can be overexpressed. The recombinant yeast can further comprise an over expressed dihydroxyacetone kinase gene (DAK). The recombinant yeast can further comprise a deleted or non-functional g3837 hexokinase gene. The recombinant yeast can further comprise a heterologous polynucleotide encoding invertase (SUC2). The polynucleotide encoding pyruvate carboxylase (PYC), malate dehydrogenase (MDH), fumarase (FUMR) and fumarate reductase (FDR) encode polypeptides as shown in SEQ ID NO:62, SEQ ID NO:63, SEQ ID NO:64, SEQ ID NO:65, respectively, or polypeptides comprising 85% or more sequence identity to SEQ ID NO: 62, SEQ ID NO:63, SEQ ID NO:64, or SEQ ID NO:65. The polynucleotide encoding dicarboxylic acid transporter (MAE1) can encode a polypeptide having 85% or more sequence e identity to SEQ ID NO:59. The polynucleotide encoding glycerol dehydrogenase (GDH) can encode a polypeptide having 85% or more sequence identity to SEQ ID NO:60. The polynucleotide encoding invertase (SUC2) can encode a polypeptide having 85% or more sequence identity to SEQ ID NO:61.

In an aspect a recombinant yeast, such as *Issatchenkia* yeast is provided. The recombinant yeast can comprise heterologous polynucleotides encoding pyruvate carboxylase (PYC), malate dehydrogenase (MDH), fumarase (FUMR) and fumarate reductase (FDR); a heterologous polynucleotide encoding dicarboxylic acid transporter (MAE1); a deleted or non-functional pyruvate decarboxylase (PCD) gene; a deleted or non-functional glycerol 3-phosphate dehydrogenase (GPD) gene; a deleted or non-functional JEN carboxylate transporter gene; a heterologous polynucleotide encoding glycerol dehydrogenase (GDH); an overexpressed dihydroxyacetone kinase (DAK) gene; and a deleted or non-functional g3837 hexokinase or a heterologous polynucleotide encoding invertase (SUC2).

An aspect provides a fermentation method for producing succinic acid comprising contacting a fermentation medium with any of the recombinant yeast e.g., Issatchenkia described herein; and fermenting the fermentation medium and the recombinant yeast wherein succinic acid is produced. The fermentation medium can comprise glucose and glycerol. The fermentation medium can comprise sugarcane juice, sugar beet feedstock, or sweet sorghum feedstock. The fermenting can be done via a fed-batch process, a batch process, or a continuous process. The pH of the fermentation medium can be about 2.0 to about 4.0. Succinic acid can be produced at more than 60 g/L. A yield of 0.40 g/g glucose equivalent or more can be achieved. A productivity of 0.40 g/L/h or more can be achieved. In an aspect, no acid is added to the fermentation medium during the fermenting. In an aspect, no neutralization agents are added to the fermentation medium to control pH.

DETAILED DESCRIPTION

Figure 16:
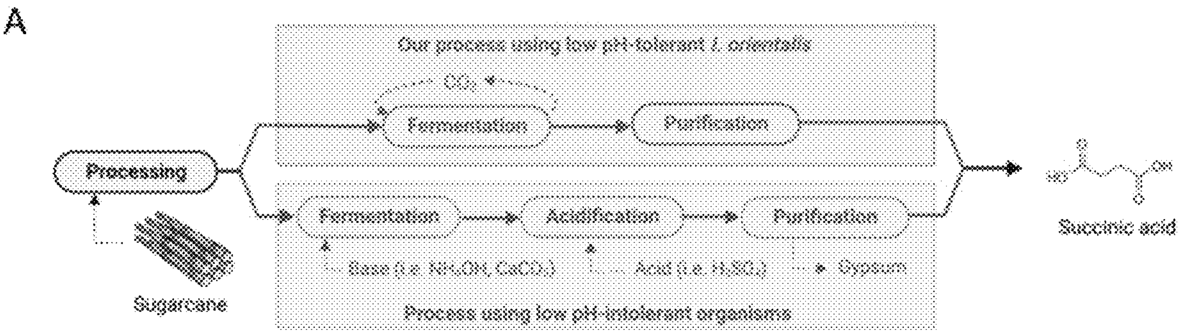
FIG. 16 shows panel A. engineered *I. orientalis* strain can produce succinic acid at low pH, eliminating the requirements of base and acidification and lowering the overall production cost. Panel B. A schematic diagram for succinic acid production by engineered *I. orientalis* strain.
Figure 16:
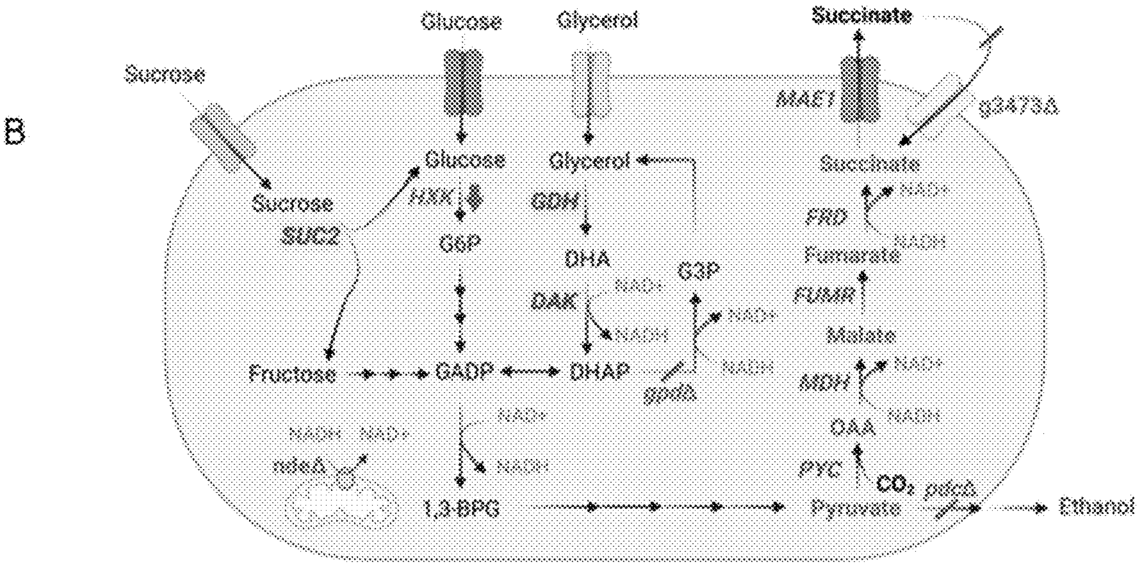

The non-conventional yeast *Issatchenkia orientalis* has superior tolerance to highly acidic conditions. Provided herein are new metabolic engineering strategies to improve the SA production in *I. orientalis* (FIG. 16B). Strains have been developed to produce SA at the highest titer ever reported in minimal media at low pH (pH 3) in bench-top reactors, i.e. titer of 109.5 g/L, yield of 0.59 g/g glucose equivalent, and productivity of 0.54 g/L/h using minimal medium containing glucose and glycerol and titer of 104.6 g/L, yield of 0.61 g/g glucose equivalent, and productivity of 1.25 g/L/h from sugarcane juice in fed-batch fermentation at pH 3. The fermentation process was scaled up to an industrial pilot scale with a scaling factor of 300× and achieved SA production at titer of 63.1 g/L, yield of 0.50 g/g glucose equivalent, and productivity of 0.66 g/L/h from sugarcane juice in batch fermentation at pH 3. Furthermore, biorefinery design, simulation, techno-economic analysis (TEA), and life cycle assessment (LCA) was performed under uncertainty to characterize the financial viability and environmental benefits of the developed SA production pathway. Sensitivity analyses were also performed to identify key drivers of production costs and environmental impacts for prioritization of future research, development, and deployment directions.

Recombinant Yeast

A recombinant, transgenic, or genetically engineered yeast is a yeast that has been genetically modified from its native state. Thus, a "recombinant yeast" or "recombinant yeast cell" refers to a yeast cell that has been genetically modified from the native state. A recombinant yeast cell can have, for example, nucleotide insertions, nucleotide deletions, nucleotide rearrangements, gene disruptions, recombinant polynucleotides, heterologous polynucleotides, deleted polynucleotides, nucleotide modifications, or combinations thereof introduced into its DNA. These genetic modifications can be present in the chromosome of the yeast cell, or on a plasmid in the yeast cell. Recombinant yeast cells disclosed herein can comprise exogenous polynucleotides on plasmids. Alternatively, recombinant cells can comprise exogenous polynucleotides stably incorporated into their chromosome.

A heterologous or exogenous polypeptide or polynucleotide refers to any polynucleotide or polypeptide that does not naturally occur or that is not present in the starting target yeast. For example, a polynucleotide from bacteria or yeast that is transformed into a yeast cell that does naturally or otherwise comprise the bacterial or yeast polynucleotide is a heterologous or exogenous polynucleotide. A heterologous or exogenous polypeptide or polynucleotide can be a wild-type, synthetic, or mutated polypeptide or polynucleotide. In an embodiment, a heterologous or exogenous polypeptide or polynucleotide is not naturally present in a starting target yeast and is from a different genus or species than the starting target microorganism.

A homologous or endogenous polypeptide or polynucleotide refers to any polynucleotide or polypeptide that naturally occurs or that is otherwise present in a starting target yeast. For example, a polynucleotide that is naturally present in a yeast cell is a homologous or endogenous polynucleotide. In an embodiment, a homologous or endogenous polypeptide or polynucleotide is naturally present in a starting target yeast.

A recombinant yeast can comprise one or more polynucleotides not present in a corresponding wild-type cell, wherein the polynucleotides have been introduced into that yeast using recombinant DNA techniques, or which polynucleotides are not present in a wild-type yeast and is the result of one or more mutations.

A genetically modified or recombinant yeast can be, for example, an Ascomycota or Basidiomycota. Examples include *Issatchenkia*, such as *Issatchenkia orientalis* or *I. hanoiensis* and all subspecies of *I. orientalis* and *I. hanoiensis*. Other examples include *Saccharomycesceae*, such as *Saccharomyces cerevisiae, Saccharomyces cerevisiae* strain S8, *Saccharomyces pastorianus, Saccharomyces beticus, Saccharomyces fermentati, Saccharomyces paradoxus, Saccharomyces uvarum* and *Saccharomyces bayanus; Schizosaccharomyces* such as *Schizosaccharomyces pombe, Schizosaccharomyces japonicus, Schizosaccharomyces octosporus* and *Schizosaccharomyces cryophilus; Torulaspora* such as *Torulaspora delbrueckii; Kluyveromyces* such as *Kluyveromyces marxianus; Pichia* such as *Pichia stipitis, Pichia pastoris* or *Pichia angusta, Zygosaccharomyces* such as *Zygosaccharomyces bailii; Brettanomyces* such as *Brettanomyces inter medius, Brettanomyces bruxellensis, Brettanomyces anomalus, Brettanomyces custersianus, Brettanomyces naardenensis, Brettanomyces nanus, Dekkera bruxellensis* and *Dekkera anomala; Metschmkowia, Kloeckera* such as *Kloeckera apiculata; Aureobasidium* such as *Aureobasidium pullulans*. Other examples of fungi can include *Trichoderma reesei, Aspergillus niger, Chrysosporium lucknowense*, and *Aspergillus oryzae.*

Polynucleotides

Polynucleotides contain less than an entire microbial genome and can be single- or double-stranded nucleic acids. A polynucleotide can be RNA, DNA, cDNA, genomic DNA, chemically synthesized RNA or DNA or combinations thereof. A polynucleotide can comprise, for example, a gene, open reading frame, non-coding region, or regulatory element.

A gene is any polynucleotide molecule that encodes a polypeptide, protein, or fragments thereof, optionally including one or more regulatory elements preceding (5' non-coding sequences) and following (3' non-coding sequences) the coding sequence. In one embodiment, a gene does not include regulatory elements preceding and following the coding sequence. A native or wild-type gene refers to a gene as found in nature, optionally with its own regulatory elements preceding and following the coding sequence. A chimeric or recombinant gene refers to any gene that is not a native or wild-type gene, optionally comprising regulatory elements preceding and following the coding sequence, wherein the coding sequences and/or the regulatory elements, in whole or in part, are not found together in nature. Thus, a chimeric gene or recombinant gene can comprise regulatory elements and coding sequences that are derived from different sources, or regulatory elements and coding sequences that are derived from the same source but arranged differently than is found in nature. A gene can encompass full-length gene sequences (e.g., as found in nature and/or a gene sequence encoding a full-length polypeptide or protein) and can also encompass partial gene sequences (e.g., a fragment of the gene sequence found in nature and/or a gene sequence encoding a protein or fragment of a polypeptide or protein). A gene can include modified gene sequences (e.g., modified as compared to the sequence found in nature). Thus, a gene is not limited to the natural or full-length gene sequence found in nature.

Polynucleotides can be purified free of other components, such as proteins, lipids and other polynucleotides. For example, the polynucleotide can be 50%, 75%, 90%, 95%, 96%, 97%, 98%, 99%, or 100% purified. A polynucleotide existing among hundreds to millions of other polynucleotide molecules within, for example, cDNA or genomic libraries, or gel slices containing a genomic DNA restriction digest are not to be considered a purified polynucleotide. Polynucleotides can encode the polypeptides described herein (e.g., MAE1, PDC, GPD, g3473, g30588, NDE, GDH, DAK, g3837, SUC2).

Polynucleotides can comprise additional heterologous nucleotides that do not naturally occur contiguously with the polynucleotides. As used herein the term "heterologous" refers to a combination of elements that are not naturally occurring or that are obtained from different sources.

Polynucleotides can be isolated. An isolated polynucleotide is a naturally-occurring polynucleotide that is not immediately contiguous with one or both of the 5' and 3' flanking genomic sequences that it is naturally associated with. An isolated polynucleotide can be, for example, a recombinant DNA molecule of any length, provided that the nucleic acid sequences naturally found immediately flanking the recombinant DNA molecule in a naturally-occurring genome is removed or absent. Isolated polynucleotides also include non-naturally occurring nucleic acid molecules. Polynucleotides can encode full-length polypeptides, polypeptide fragments, and variant or fusion polypeptides.

Degenerate polynucleotide sequences encoding polypeptides described herein, as well as homologous nucleotide sequences that are at least about 80, or about 85, 90, 91, 92, 93, 94, 95, 96, 97, 98, or 99% identical to polynucleotides described herein and the complements thereof are also polynucleotides. Degenerate nucleotide sequences are polynucleotides that encode a polypeptide described herein or fragments thereof but differ in nucleic acid sequence from the wild-type polynucleotide sequence, due to the degeneracy of the genetic code. Complementary DNA (cDNA) molecules, species homologs, and variants of polynucleotides that encode biologically functional polypeptides also are polynucleotides.

Polynucleotides can be obtained from nucleic acid sequences present in, for example, a yeast or bacteria. Polynucleotides can also be synthesized in the laboratory, for example, using an automatic synthesizer. An amplification method such as PCR can be used to amplify polynucleotides from either genomic DNA or cDNA encoding the polypeptides.

Polynucleotides can comprise non-coding sequences or coding sequences for naturally occurring polypeptides or can encode altered sequences that do not occur in nature.

Unless otherwise indicated, the term polynucleotide or gene includes reference to the specified sequence as well as the complementary sequence thereof.

A polynucleotide can be a cDNA sequence or a genomic sequence. A "genomic sequence" is a sequence that is present or that can be found in the genome of an organism or a sequence that has been isolated from the genome of an organism. A cDNA polynucleotide can include one or more of the introns of a genomic sequence from which the cDNA sequence is derived. As another example, a cDNA sequence can include all of the introns of the genomic sequence from which the cDNA sequence is derived. Complete or partial intron sequences can be included in a cDNA sequence.

Polynucleotides as set forth in SEQ ID NO:51 through SEQ ID NO:58 a functional fragment thereof; or having at least 95% identity to SEQ ID NO:51-SEQ ID NO:58, are provided herein. In some embodiments, the isolated polynucleotides have at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO:51 through SEQ ID NO:58 or a functional fragment thereof.

The terms "sequence identity" or "percent identity" are used interchangeably herein. To determine the percent identity of two polypeptide molecules or two polynucleotide sequences, the sequences are aligned for optimal comparison purposes (e.g., gaps can be introduced in the sequence of a first polypeptide or polynucleotide for optimal alignment with a second polypeptide or polynucleotide sequence). The amino acids or nucleotides at corresponding amino acid or nucleotide positions are then compared. When a position in the first sequence is occupied by the same amino acid or nucleotide as the corresponding position in the second sequence, then the molecules are identical at that position. The percent identity between the two sequences is a function of the number of identical positions shared by the sequences (i.e., % identity=number of identical positions/total number of positions (i.e., overlapping positions)×100). In some embodiments the length of a reference sequence aligned for comparison purposes is at least 80% of the length of the comparison sequence, and in some embodiments is at least 90% or 100%. In an embodiment, the two sequences are the same length.

Ranges of desired degrees of sequence identity are approximately 80% to 100% and integer values in between. Percent identities between a disclosed sequence and a claimed sequence can be at least 80%, at least 83%, at least 85%, at least 90%, at least 95%, at least 98%, at least 99%, at least 99.5%, or at least 99.9%. In general, an exact match indicates 100% identity over the length of the reference sequence.

Polypeptides and polynucleotides that are sufficiently similar to polypeptides and polynucleotides described herein can be used herein. Polypeptides and polynucleotides that are about 90, 91, 92, 93, 94 95, 96, 97, 98, 99 99.5% or more identical to polypeptides and polynucleotides described herein can also be used herein. For example, a polynucleotide can have 80% 85%, 90%, 91%, 92%, 93%, 94%, 95%, 96%, 97%, 98%, 99% or more identity to any of the SEQ ID NOs described herein.

Expression Cassettes

A recombinant construct is a polynucleotide having heterologous polynucleotide elements. Heterologous polynucleotide elements are polynucleotides that do not occur together in nature. Any sequence of any origin can be a heterologous polynucleotide element in the polynucleotides provided herein. Exemplary heterologous polynucleotide elements include, for example, expression cassettes, cDNA sequences, genomic sequences, open reading frames (ORFs), regulatory elements, and others. Recombinant constructs include expression cassettes or expression constructs, which refer to an assembly that is capable of directing the expression of a polynucleotide or gene of interest. An expression cassette generally includes regulatory elements such as a promoter that is operably linked to (so as to direct transcription of) a polynucleotide and often includes a polyadenylation sequence or other regulatory elements as well.

An "expression cassette" refers to a fragment of DNA comprising a coding sequence of a selected gene or gene fragment or other polynucleotide (e.g. a polynucleotide encoding a polypeptide) and optionally, regulatory elements preceding (5' non-coding sequences) and following (3' non-coding sequences) the coding sequence that are required for expression of the selected gene product, fragment thereof, or other polynucleotide. The expression cassette is usually included within a vector, to facilitate cloning and transformation. Different expression cassettes can be transformed into different organisms including bacteria, yeast, plants and mammalian cells, as long as the correct regulatory elements are used for each host.

Generally, a polynucleotide or gene that is introduced into an organism is part of a recombinant construct. A polynucleotide can comprise a gene of interest, e.g., a coding sequence for a protein, or can be a sequence that is capable of regulating expression of a gene, such as a regulatory element. A recombinant construct can include, for example, regulatory elements operably linked 5' or 3' to a polynucleotide encoding one or more polypeptides of interest. For example, a promoter can be operably linked with a polynucleotide encoding one or more polypeptides of interest or a polynucleotide of interest (e.g., RNA) when it is capable of affecting the expression of the polynucleotide (i.e., the polynucleotide is under the transcriptional control of the promoter). Polynucleotides can be operably linked to regulatory elements in sense or antisense orientation. The expression cassettes or recombinant constructs can additionally contain a 5' leader polynucleotide. A leader polynucleotide can contain a promoter as well as an upstream region of a gene. The regulatory elements (i.e., promoters, enhancers, transcriptional regulatory regions, translational regulatory regions, translational termination regions, etc.) and/or the polynucleotide encoding a signal anchor can be native/endogenous to the host cell or to each other. Alternatively, the regulatory elements can be heterologous to the host cell or to each other. The expression cassette or recombinant construct can additionally contain one or more selectable marker genes.

A polynucleotide can be operably linked when it is positioned adjacent to or close to one or more regulatory elements, which direct transcription and/or translation of the polynucleotide.

A nucleic acid expression cassette can be a circular or linear nucleic acid molecule. In some cases, a nucleic acid expression cassette is delivered to cells (e.g., a plurality of different cells or cell types including target cells or cell types and/or non-target cell types) in a vector (e.g., an expression vector).

A fragment of a polynucleotide, polypeptide, or protein is meant to refer to a sequence that is less than a "full-length" sequence. A functional fragment includes "fragments," "variants," "analogues," or "chemical derivatives" of a molecule. A functional fragment comprises at least a biologically active fragment, which is a fragment that retains a biological activity (either functional or structural) that is substantially similar to a biological activity of the full-length polynucleotide, polypeptide, or protein. A biological activity of a polynucleotide can be its ability to influence expression in a manner known to be attributed to the full-length sequence. For example, a functional fragment of a regulatory element such as a promoter, for example, will retain the ability to influence transcription as compared to the full-length regulatory element. As used herein, the term "functional variant" refers to a sequence that is substantially similar in structure and biological activity to either the entire molecule, or to a fragment thereof. For example, a "functional variant" can have one or more sequence alterations or one or more sequence differences compared to the molecule or a fragment thereof while having similar biological activity.

A polynucleotide can be transcribed from a nucleic acid template into product of interest, such as a tRNA or mRNA for example; and a transcribed mRNA can subsequently be translated into peptides, polypeptides, or proteins of interest. Transcripts and encoded polypeptides can be collectively referred to as "gene product." A polypeptide is a linear polymer of amino acids that are linked by peptide bonds.

An expression cassette can comprise a fragment of DNA comprising a coding sequence of a selected gene and regulatory elements preceding (5' non-coding sequences) and following (3' non-coding sequences) the coding sequence that are required for expression of the selected gene product. Thus, an expression cassette is typically composed of: 1) a promoter sequence; 2) one or more coding sequences ["ORF"]; and, 3) a 3' untranslated region (i.e., a terminator) that, in eukaryotes, usually contains a polyadenylation site. The expression cassette is usually included within a vector, to facilitate cloning and transformation. Different expression cassettes can be transformed into different organisms including bacteria, yeast, plants, and mammalian cells, as long as the correct regulatory elements are used for each host.

Methods for preparing polynucleotides operably linked to a regulatory elements and expressing polypeptides in a host cell are well-known in the art. See, e.g., U.S. Pat. No. 4,366,246. A polynucleotide can be operably linked when it is positioned adjacent to or close to one or more regulatory elements, which direct transcription and/or translation of the polynucleotide.

A promoter is a nucleotide sequence that is capable of controlling the expression of a coding sequence or gene. Promoters are generally located 5' of the sequence that they regulate. Promoters can be derived in their entirety from a native gene, or be composed of different elements derived from promoters found in nature, and/or comprise synthetic nucleotide segments. Those skilled in the art will readily ascertain that different promoters can regulate expression of a coding sequence or gene in response to a particular stimulus, e.g., in a cell-specific manner, in response to different environmental or physiological conditions, or in response to specific compounds. Promoters are typically classified into two classes: inducible and constitutive. A constitutive promoter refers to a promoter that allows for continual transcription of the coding sequence or gene under its control.

An inducible promoter refers to a promoter that initiates increased levels of transcription of the coding sequence or gene under its control in response to a stimulus or an exogenous environmental condition. If inducible, there are inducer polynucleotides present therein that mediate regulation of expression so that the associated polynucleotide is transcribed only when an inducer molecule is present. A directly inducible promoter refers to a regulatory region, wherein the regulatory region is operably linked to a gene encoding a protein or polypeptide, where, in the presence of an inducer of the regulatory region, the protein or polypeptide is expressed. An indirectly inducible promoter refers to a regulatory system comprising two or more regulatory regions, for example, a first regulatory region that is operably linked to a first gene encoding a first protein, polypeptide, or factor, e.g., a transcriptional regulator, which is capable of regulating a second regulatory region that is operably linked to a second gene, the second regulatory region may be activated or repressed, thereby activating or repressing expression of the second gene. Both a directly inducible promoter and an indirectly inducible promoter are encompassed by inducible promoter.

A promoter can be any polynucleotide that shows transcriptional activity in the chosen host microorganism. A promoter can be naturally-occurring, can be composed of portions of various naturally-occurring promoters, or may be partially or totally synthetic. Guidance for the design of promoters is derived from studies of promoter structure, such as that of Harley and Reynolds, Nucleic Acids Res., 15, 2343-61 (1987). In addition, the location of the promoter relative to the transcription start can be optimized. Many suitable promoters for use in microorganisms and yeast are available, as are polynucleotides that enhance expression of an associated expressible polynucleotide.

A selectable marker can provide a means to identify microorganisms that express a desired product. Selectable markers include, but are not limited to, ampicillin resistance such as *E. coli*, neomycin phosphotransferase, which confers resistance to the aminoglycosides neomycin, kanamycin and paromycin (Herrera-Estrella, EMBO J. 2:987-995, (1983)); dihydrofolate reductase, which confers resistance to methotrexate (Reiss, Plant Physiol. (Life Sci. Adv.) 13:143-149, (1994)); trpB, which allows cells to utilize indole in place of tryptophan; hisD, which allows cells to utilize histinol in place of histidine (Hartman, Proc. Natl. Acad. Sci., USA 85:8047, (1988)); mannose-6-phosphate isomerase which allows cells to utilize mannose (WO 94/20627); hygro, which confers resistance to hygromycin (Marsh, Gene 32:481-485, (1984)); ornithine decarboxylase, which confers resistance to the ornithine decarboxylase inhibitor, 2-(difluoromethyl)-DL-ornithine (DFMO; McConlogue, In: Current Communications in Molecular Biology, Cold Spring Harbor Laboratory ed., (1987)); deaminase from *Aspergillus terreus*, which confers resistance to Blasticidin S (Tamura, Biosci. Biotechnol. Biochem. 59:2336-2338, (1995)); phosphinothricin acetyltransferase gene, which confers resistance to phosphinothricin (White et al., Nucl. Acids Res. 18:1062, (1990); Spencer et al., Theor. Appl. Genet. 79:625-633, (1990)); a mutant acetolactate synthase, which confers imidazolione or sulfonylurea resistance (Lee et al., EMBO J. 7:1241-1248, (1988)), a mutant EPSPV-synthase, which confers glyphosate resistance (Hinchee et al., BioTechnology 91:915-922, (1998)); a mutant psbA, which confers resistance to atrazine (Smeda et al., Plant Physiol. 103:911-917, (1993)), a mutant protoporphyrinogen oxidase (see U.S. Pat. No. 5,767,373), or other markers conferring resistance to an herbicide such as glufosinate.

A transcription termination region of a recombinant construct or expression cassette is a downstream regulatory region including a stop codon and a transcription terminator sequence. Transcription termination regions that can be used can be homologous to the transcriptional initiation region, can be homologous to the polynucleotide encoding a polypeptide of interest, or can be heterologous (i.e., derived from another source). A transcription termination region or can be naturally occurring, or wholly or partially synthetic. 3' non-coding sequences encoding transcription termination regions may be provided in a recombinant construct or expression construct and may be from the 3' region of the gene from which the initiation region was obtained or from a different gene. A large number of termination regions are known and function satisfactorily in a variety of hosts when utilized in both the same and different genera and species from which they were derived. Termination regions can also be derived from various genes native to the preferred hosts. The termination region is usually selected more for convenience rather than for any particular property.

Genetic Manipulation of Yeast for Production of Succinic Acid

In certain aspects one or more polynucleotides encoding one or more of pyruvate carboxylase (PYC), malate dehydrogenase (MDH), fumarase (FUMR), fumarate reductase (FDR); dicarboxylic acid transporter (MAE1); glycerol dehydrogenase (GDH) and dihydroxyacetone kinase (DAK) can be transformed into or added to a yeast cell to make a recombinant yeast cell. In an aspect, polynucleotides encoding dihydroxyacetone kinase (DAK) can be overexpressed in a yeast cell. For example, an existing polynucleotide in a yeast cell can be manipulated to express more DAK than a wild type cell by, for example, operably linking a strong promoter to a polynucleotide encoding DAK.

In an aspect a yeast cell can be genetically engineered to express a reductive TCA cycle. Reductive TCA cycle genes pyc, mdh, fumr and frd, encoding pyruvate carboxylase, malate dehydrogenase, fumarase and fumarate reductase, respectively, can be added to recombinant yeast to improve succinic acid production.

To obtain high transcription levels, the pyc, mdh, fumr and frd genes can be individually cloned to downstream of strong promoters fba1p, tef1ap, pgk1p and tdh3p, respectively. Any suitable promoter, however, can be used.

In an aspect, a recombinant yeast such as Issatchenkia, (e.g., *Issatchenkia orientalis* or *I. hanoiensis*) comprises heterologous polynucleotides encoding pyruvate carboxylase (PYC), malate dehydrogenase (MDH), fumarase (FUMR) and fumarate reductase (FDR); heterologous polynucleotide encoding dicarboxylic acid transporter (MAE1); a deleted or non-functional pyruvate decarboxylase (PCD) gene; a deleted or non-functional glycerol 3-phosphate dehydrogenase (GPD) gene; a deleted or non-functional JEN carboxylate transporter gene; a heterologous polynucleotide encoding glycerol dehydrogenase (GDH); an overexpressed dihydroxyacetone kinase (DAK) gene; and a deleted or non-functional g3837 hexokinase or a heterologous polynucleotide encoding invertase (SUC2). In an aspect, the recombinant yeast can additional have a deleted or non-functional NADH dehydrogenase (NDE) gene.

In an aspect a heterologous polynucleotide encodes pyruvate carboxylase (PYC), malate dehydrogenase (MDH), fumarase (FUMR), fumarate reductase (FRD), dicarboxylic acid transporter (MAE1), glycerol dehydrogenase (GDH); invertase (SUC2), dihydroxyacetone kinase (DAK), or combinations thereof.

In an aspect, a polynucleotide encodes an PYC polypeptide having 75, 80, 85, 90, 92, 94, 95, 96, 97, 98, 99% or more sequence identity to SEQ ID NO:62.

SEQ ID NO: 62

```
MSTVEDHSSLHKLRKESEILSNANKILVANRGEIPIRIFRSAHELSMHT

VAIYSHEDRLSMHRLKADEAYAIGKTGQYSPVQAYLQIDEIIKIAKEHD

VSMIHPGYGFLSENSEFAKKVEESGMIWVGPPAEVIDSVGDKVSARNLA

IKCDVPVVPGTDGPIEDIEQAKQFVEQYGYPVIIKAAFGGGGRGMRVVR

EGDDIVDAFQRASSEAKSAFGNGTCFIERFLDKPKHIEVQLLADNYGNT

IHLFERDCSVQRRHQKVVEIAPAKTLPVEVRNAILKDAVTLAKTANYRN

AGTAEFLVDSQNRHYFIEINPRIQVEHTITEEITGVDIVAAQIQIAAGA
```

-continued

```
SLEQLGLLQNKITTRGFAIQCRITTEDPAKNFAPDTGKIEVYRSAGGNG

VRLDGGNGFAGAVISPHYDSMLVKCSTSGSNYEIARRKMIRALVEFRIR

GVKTNIPFLLALLTHPVFISGDCWTTFIDDTPSLFEMVSSKNRAQKLLA

YIGDLCVNGSSIKGQIGFPKLNKEAEIPDLLDPNDEVIDVSKPSTNGLR

PYLLKYGPDAFSKKVRGFDGCMIMDTTWRDAHQSLLATRVRTIDLLRIA

PTTSHALQNAFALECWGGATFDVAMRFLYEDPWERLRQLRKAVPNIPFQ

MLLRGANGVAYSSLPDNAIDHFVKQAKDNGVDIFRVFDALNDLEQLKVG

VDAVKKAGGVVEATVCYSGDMLIPGKKYNLDYYLETVGKIVEMGTHILG

IKDMAGTLKPKAAKLLIGSIRSKYPDLVIHVHTHDSAGTGISTYVACAL

AGADIVDCAINSMSGLTSQPSMSAFIAALDGDIETGVPEHFARQLDAYW

AEMRLLYSCFEADLKGPDPEVYKHEIPGGQLTNLIFQAQQVGLGEQWEE

TKKKYEDANMLLGDIVKVTPTSKVVGDLAQFMVSNKLEKEDVEKLANEL

DFPDSVLDFFEGLMGTPYGGFPEPLRTNVISGKRRKLKGRPGLELEPFN

LEEIRENLVSRFGPGITECDVASYNMYPKVYEQYRKVVEKYGDLSVLPT

KAFLAPPTIGEEVHVEIEQGKTLIIKLLAISDLSKSHGTREVYFELNGE

MRKVTIEDKTAAIETVTRAKADGHNPNEVGAPMAGVVVEVRVKHGTEVK

KGDPLAVLSAMKMEMVISAPVSGRVGEVFVNEGDSVDMGDLLVKIAKDE

APA
```

Examples of other PYC polypeptides that can be used include GenBank Accession Numbers KGK39181.1, XP_029319118.1, OUT23134.1, TID29929.1, XP_019019553.1, KAG0683263.1, GAV29513.1, KAG7903633.1, XP_013934039.1 and XP_018211803.1.

In an aspect, a polynucleotide encodes an MDH polypeptide having 75, 80, 85, 90, 92, 94, 95, 96, 97, 98, 99% or more sequence identity to SEQ ID NO:63.

SEQ ID NO: 63

```
MVKVTILGAAGGIGQPLSLLLRLNPWIDELALFDIVNTPGVSCDLSHIP

ASQVVNGYAPKSKSDTETIKTALKGADIVVIPAGIPRKPGMTRNDLFKI

NAGIVKSLIHSAGTTCPDAFICVISNPVNSTVPIAVEELKRLNVFNPHK

VFGITTLDNFRLEEFLSGELGGIVKPNDLYGDVVAIGGHSGDSIVPILN

SWNLNFINDGDSYNKLVKRVQFGGDEVVKAKDGKGSATLSMATAAYRFV

NNLLDAIVNNKKVKEVAFVKIDQLPTTRVPYFVVDETQYFSLPIILGRQ

GIERVTFPESLTEQEVRMTKHAVAKVKVDVNKGFNFVHG
```

Examples of other MDH polypeptides that can be used include GenBank Accession Numbers KGK36641.1, XP_029319610.1, OUT23611.1, GAV27421.1, XP_019020246.1, and KAG0673269.1.

In an aspect, a polynucleotide encodes an FUMR polypeptide having 75, 80, 85, 90, 92, 94, 95, 96, 97, 98, 99% or more sequence identity to SEQ ID NO:64.

SEQ ID NO: 64

```
MFSTTSIAKRIEKDAFGDIEVPNEKYWGAQTQRSLQNFKIGGKREVMPE

PIIKSFGILKKATAKINAESGALDPKLSEAIQQAATEVYEGKLMDHFPL
```

-continued

VVFQTGSGTQSNMNANEVISNRAIEILGGELGSKTPVHPNDHVNMSQSS

NDTFPTVMHIAAVTEVSSHLLPELTALRDALQKKSDEFKNIIKIGRTHL

QDATPLTLGQEFSGYVQQCTNGIKRIEIALEHLRYLAQGGTAVGTGLNT

KKGFAEKVANEVTKLTGLQFYTAPNKFEALAAHDAVVEMSGALNTVAVS

LFKIAQDIRYLGSGPRCGYGELALPENEPGSSIMPGKVNPTQNEALTML

CTQVFGNHSCITFAGASGQFELNVFKPVMISNLLSSIRLLGDGCNSFRI

HCVEGIIANTDKIDKLLHESLMLVTALNPHIGYDKASKIAKNAHKKGLT

LKQSALELGYLTEEQFNEWVRPENMIGPKD

Examples of other FUMR polypeptides that can be used include GenBank Accession Numbers XP_029320281.1, KAG0675622.1, KAG0688010.1, TID15780.1, XP_019017445.1, GAV28471.1, ONH70427.1, KAG7865831.1, XP_018210135.1, and XP_013936161.1.

In an aspect, a polynucleotide encodes an FRD polypeptide having 75, 80, 85, 90, 92, 94, 95, 96, 97, 98, 99% or more sequence identity to SEQ ID NO:65.

SEQ ID NO: 65

MVDGRSSASIVAVDPERAARERDAAARALLQDSPLHTTMQYATSGLELT

VPYALKVVASADTFDRAKEVADEVLRCAWQLADTVLNSFNPNSEVSLVG

RLPVGQKHQMSAPLKRVMACCQRVYNSSAGCFDPSTAPVAKALREIALG

KERNNACLEALTQACTLPNSFVIDFEAGTISRKHEHASLDLGGVSKGYI

VDYVIDNINAAGFQNVFFDWGGDCRASGMNARNTPWVVGITRPPSLDML

PNPPKEASYISVISLDNEALATSGDYENLIYTADDKPLTCTYDWKGKEL

MKPSQSNIAQVSVKCYSAMYADALATACFIKRDPAKVRQLLDGWRYVRD

TVRDYRVYVRENERVAKMFEIATEDAEMRKRRISNTLPARVIVVGGGLA

GLSAAIEAAGCGAQVVLMEKEAKLGGNSAKATSGINGWGTRAQAKASIV

DGGKYFERDTYKSGIGGNTDPALVKTLSMKSADAIGWLTSLGVPLTVLS

QLGGHSRKRTHRAPDKKDGTPLPIGFTIMKTLEDHVRGNLSGRITIMEN

CSVTSLLSETKERPDGTKQIRVTGVEFTQAGSGKTTILADAVILATGGF

SNDKTADSLLREHAPHLVNFPTTNGPWATGDGVKLAQRLGAQLVDMDKV

QLHPTGLINPKDPANPTKFLGPEALRGSGGVLLNKQGKRFVNELDLRSV

VSKAIMEQGAEYPGSGGSMFAYCVLNAAAQKLFGVSSHEFYWKKMGLFV

KADTMRDLAALIGCPVESVQQTLEEYERLSISQRSCPITRKSVYPCVLG

TKGPYYVAFVTPSIHYTMGGCLISPSAEIQMKNTSSRAPLSHSNPILGL

FGAGEVTGGVHGGNRLGGNSLLECVVFGRIAGDRASTILQRKSSALSFK

VWTTVVLREVREGGVYGAGSRVLRFNLPGALQRSGLSLGQFIAIRGDWD

GQQLIGYYSPITLPDDLGMIDILARSDKGTLREWISALEPGDAVEMKAC

GGLVIERRLSDKHFVFMGHIINKLCLIAGGTGVAPMLQIIKAAFMKPFI

DTLESVHLIYAAEDVTELTYREVLEERRRESRGKFKKTFVLNRPPPLWT

DGVGFIDRGILTNHVQPPSDNLLVAICGPPVMQRIVKATLKTLGYNMNL

VRTVDETEPSGS

Examples of other FRD polypeptides that can be used include GenBank Accession Numbers ALM30213.1, AAN40014.1, AAX20163.1, XP_844767.1, KAH8614254.1, XP_011773278.1, KAH9597360.1, PBJ69489.1, XP_803046.1, and PWV12310.1.

In an aspect, a polynucleotide encodes an MAE1 polypeptide having 75, 80, 85, 90, 92, 94, 95, 96, 97, 98, 99% or more sequence identity to SEQ ID NO:59.

SEQ ID NO: 59

MGELKEILKQRYHELLDWNVKAPHVPLSQRLKHFTWSWFACTMATGGVG

LIIGSFPFRFYGLNTIGKIVYILQIFLFSLFGSCMLFRFIKYPSTIKDS

WNHHLEKLFIATCLLSISTFIDMLAIYAYPDTGEWMVWVIRILYYIYVA

VSFIYCVMAFFTIFNNHVYTIETASPAWILPIFPPMICGVIAGAVNSTQ

PAHQLKNMVIFGILFQGLGFWVYLLLFAVNVLRFFTVGLAKPQDRPGMF

MFVGPPAFSGLALINIARGAMGSRPYIFVGANSSEYLGFVSTFMAIFIW

GLAAWCYCLAMVSFLAGFFTRAPLKFACGWFAFIFPNVGFVNCTIEIGK

MIDSKAFQMFGHIIGVILCIQWILLMYLMVRAFLVNDLCYPGKDEDAHP

PPKPNTGVLNPTFPPEKAPASLEKVDTHVTSTGGESDPPSSEHESV

In an aspect, a polynucleotide encodes a GDH polypeptide having 75, 80, 85, 90, 92, 94, 95, 96, 97, 98, 99% or more sequence identity to SEQ ID NO:60.

SEQ ID NO: 60

MKGLLYYGTNDIRYSETVPEPEIKNPNDVKIKVSYCGICGTDLKEFTYS

GGPVFFPKQGTKDKISGYELPLCPGHEFSGTVVEVGSGVTSVKPGDRVA

VEATSHCSDRSRYKDTVAQDLGLCMACQSGSPNCCASLSFCGLGGASGG

FAEYVVYGEDHMVKLPDSIPDDIGALVEPISVAWHAVERARFQPGQTAL

VLGGGPIGLATILALQGHHAGKIVCSEPALIRRQFAKELGAEVFDPSTC

DDANAVLKAMVPENEGFHAAFDCSGVPQTFTTSIVATGPSGIAVNVAVW

GDHPIGFMPMSLTYQEKYATGSMCYTVKDFQEVVKALEDGLISLDKARK

MITGKVHLKDGVEKGFKQLIEHKENNVKILVTPNEVS

Examples of other GDH polypeptides that can be used include GenBank Accession Numbers KAG7900457.1, KAG7906280.1, KAG7877636.1, KAG7727406.1, KAG7703882.1, XP_043057395.1, and XP_046058849.1.

In an aspect, a polynucleotide encodes a SUC2 polypeptide having 75, 80, 85, 90, 92, 94, 95, 96, 97, 98, 99% or more sequence identity to SEQ ID NO:61.

SEQ ID NO: 61

MLLQAFLFLLAGFAAKISASMTNETSDRPLVHFTPNKGWMNDPNGLWYD

EKDAKWHLYFQYNPNDTVWGTPLFWGHATSDDLTNWEDQPIAIAPKRND

SGAFSGSMVVDYNNTSGFFNDTIDPRQRCVAIWTYNTPESEEQYISYSL

DGGYTFTEYQKNPVLAANSTQFRDPKVFWYEPSQKWIMTAAKSQDYKIE

IYSSDDLKSWKLESAFANEGFLGYQYECPGLIEVPTEQDPSKSYWVMFI

SINPGAPAGGSFNQYFVGSFNGTHFEAFDNQSRVVDFGKDYYALQTFFN

TDPTYGSALGIAWASNWEYSAFVPTNPWRSSMSLVRKFSLNTEYQANPE

TELINLKAEPILNISNAGPWSRFATNTTLTKANSYNVDLSNSTGTLEFE

LVYAVNTTQTISKSVFADLSLWFKGLEDPEEYLRMGFEVSASSFFLDRG

-continued

```
NSKVKFVKENPYFTNRMSVNNQPFKSENDLSYYKVYGLLDQNILELYF

NDGDVVSTNTYFMTTGNALGSVNMTTGVDNLFYIDKFQVREVK
```

Examples of other SUC2 polypeptides that can be used include CAI4298301.1, CAI4243981.1, CBK52121.1, CAI4732522.1, and CAI4522677.1

In an aspect, a polynucleotide encodes an DAK polypeptide having 75, 80, 85, 90, 92, 94, 95, 96, 97, 98, 99% or more sequence identity to SEQ ID NO:66.

```
                                        SEQ ID NO: 66
MSQEKHWNYTKDIVRTSISGVCAANPYLKYIESERVVYNSHSPENGEEK

VTVVSGGGSGHEPLHLGFVGDALLDVAVAGSIFASPSVKQVLSGIHSKP

SKKGTVVVVKNYTGDILHFGLAIERARSQGINAGLLIVQDDVSVGKTKN

GKVGRRGLAGTALVHKLVGAKSFVDGCKASLDDVMDLGQRVIDNMVTIG

ASLDRVVIPTVHGEEKQDDSDDEDEKIDELGKDEIEIGMGIHNEHGIKR

VSPIPTVDQLAETLLAYLLDPNDKERYYVDFDKDDDVVLLINNLGSTSV

LELYAIQAIVNEKLFSIYNIKPVRIYTGTFVTSLDGPGISITLLNVTKA

GGDEILRLLDLPTNAPGWNSAIQSSDWKTLGEQLVKEAPEIHYATSSIK

LDPELVKKILLKGCEEVKKVEPKVTLYDTVAGDGDCGETLLAGADSITN

SLRDNSIDLTDAVRFFEELGDVVESAMGGTSGGLYSIFISSMSSFLKQQ

EKSRGAFTVSEEDFADTLEAGLKGLQRYTRARVGDRTLMDALIPFVETF

KSTGDINKAAQAAHDGAESTRKLAAKFGRASYVAEEEFRRFDSEGGLPD

PGAIGLAALINGFVSAYQS
```

Examples of other DAK polypeptides that can be used include GenBank Accession Numbers XP_029319382.1, OUT23390.1, ONH76879.1, KGK38737.1, AUM56958.1, XP_019019972.1, GAV26795.1, KAG0681805.1, and TID29658.1.

In an aspect, a sequence of a polynucleotide can be codon optimized for expression in a particular yeast such as/. *orientalis*. Codon optimization can be used to improve the codon composition of a recombinant gene based on various criteria without altering the amino acid sequence. Codon optimization tools are available from, for example, Integrated DNA Technologies. In an aspect, polynucleotides encoding MAE1, PDC, GPD, g3473, g30588, NDE, GDH, DAK, g3837, and/or SUC2 can be codon optimized.

In an aspect, any of the genes discussed herein (e.g., polynucleotides encoding MAE1, PDC, GPD, g3473, g30588, NDE, GDH, DAK, g3837, and/or SUC2) can be overexpressed. Various methods can be used for expression and overexpression of polypeptides in a recombinant yeast cell. In particular, a polypeptide can be overexpressed by increasing the copy number of the gene coding for the polypeptide in the yeast cell, e.g. by integrating additional copies of the gene in the yeast cell's genome, by expressing the gene from an episomal multicopy expression vector, or by introducing a episomal expression vector that comprises multiple copies of the gene.

Alternatively, overexpression of polypeptides in yeast cells can be achieved by using a promoter that is not native to the sequence coding for the polypeptide to be overexpressed, i.e. a promoter that is heterologous to the coding sequence to which it is operably linked. Although the promoter can be heterologous to the coding sequence to which it is operably linked, it is also possible that the promoter is homologous, i.e., endogenous to the host cell. A heterologous promoter can be capable of producing a higher steady state level of the transcript comprising the coding sequence (or is capable of producing more transcript molecules, i.e., mRNA molecules, per unit of time) than is the promoter that is native to the coding sequence. Suitable promoters in this context include both constitutive and inducible natural promoters as well as engineered promoters.

The coding sequence used for overexpression of polypeptides can be homologous to the yeast cell. However, coding sequences that are heterologous to the yeast cell can also be used.

Overexpression of a polypeptide, when referring to the production of the polypeptide in a genetically modified yeast cell, means that the polypeptide is produced at a higher level of biological activity as compared to the unmodified yeast cell under identical conditions. Usually this means that the polypeptide is produced in greater amounts, or rather at a higher steady state level as compared to the unmodified yeast cell under identical conditions. Similarly, this can mean that the mRNA coding for the polypeptide is produced in greater amounts, or again rather at a higher steady state level as compared to the unmodified host cell under identical conditions. In a recombinant yeast call, an overexpressed polypeptide (e.g., DAK, GDH) can be overexpressed by at least a factor of about 1.1, about 1.2, about 1.5, about 2, about 5, about 10 or about 20 as compared to a strain which is genetically identical except for the genetic modification causing the overexpression. It is to be understood that these levels of overexpression can apply to the steady state level of the polypeptide's activity, as well as to the steady state level of the transcript coding for the enzyme.

Vectors

A recombinant construct or expression cassette can be contained within a vector. In addition to the components of the recombinant construct, the vector can include, in some examples, one or more selectable markers, a signal which allows the vector to exist as single-stranded DNA (e.g., a M13 origin of replication), at least one multiple cloning site, and an origin of replication (e.g., a SV40 or adenovirus origin of replication).

Vectors for stable transformation of microorganisms and yeast can be obtained from commercial vendors or constructed from publicly available sequence information. Expression vectors can be engineered to produce heterologous and/or homologous protein(s) of interest (e.g., MAE1, PDC, GPD, g3473, g30588, NDE, GDH, DAK, g3837, SUC2). Such vectors are useful for recombinantly producing a protein of interest and for modifying the natural phenotype of host cells.

If desired, polynucleotides can be cloned into an expression vector comprising expression control elements, including for example, origins of replication, promoters, enhancers, or other regulatory elements that drive expression of the polynucleotides in host cells. An expression vector can be, for example, a plasmid, such as pBR322, pUC, or ColE1, or an adenovirus vector, such as an adenovirus Type 2 vector or Type 5 vector. Optionally, other vectors can be used, including but not limited to Sindbis virus, simian virus 40, alphavirus vectors, poxvirus vectors, and cytomegalovirus and retroviral vectors, such as murine sarcoma virus, mouse mammary tumor virus, Moloney murine leukemia virus, and Rous sarcoma virus. Mini-chromosomes such as MC and MC1, bacteriophages, phagemids, yeast artificial chromosomes, bacterial artificial chromosomes, virus particles, virus-like particles, cosmids (plasmids into which phage lambda cos sites have been inserted) and replicons (genetic elements that are capable of replication under their own control in a cell) can also be used.

To confirm the presence of recombinant polynucleotides or recombinant genes in transgenic cells, a polymerase chain reaction (PCR) amplification or Southern blot analysis can be performed using methods known to those skilled in the art. Expression products of the recombinant polynucleotides or recombinant genes can be detected in any of a variety of ways, and include for example, western blot and enzyme assay. Once recombinant organisms have been obtained, they may be grown in cell culture.

Polypeptides

A polypeptide is a polymer of two or more amino acids covalently linked by amide bonds. A polypeptide can be post-translationally modified. A purified polypeptide is a polypeptide preparation that is substantially free of cellular material, other types of polypeptides, chemical precursors, chemicals used in synthesis of the polypeptide, or combinations thereof. A polypeptide preparation that is substantially free of cellular material, culture medium, chemical precursors, chemicals used in synthesis of the polypeptide, etc., has less than about 30%, 20%, 10%, 5%, 1% or more of other polypeptides, culture medium, chemical precursors, and/or other chemicals used in synthesis. Therefore, a purified polypeptide is about 70%, 80%, 90%, 95%, 99% or more pure. A purified polypeptide does not include unpurified or semi-purified cell extracts or mixtures of polypeptides that are less than 70% pure.

The term "polypeptides" can refer to one or more of one type of polypeptide (a set of polypeptides). "Polypeptides" can also refer to mixtures of two or more different types of polypeptides (a mixture of polypeptides). The terms "polypeptides" or "polypeptide" can each also mean "one or more polypeptides."

As used herein, the term "polypeptide of interest" or "polypeptides of interest", "protein of interest", "proteins of interest" includes any or a plurality of any of the MAE1, PDC, GPD, g3473, g30588, NDE, GDH, DAK, g3837, SUC2 polypeptides or other polypeptides (including variant polypeptides) described herein.

A mutated protein or polypeptide comprises at least one deleted, inserted, and/or substituted amino acid, which can be accomplished via mutagenesis of polynucleotides encoding these amino acids. Mutagenesis includes well-known methods in the art, and includes, for example, site-directed mutagenesis by means of PCR or via oligonucleotide-mediated mutagenesis as described in Sambrook et ai, Molecular Cloning-A Laboratory Manual, 2nd ed., Vol. 1-3 (1989).

As used herein, the term "sufficiently similar" means a first amino acid sequence that contains a sufficient or minimum number of identical or equivalent amino acid residues relative to a second amino acid sequence such that the first and second amino acid sequences have a common structural domain and/or common functional activity. For example, amino acid sequences that comprise a common structural domain that is at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 100% identical are defined herein as sufficiently similar. Variants will be sufficiently similar to the amino acid sequence of the polypeptides described herein. Such variants generally retain the functional activity of the polypeptides described herein. Variants include peptides that differ in amino acid sequence from the native and wild-type peptide, respectively, by way of one or more amino acid deletion(s), addition(s), and/or substitution(s). These may be naturally occurring variants as well as artificially designed ones.

Polypeptides and polynucleotides that are sufficiently similar to polypeptides and polynucleotides described herein (e.g., MAE1, PDC, GPD, g3473, g30588, NDE, GDH, DAK, g3837, SUC2) can be used herein. Polypeptides and polynucleotides that about 85, 90, 91, 92, 93, 94 95, 96, 97, 98, 99 99.5% or more homology or identity to polypeptides and polynucleotides described herein (e.g., MAE1, PDC, GPD, g3473, g30588, NDE, GDH, DAK, g3837, SUC2 and variants thereof) can also be used herein.

Polypeptides as set forth in SEQ ID NO:59 through SEQ ID NO:69, a functional fragment thereof; or having at least 95% identity to SEQ ID NO:59-SEQ ID NO: 6, are provided herein. In some embodiments, the isolated polypeptides have at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.9%, and any number or range in between, identity to SEQ ID NO: 59 through SEQ ID NO:69 or a functional fragment thereof.

Gene Disruptions and Mutations

A genetic mutation comprises a change or changes in a nucleotide sequence of a gene or related regulatory region or polynucleotide that alters the nucleotide sequence as compared to its native or wild-type sequence. Mutations include, for example, substitutions, additions, and deletions, in whole or in part, within the wild-type sequence. Such substitutions, additions, or deletions can be single nucleotide changes (e.g., one or more point mutations), or can be 2, 3, 4, 5, 6, 7, 8, 9, 10, or more nucleotide changes. Mutations can occur within the coding region of the gene or polynucleotide as well as within the non-coding and regulatory elements of a gene. A genetic mutation can also include silent and conservative mutations within a coding region as well as changes which alter the amino acid sequence of the polypeptide encoded by the gene or polynucleotide. A genetic mutation can, for example, increase, decrease, or otherwise alter the activity (e.g., biological activity) of the polypeptide product. A genetic mutation in a regulatory element can increase, decrease, or otherwise alter the expression of sequences operably linked to the altered regulatory element.

A gene disruption is a genetic alteration in a polynucleotide or gene that renders an encoded gene product (e.g., MAE1, PDC, GPD, g3473, g30588, NDE, GDH, DAK, g3837, SUC2) attenuated or more active (e.g., produced at a lower amount, greater amount or having higher or lower biological activity). A gene disruption can include a disruption in a polynucleotide or gene that results in reduced expression of an encoded gene product, or expression of a gene product with increased or reduced or attenuated biological activity. The genetic alteration can be, for example, or addition or deletion of a regulatory element required for transcription or translation of the polynucleotide or gene, deletion or addition of a regulatory element required for transcription or translation or the polynucleotide or gene, addition of a different regulatory element required for transcription or translation or the gene or polynucleotide, deletion of a portion (e.g. 1, 2, 3, 6, 9, 21, 30, 60, 90, 120 or more nucleic acids) of the gene or polynucleotide, which results in an partially active gene product or a gene product with greater activity, replacement of a gene's promoter with a weaker promoter or a stronger promoter, replacement or insertion of one or more amino acids of the encoded protein to reduce its activity, stability, or concentration, to increase its activity, stability, or concentration, or inactivation or activation of a gene's transactivating factor such as a regulatory protein.

Zinc-finger nucleases (ZFNs), Talens, and CRISPR-Cas9 allow double strand DNA cleavage at specific sites in yeast chromosomes such that targeted gene insertion or deletion can be performed (Shukla et al., 2009, Nature 459:437-441; Townsend et al., 2009, Nature 459:442-445). This approach can be used to modify the promoter of endogenous genes or the endogenous genes themselves to modify expression of MAE1, PDC, GPD, g3473, g30588, NDE, GDH, DAK, g3837, SUC2 which can be present in the genome of yeast of interest. ZFNs, Talens or CRISPR/Cas9 can be used to change the sequences regulating the expression of the polypeptides to increase or decrease the expression or alter the timing of expression beyond that found in a non-engineered or wild-type yeast, or to delete the wild-type polynucleotide, or replace it with a deleted or mutated form to alter the expression (e.g., increase or decrease) and/or activity of MAE1, PDC, GPD, g3473, g30588, NDE, GDH, DAK, g3837, SUC2.

In certain aspects one or more polynucleotides of a yeast cell can deleted or rendered non-functional such that the polypeptides encoded by the polynucleotides are not expressed, are expressed, but have little to no biological activity, or are expressed at levels that 50, 60, 70, 80, 90, 95, 99, 99.5, or 100% less than a wild-type yeast cell. In an aspect one or more of a pyruvate decarboxylase (PCD) gene, a glycerol 3-phosphate dehydrogenase (GPD) gene, JEN carboxylate transporter gene (e.g., g3473 or g3068), a NADH dehydrogenase (NDE) gene, and a g3837 hexokinase gene is deleted or rendered non-functional. This can be accomplished using ZFNs, Talens, and CRISPR-Cas9 as described above, or other genetic engineering techniques. In an aspect, a PCD gene comprises SEQ ID NO:51. In an aspect, a GPD gene comprises SEQ ID NO:52. In an aspect, a JEN carboxylate transporter gene is shown in SEQ ID NO:53 and/or SEQ ID NO: 54. In an aspect an NDE gene is shown in SEQ ID NO:55.

Methods of Making Succinic Acid

In certain aspects, fermentation methods for producing succinic acid are provided. Methods can comprise contacting a fermentation medium with one or more recombinant yeast strains as described herein, e.g., a Issatchenkia yeast, and fermenting the fermentation medium and the recombinant Issatchenkia yeast wherein succinic acid is produced. The succinic acid can be collected and purified from the fermentation medium. A fermentation medium can comprise glucose and glycerol. Glucose and glycerol can be present in a medium at a ratio of about 1:1, 2:1, 3:1, or 5:2. A fermentation medium can comprise sucrose, sugarcane juice, sugar beets, sweet sorghum, switchgrass substrate, *miscanthus* substrate, corn substrate, cassava substrate, or any other suitable medium. A fermentation medium can comprise sucrose, glucose, and fructose.

A pH of the fermentation medium during fermentation medium can be about 2.0, 2.5, 3.0, 3.5, 4.0, or 4.5. In an aspect no acid is added to the fermentation medium during the fermenting, after fermentation prior to succinic acid collection, or during succinic acid collection, or during fermentation and succinic acid collection. In an aspect, no neutralizing agents, such as lime ($CaCO_3$) or base (NaOH), are added to maintain neutral pH environment during fermentation.

In an aspect a $CO_2$ flow rate during fermentation can be set to about 0.0, 0.1, 0.2, 0.3, 0.4, 0.5 or more vvm. An $O_2$ flow rate can be cascaded to maintain DO (dissolved oxygen) of about 4, 5, 6, 7, 8, 9, 10, 11% or more.

Succinic acid can be produced at more than about 40, 50, 60, 70, 80, 90, 100, 110, 120, 130, 140, 150, or 160 g/L. A yield of succinic acid of about 0.40, 0.50, 0.60, 0.70, 0.80, 0.90 g/g glucose equivalent or more can be achieved. A productivity of about 0.20, 0.30, 0.40, 0.50, 0.60, 0.70, 0.80, 0.90 g/L/h or more can be achieved.

Succinic acid can be collected using any suitable method including, for example, vacuum distillation and crystallization.

A substrate or medium can be fermented with a recombinant yeast to form a fermented medium comprising succinic acid. Fermentation can be carried out as batch fermentation, fed-batch fermentation, continuous fermentation, or semi-continuous fermentation. In batch fermentation, all of the medium and the yeast are added to a fermenter and are fermentation occurs until the yeast has converted the medium to succinic acid to the desired degree. In fed-batch fermentation, a yeast suspension, optionally containing some medium, is charged to a fermenter and medium is fed to the fermenter over a period of time during which the yeast converts the medium to succinic acid. After the feeding of the medium is stopped, fermentation is continued for a further time period to complete conversion of the medium to succinic acid before the fermenter is discharged. In continuous fermentation, yeast and medium are fed continuously to a fermenter and a corresponding amount of fermented medium is withdrawn continuously to maintain the amount of material inside the fermenter essentially constant. In semi-continuous fermentation, yeast and medium are fed continuously, but fermented medium is withdrawn from the fermenter at intervals. In an aspect a fermenter and fermentation can comprise about 0.5, 1, 5, 10, 25, 50, 75, 100, 500, 1,000 liters or more.

In an aspect, the fermentation medium is a minimal medium. A minimal medium differs from a rich medium in that it does not contain a source of all amino acids. In an aspect, a yeast minimal media does not comprise yeast extract, peptones, or both yeast extract and peptones. Peptones are Peptones are water-soluble protein hydrolysates, containing peptides, amino acids, and inorganic salts as well as other compounds, such as lipids, vitamins, and sugars.

The compositions and methods are more particularly described below and the Examples set forth herein are intended as illustrative only, as numerous modifications and variations therein will be apparent to those skilled in the art. The terms used in the specification generally have their ordinary meanings in the art, within the context of the compositions and methods described herein, and in the specific context where each term is used. Some terms have been more specifically defined herein to provide additional guidance to the practitioner regarding the description of the compositions and methods.

As used herein, the term "and/or" includes any and all combinations of one or more of the associated listed items. As used in the description herein and throughout the claims that follow, the meaning of "a", "an", and "the" includes plural reference as well as the singular reference unless the context clearly dictates otherwise. The term "about" in association with a numerical value means that the value varies up or down by 5%. For example, for a value of about 100, means 95 to 105 (or any value between 95 and 105).

All patents, patent applications, and other scientific or technical writings referred to anywhere herein are incorporated by reference herein in their entirety. The embodiments illustratively described herein suitably can be practiced in the absence of any element or elements, limitation or limitations that are specifically or not specifically disclosed herein. Thus, for example, in each instance herein any of the terms "comprising," "consisting essentially of," and "consisting of" can be replaced with either of the other two terms, while retaining their ordinary meanings. The terms and expressions which have been employed are used as terms of description and not of limitation, and there is no intention that in the use of such terms and expressions of excluding any equivalents of the features shown and described or portions thereof, but it is recognized that various modifications are possible within the scope of the claims. Thus, it should be understood that although the present methods and compositions have been specifically disclosed by embodiments and optional features, modifications and variations of the concepts herein disclosed can be resorted to by those skilled in the art, and that such modifications and variations are considered to be within the scope of the compositions and methods as defined by the description and the appended claims.

Any single term, single element, single phrase, group of terms, group of phrases, or group of elements described herein can each be specifically excluded from the claims.

Whenever a range is given in the specification, for example, a temperature range, a time range, a composition, or concentration range, all intermediate ranges and subranges, as well as all individual values included in the ranges given are intended to be included in the disclosure. It will be understood that any subranges or individual values in a range or subrange that are included in the description herein can be excluded from the aspects herein. It will be understood that any elements or steps that are included in the description herein can be excluded from the claimed compositions or methods.

In addition, where features or aspects of the compositions and methods are described in terms of Markush groups or other grouping of alternatives, those skilled in the art will recognize that the compositions and methods are also thereby described in terms of any individual member or subgroup of members of the Markush group or other group.

The following are provided for exemplification purposes only and are not intended to limit the scope of the embodiments described in broad terms above.

EXAMPLES

Figure 1:
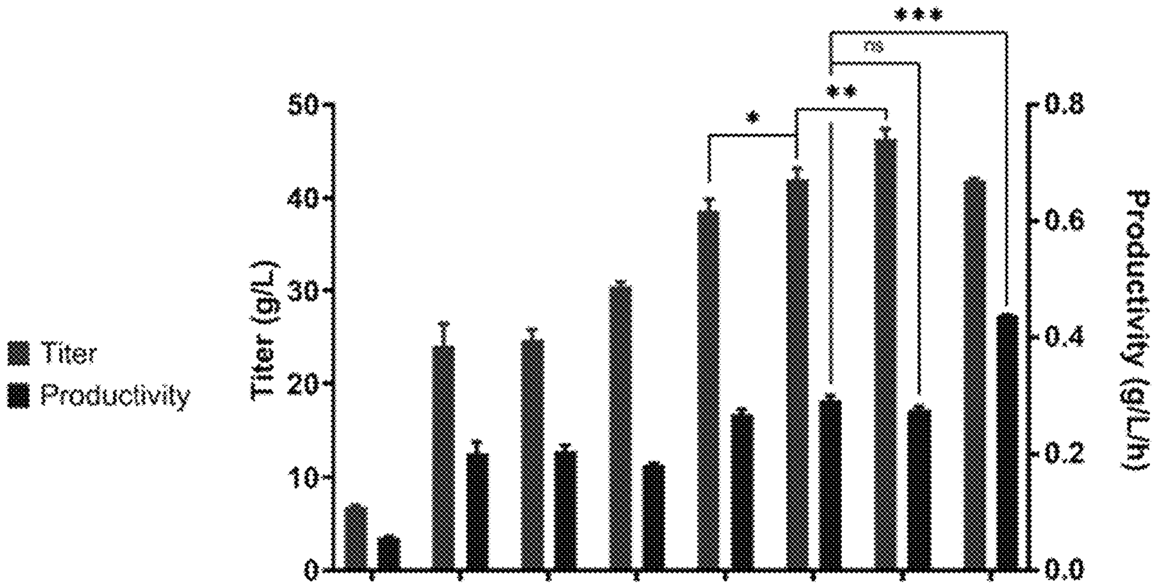
FIG. 1: Shows titers and productivities of engineered strains.
Figure 3:
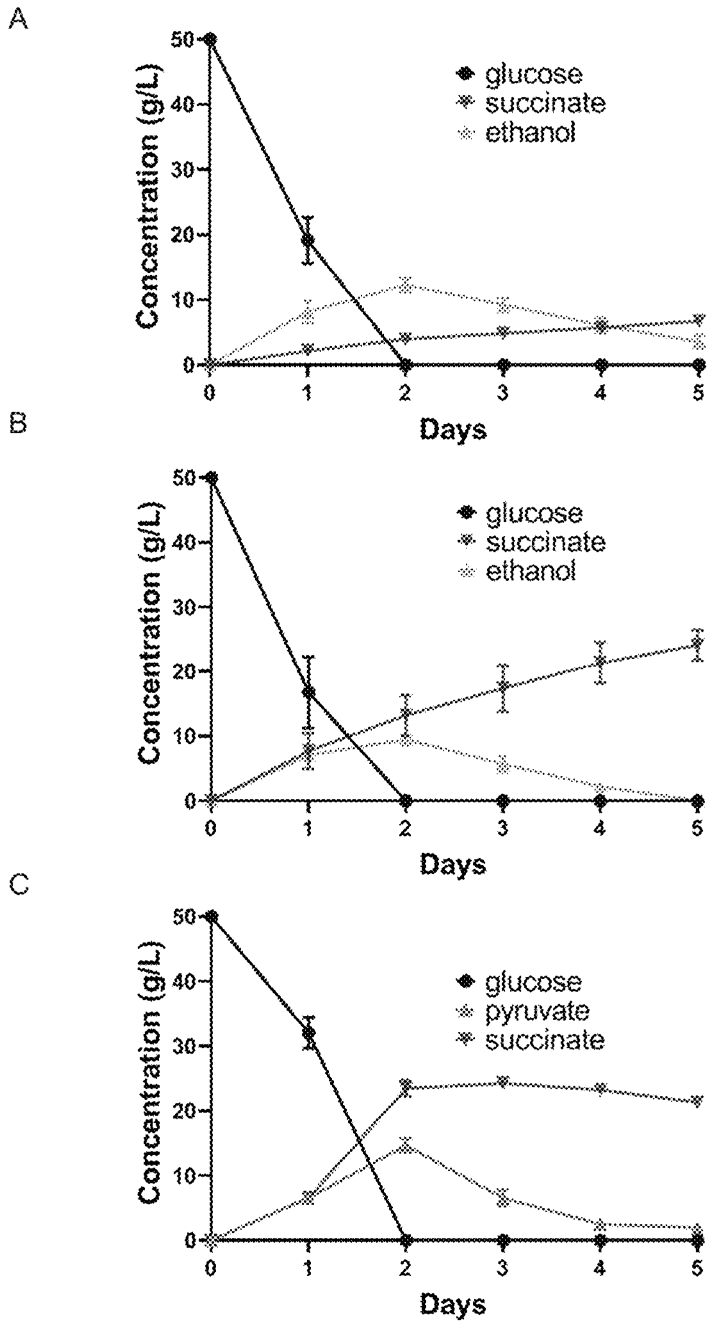
FIG. 3 Shows fermentation profiles of various strains in SC-URA medium with 50 g/L glucose under oxygen-limited condition in shake flasks. Panel (A) Fermentation of strain SA. Panel (B) Fermentation of strain SA/MAE1. Panel (C) Fermentation of strain SA/MAE1/pdcΔ/gpdA.

Example 1. Expression of a Dicarboxylic Acid Transporter and Deletion of by-Product Pathways We introduced a reductive tricarboxylic acid (rTCA) pathway into *I. orientalis* (strain SA) (FIG. 16*b*), enabling production of SA with a titer of 11.6 g/L in shake flask fermentations[13]. To further improve the titer, we attempted to express a transporter for SA. MAE1 from *Schizosaccharomyces pombe* (SpMAE1) was found to be the most efficient dicarboxylic acid transporter for export of SA[18]. The codon optimized SpMAE1 was integrated into the genome of strain SA, resulting in strain SA/MAE1. Strains SA and SA/MAE1 were evaluated for SA production using shake flask fermentations in SC-URA media with 50 g/L glucose under oxygen-limited conditions. The introduction of SpMAE1 greatly improved the SA titer from 6.8 g/L to 24.1 g/L (FIG. 1, FIGS. 3*a* and 3*b*).

Ethanol was the major byproduct and accumulated at 9.5 g/L in the fermentation of strain SA/MAE1. Ethanol is formed by the reaction catalyzed by alcohol dehydrogenase (ADH), which uses NADH to reduce acetaldehyde to ethanol. Since production of SA by the rTCA pathway requires NADH, eliminating the ethanol formation pathway might improve the SA production. Furthermore, although glycerol accumulated less than 1 g/L and was not the major byproduct observed in the fermentation of strain SA/MAE1, the glycerol formation pathway catalyzed by glycerol 3-phosphate dehydrogenase (GPD) can potentially compete with the rTCA pathway for carbon and NADH. Thus, both PDC (pyruvate decarboxylase) and GPD were deleted in strain SA/MAE1, resulting in strain SA/MAE1/pdcΔ/gpdΔ. While deletion of PDC to prevent ethanol formation should theoretically improve SA titer due to increase in availability of both pyruvate and NADH, fermentation of strain SA/MAE1/pdcΔ/gpdΔ unexpectedly resulted in the similar SA titer of 24.6 g/L and accumulation of 19.8 g/L pyruvate under oxygen-limited condition (FIG. 1 and FIG. 3*c*).

Figure 4:
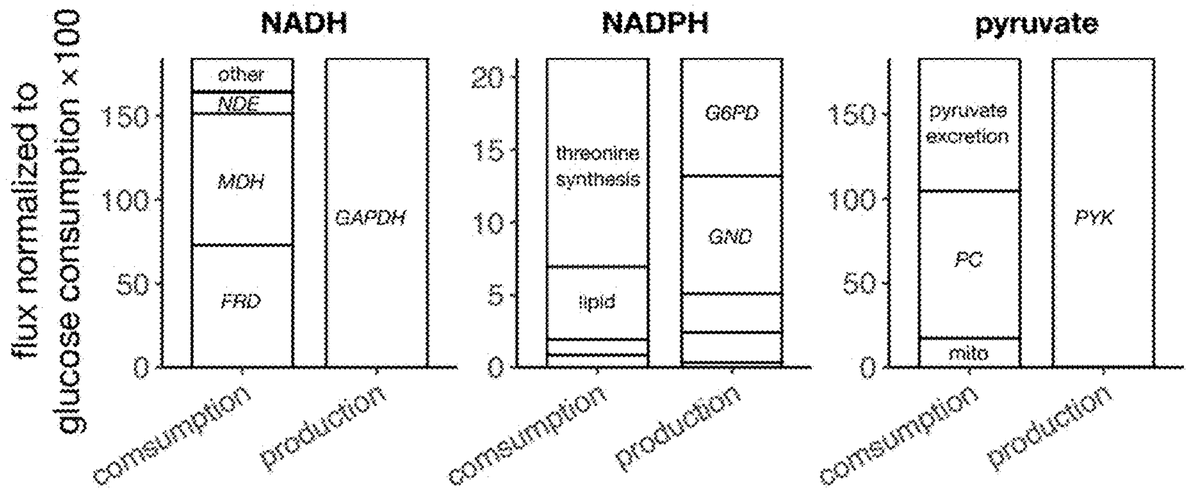
FIG. 4: Shows metabolic flux analysis of strain SA/MAE1/pdcΔ/gpdA.
Figure 5:
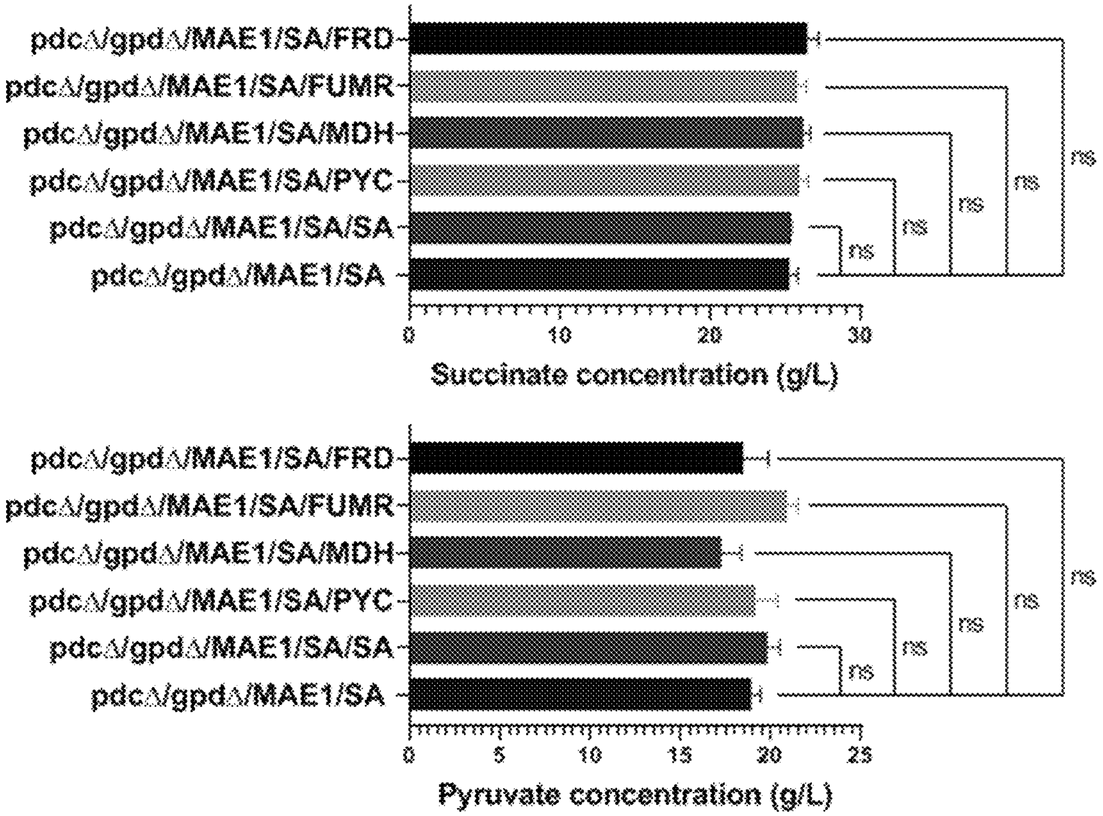
FIG. 5: Shows comparison of succinate and pyruvate titers between SA/MAE1/pdcΔ/gpdA and derived strains with one more copy of rTCA pathway or individual genes in the rTCA pathway.

A genome-scale model was constructed for *I. orientalis*, and all ADH activities were predicted to be localized in the mitochondrion19. Thus, removal of ethanol production through PDC deletion should not enhance cytosolic NADH availability, leading to no increase in SA titer. We conducted $^{13}C$ metabolic flux analysis (MFA) and verified that the rTCA pathway efficiently used most of the cytosolic NADH produced by glycolysis for SA production and pyruvate excretion accounted for half of the pyruvate produced from the last step of glycolysis (FIG. 4). We also expressed an additional copy of the rTCA pathway or individual gene of the rTCA pathway in strain SA/MAE1/pdcΔ/gpdΔ to further modulate the carbon fluxes between pyruvate and SA, but there was no significant change in SA titer or pyruvate accumulation (FIG. 5). Thus, the shortage of NADH supply in the cytosol is the main bottleneck for SA production through the rTCA cycle.

Example 2. Co-Fermentation of Glucose and Glycerol for SA Production

Figure 6:
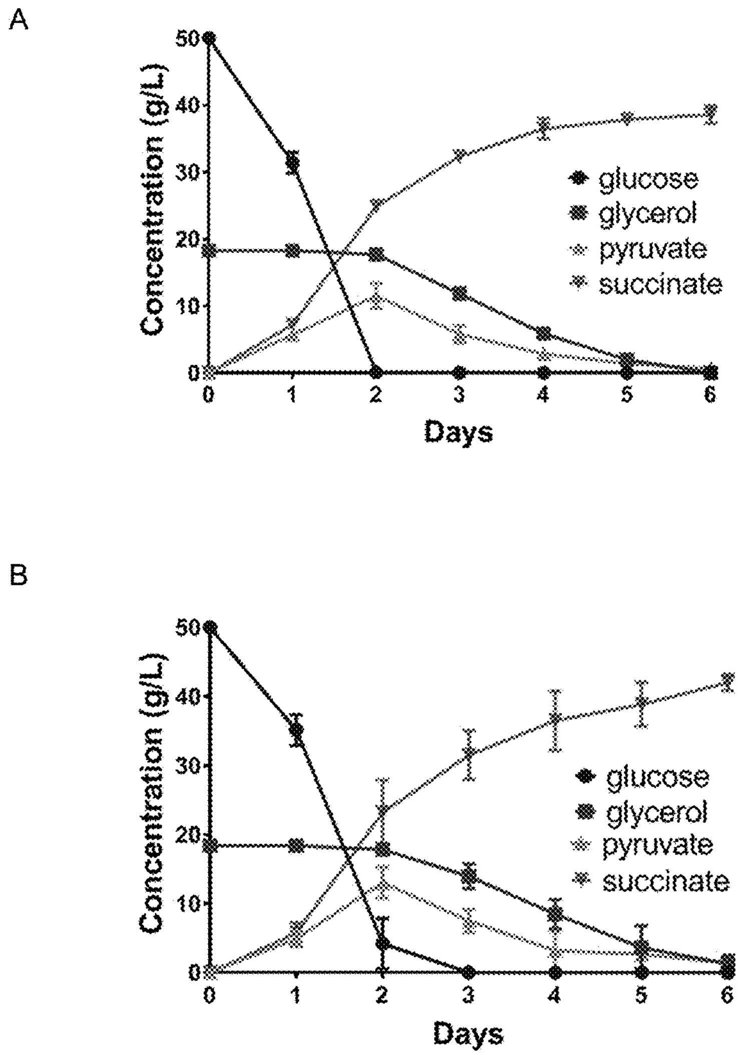
FIG. 6: shows fermentation profiles of strain SA/MAE1/pdcΔ/gpdA in SC-URA medium with 50 g/L glucose and 20 g/L glycerol in shake flasks. Panel (A) Oxygen-limited condition. Panel (B) Aerobic condition.

Since glucose alone does not produce sufficient cytosolic NADH for SA production, other carbon sources can be considered to obtain higher titers and yields. Glycerol is a cheap and readily available coproduct of biodiesel production and has higher degree of reduction than glucose. Conversion of 1 mole of glycerol to 1 mole of pyruvate through the DHA pathway generates 2 moles of NADH; thus, glycerol can produce more reducing equivalent NADH than glucose, which might be favorable for SA production. Since strain SA/MAE1/pdcΔ/gpdΔ exhibited growth defect in SC-URA medium with glycerol as the sole carbon source, we sought to perform fermentation of this strain using SC-URA medium with 50 g/L glucose and 20 g/L glycerol. Glucose and glycerol can be used as dual carbon sources and can enhance the conversion of oxaloacetate to malate through the increased supply of NADH from glycerol. As shown in FIG. 6*a*, the cells could consume both substrates for SA production under oxygen-limited conditions; however, glycerol consumption was slow, and the SA titer was improved to only 30.5 g/L after 7 days of fermentation. We then performed the fermentation under aerobic condition, postulating the glycerol metabolism might be limited at oxygen-limited condition. Under aerobic condition, both glucose and glycerol were consumed faster, allowing the production of 38.6 g/L of SA (FIG. 1 and FIG. 6*b*).

Figure 7:
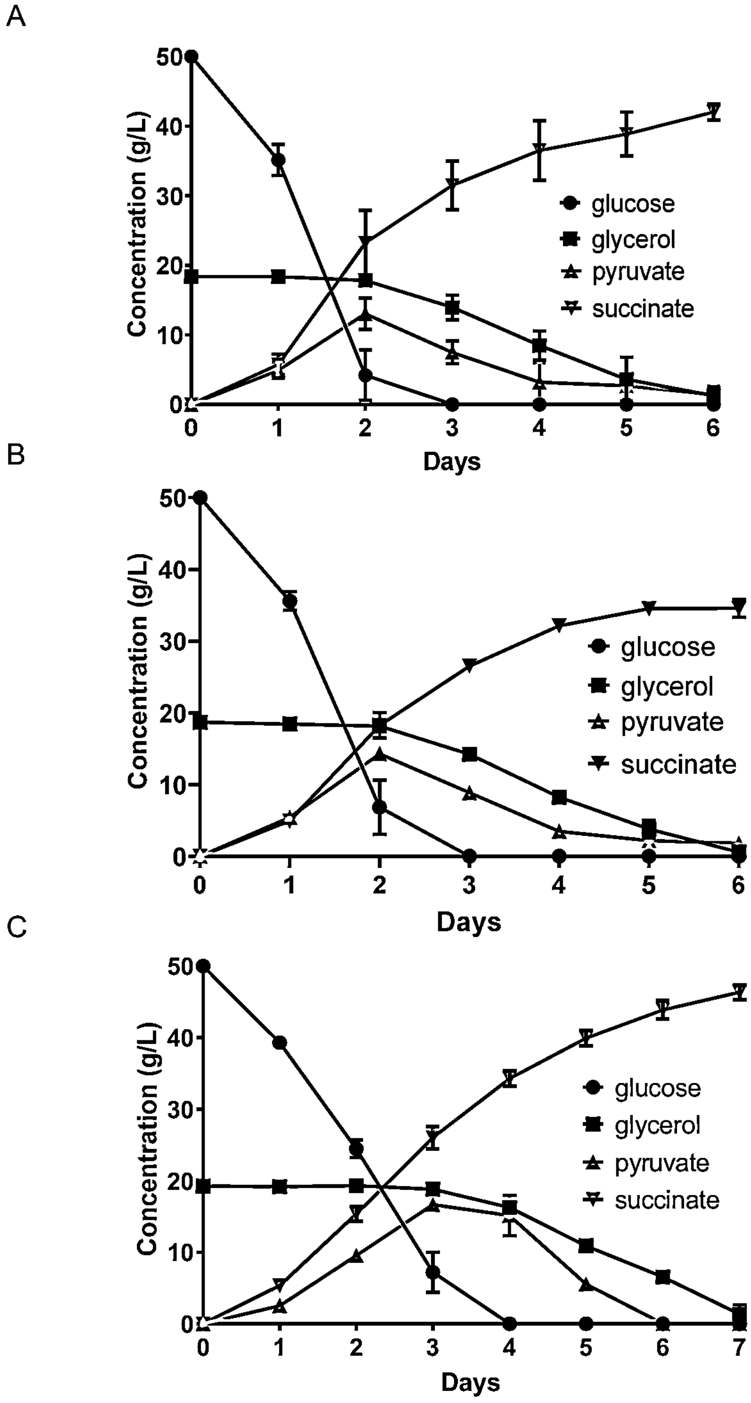
FIG. 7: Panel (A) Fermentation profile of strain g3473A. Panel (B) Fermentation profile of strain g3473Δ/g30684. Panel (C) Fermentation profile of strain g3473Δ/ndeA. All fermentations were performed in SC-URA medium with 50 g/L glucose and 20 g/L glycerol under aerobic condition in shake flasks.

Example 3. Deletions of a Dicarboxylic Acid Importer and External NADH Dehydrogenase Further gene deletions were then attempted to increase the SA production. Recently, the JEN family carboxylate transporters PKJEN2-1 and PKJEN2-2 in *Pichia kudriavzevii* were characterized to be involved in the inward uptake of dicarboxylic acids[2]. PKJEN2-1 and PKJEN2-2 were annotated as g3473 and g3068 in *I. orientalis*, respectively. g3473 was deleted from strain SA/MAE1/pdcΔ/gpdΔ, leading to strain g3473Δ. Fermentation of this strain in SC-URA medium with 50 g/L glucose and 20 g/L glycerol improved SA titer to 42.0 g/L (FIG. 1 and FIG. 7*a*), suggesting that preventing SA from re-entering the cells was beneficial. g3068 was further knocked out in strain g34734; however, we observed that disruption of both JEN2 transporters lowered the SA titer to 34.5 g/L and thus was not beneficial (FIG. 7*b*). This result was inconsistent with the previous report that deletion of both JEN transporters in P. kudriavzevii CY902 resulted in higher SA titer than single gene deletions, which might be attributed to different genetic backgrounds. P. kudriavzevii CY902 was engineered to produce SA using the oxidative TCA (OTCA) pathway by deletion of the succinate dehydrogenase complex subunit gene SDH5, while SA production in our engineered *I. orientalis* SD108 was achieved using the rTCA pathway. Moreover, based on MFA, a small amount of cytosolic NADH was oxidized by the external mitochondrial NADH dehydrogenase (NDE), which transports electrons from cytosolic NADH to the mitochondrial electron transport chain (FIG. 4). NDE was targeted for disruption in strain g34734, resulting in strain g3473Δ/ndeΔ. Compared to strain g3473Δ, NDE deletion further improved the SA titer to 46.4 g/L, suggesting knockout of NDE helped increase the cytosolic NADH pool for production of SA (FIG. 1 and FIG. 7*c*). Nevertheless, disruption of NDE lowered the glucose consumption rate; hence, despite having higher titer, strain g3473Δ/ndeΔ had similar productivity as strain g3473A (FIG. 1).

Example 4. Improving Glycerol Consumption

Figure 8:
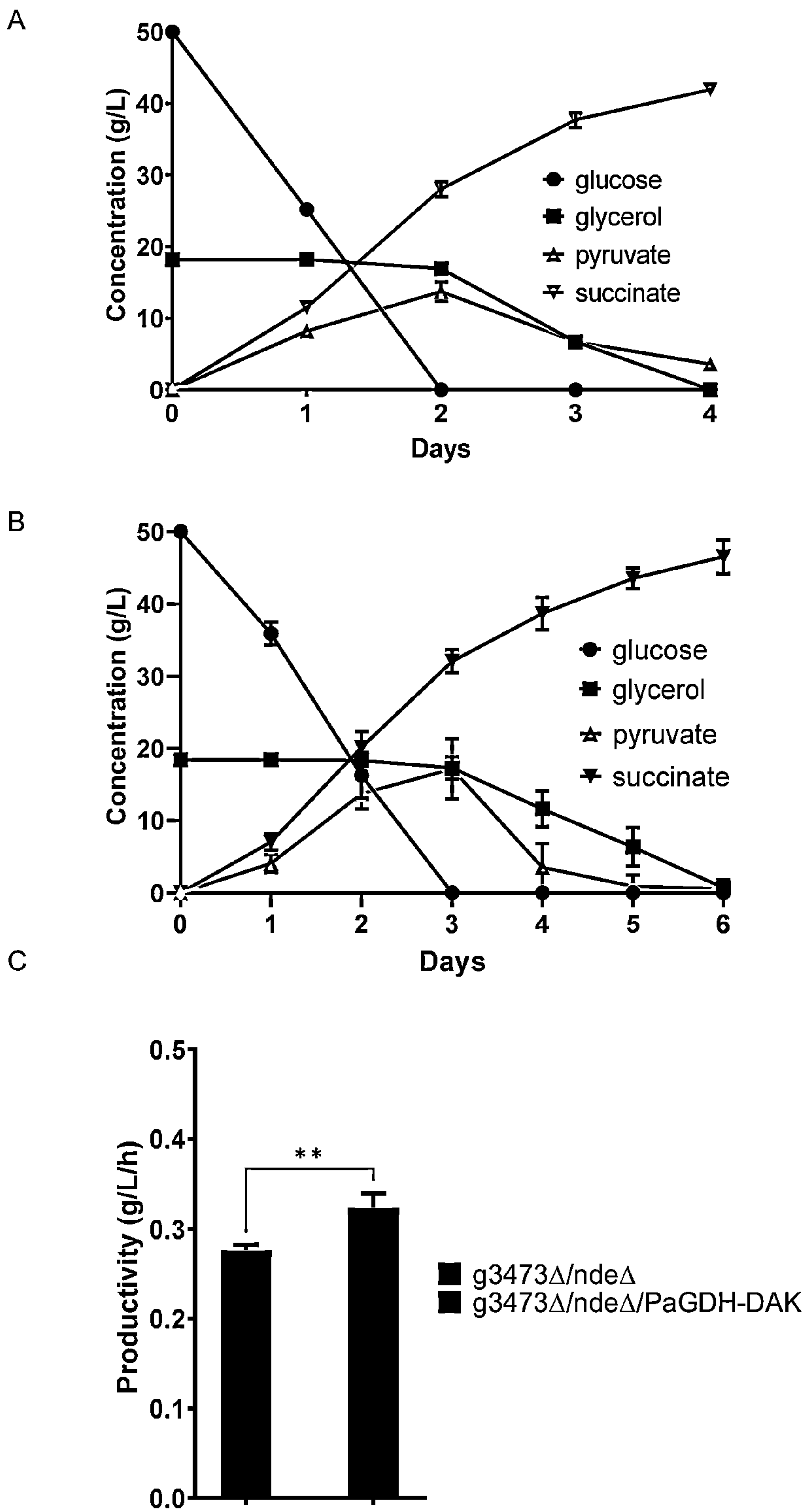
FIG. 8: Panel (A) Fermentation profile of strain g3473Δ/PaGDH-DAK. Panel (B) Fermentation profile of strain g3473Δ/ndeA/PaGDH-DAK. Panel (C) Comparison of productivities between g3473Δ/ndeA (left bar) and g3473Δ/ndeA/PaGDH-DAK (right bar). All fermentations were performed in SC-URA medium with 50 g/L glucose and 20 g/L glycerol under aerobic condition in shake flasks.

The slow glycerol consumption indicated the endogenous glycerol metabolism might not be highly active. Overexpression of GDH from *P. angusta* and endogenous DAK can be used to establish an NADH-producing glycerol consumption pathway. The codon optimized PaGDH and endogenous DAK were overexpressed in strains g34734 and g3473Δ/ndeΔ, resulting in strains g3473Δ/PaGDH-DAK and g3473Δ/ndeΔ/PaGDH-DAK, respectively. Fermentations of these strains in SC-URA medium with 50 g/L glucose and 20 g/L glycerol did not lead to higher titers of SA; g3473Δ/PaGDH-DAK and g3473Δ/ndeΔ/PaGDH-DAK produced SA at titers of 41.9 g/L and 46.5 g/L, respectively, similar to the titers achieved by the parent strains lacking the overexpression of PaGDH and DAK (FIG. 1, FIGS. 8*a* and *b*). Nevertheless, overexpression of PaGDH and DAK was beneficial to both glucose and glycerol utilization rates. The productivities were increased from 0.29 to 0.44 g/L/h in strain g3473Δ/PaGDH-DAK and from 0.28 to 0.32 g/L/h in strain g3473Δ/ndeΔ/PaGDH-DAK (FIG. 1 and FIG. 8*c*).

Figure 9:
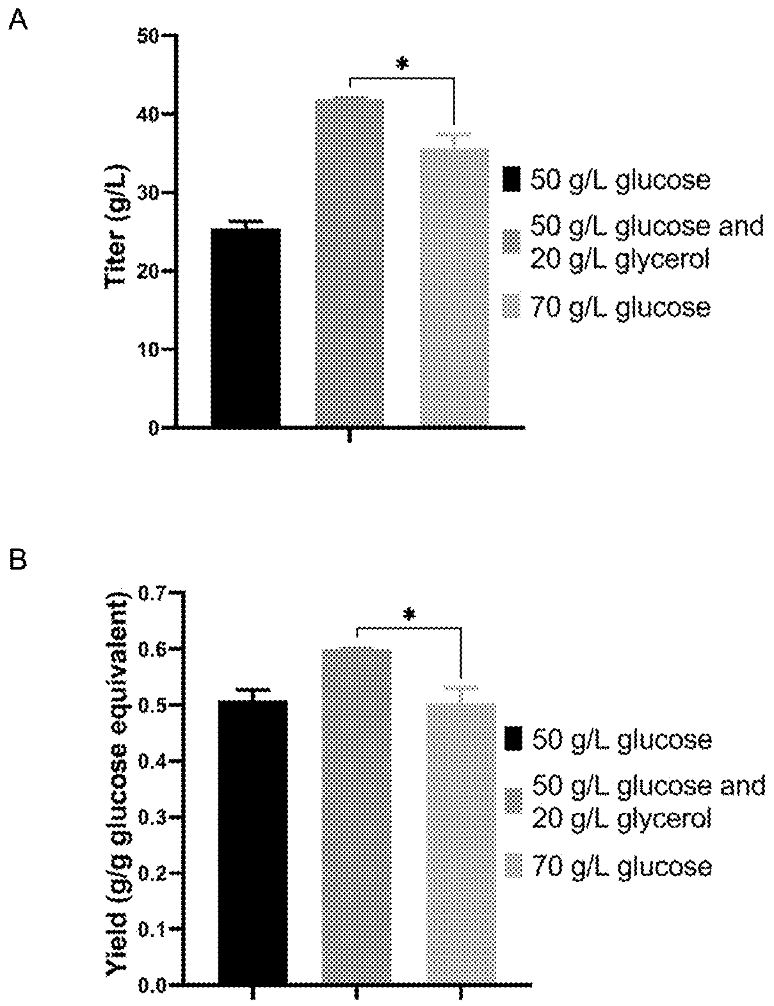
FIG. 9: Panel (A) Titer comparison between using only glucose and using both glucose and glycerol for production of SA. Panel (B) Yield comparison between using only glucose and using both glucose and glycerol for production of SA. All fermentations were performed using strain g3473Δ/PaGDH-DAK in SC-URA medium with 50 g/L glucose, 50 g/L glucose and 20 g/L glycerol, and 70 g/L glucose under aerobic condition in shake flasks.

Strain g3473Δ/PaGDH-DAK could produce up to 25 g/L of SA in fermentation using 50 g/L glucose, while 42.1 g/L of SA could be obtained from 50 g/L of glucose and 20 g/L of glycerol (FIG. 9*a*). Since the SA titer of 42.1 g/L could also be achieved just by simply using more initial glucose in the fermentation using only glucose, one may question the advantages of using glucose and glycerol as dual carbon sources. On a carbon equivalent basis, 1 gram of glucose is equivalent to 1 gram of glycerol. Using 50 g/L of glucose and 20 g/L of glycerol enabled the SA yield of 0.60 g/g glucose equivalent, which was higher than the yield of 0.51 g/g glucose from fermentation using only 50 g/L glucose (FIG. 9*b*). Furthermore, from 70 g/L of glucose, a concentration equivalent to 50 g/L of glucose and 20 g/L of glycerol, strain g3473Δ/PaGDH-DAK could produce SA at titer of only 35.6 g/L and yield of 0.50 g/g glucose (FIG. 9). Therefore, utilizing a mixture of glucose and glycerol as carbon sources allowed SA production at higher titer and higher yield than using equivalent amount of glucose.

Figure 10:
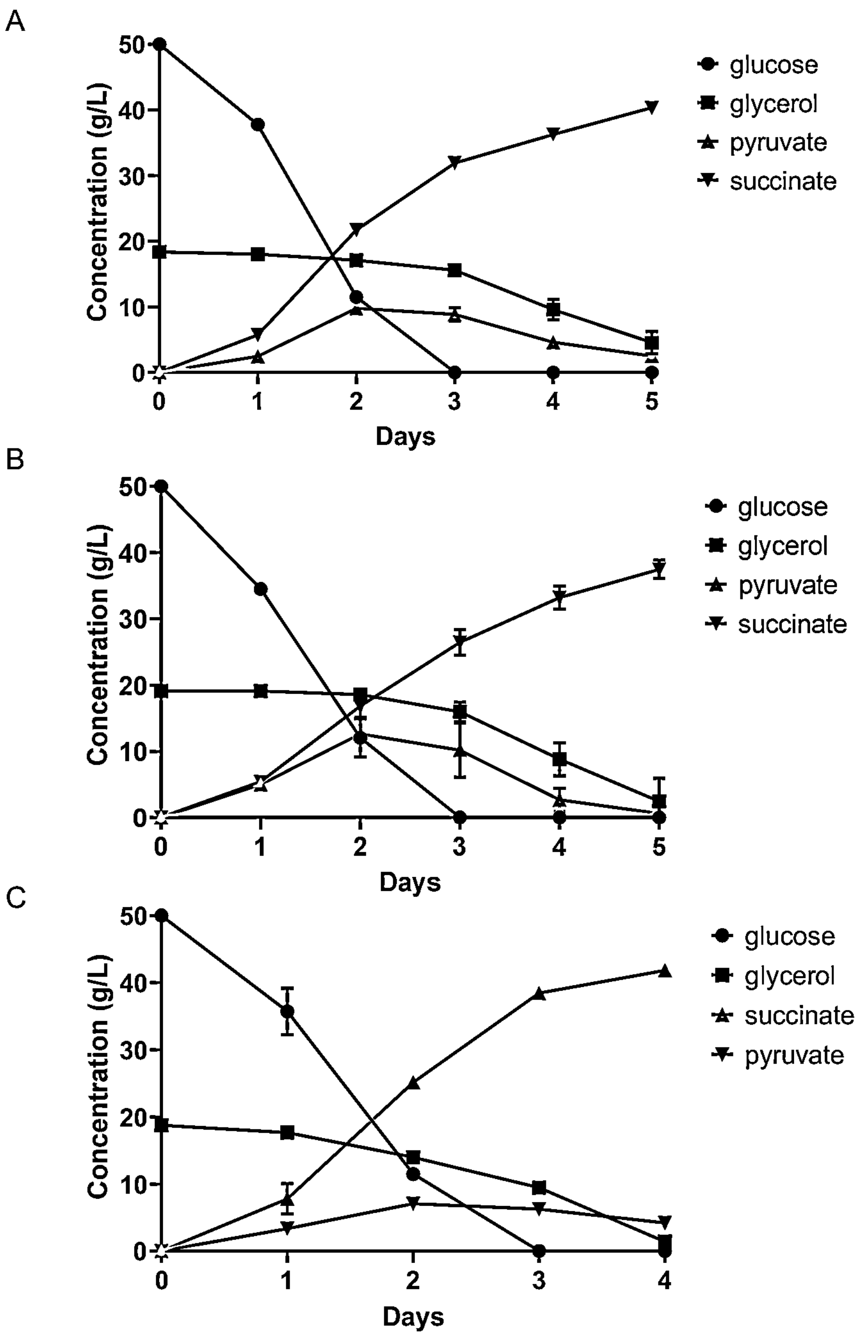
FIG. 10: Shows fermentation profiles in SC-URA medium with 50 g/L glucose and 20 g/L glycerol under aerobic condition in shake flasks. Panel (A) Strain g3473Δ/PaGDH-DAK with g1398 deletion. Panel (B) Strain g3473Δ/PaGDH-DAK with g2945 deletion. Panel (C) Strain g3473Δ/PaGDH-DAK with g3837 deletion.

We also attempted to relieve the catabolite repression of glucose on glycerol consumption through deletion of a hexokinase, which was shown to reduce glucose phosphorylation rate and permit co-utilization of glucose and xylose in *S. cerevisiae*[25]. Through BLAST analysis, three potential hexokinase genes (g1398, g2945, and g3837) were determined, and only deletion of g3837 in strain g3473Δ/PaGDH-DAK enabled simultaneous consumption of both glucose and glycerol (FIG. 10). While similar SA titers could be achieved, g3837 deletion lowered glucose and glycerol consumption rates, leading to no increase in productivity.

Example 5. Fed-Batch Fermentations and Scale-Up

Figure 11:
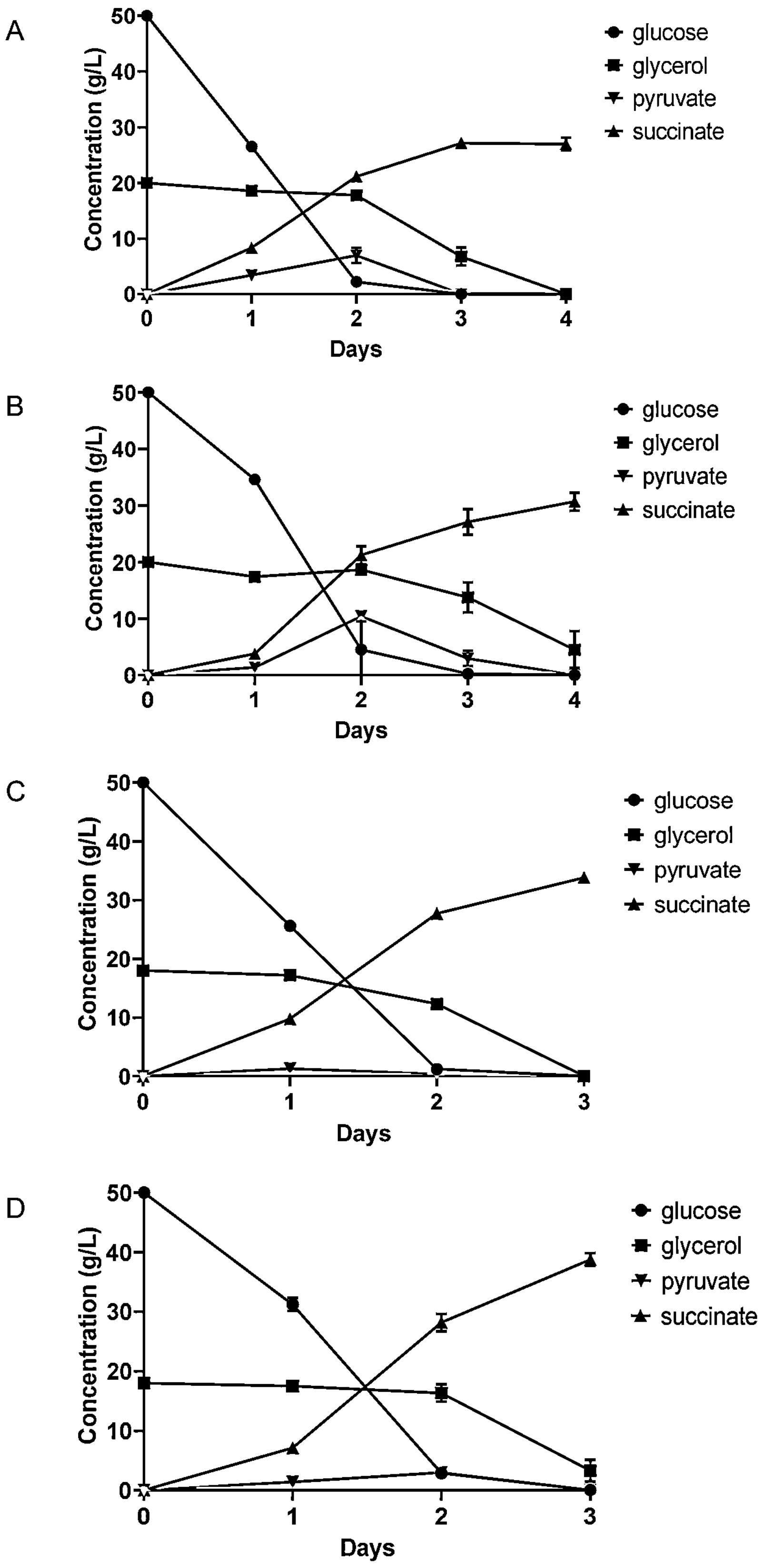
FIG. 11: Shows fermentation profiles in SC-URA medium with 50 g/L glucose and 20 g/L glycerol in bioreactors. Panel (A) Strain g3473Δ/PaGDH-DAK at 0.167 vvm $O_2$ and 0.333 vvm $CO_2$. Panel (B) Strain g3473Δ/PaGDH-DAK at 0.167 vvm 02 and 0.667 vvm $CO_2$. Panel (C) Strain g3473Δ/PaGDH-DAK/g3837A at 0.167 vvm 02 and 0.333 vvm $CO_2$. Panel (D) Strain g3473Δ/PaGDH-DAK/g3837A at 0.167 vvm 02 and 0.667 vvm $CO_2$.

Following shake flask fermentations, we performed fed-batch fermentations to increase the titer of SA and to assess the performance of our engineered strain in large scale production. To exploit the superior tolerance to low pH of *I. orientalis*, we chose to perform the fed-batch fermentation at pH 3. At this pH, approximately 90% of the SA species are fully protonated SA, while the remaining 10% of the species are hydrogen succinate[26]. We first tested the performance of strain g3473Δ/PaGDH-DAK, which was chosen over g3473Δ/ndeΔ/PaGDH-DAK due to higher productivity, using SC-URA medium with 50 g/L of glucose and 20 g/L of glycerol in batch fermentation in bench-top bioreactor with size of 0.3 L and working volume of 0.1 L under static conditions of agitation and continuous sparging of 02 and $CO_2$. We observed that the titers (27.1 g/L and 30.7 g/L at 0.333 vvm $CO_2$ and 0.667 vvm $CO_2$, respectively) were much lower than the titer obtained in shake flask fermentation (42.1 g/L) (FIGS. 11*a* and *b*). Particularly, while similar titers of SA could be produced from glucose in both reactor and shake flask, the SA titers produced during glycerol utilization phase were much lower in bioreactor. We also conducted batch fermentation in bioreactor using strain g3473Δ/PaGDH-DAK/g3837Δ and observed that this strain could produce more SA during glycerol consumption phase and a titer of 38.8 g/L of SA could be obtained at 0.167 vvm $O_2$ and 0.667 vvm $CO_2$ (FIGS. 11*c* and *d*). We postulated that while glycerol was being utilized in the bioreactor environment with higher aeration than shake flask environment, more carbon flux might be channeled to the TCA cycle and led to lower SA titer; on the other hand, deletion of g3837 might repress the activity of TCA cycle genes and improve SA production. Real-time PCR analysis was employed to compare the transcriptional levels of genes in the rTCA pathway and some selected genes in the TCA cycle (citrate synthase, CIT; aconitase, ACO; and isocitrate dehydrogenase, IDH) in strains g3473Δ/PaGDH-DAK with or without g3837 deletion grown in YP medium with glycerol.

Figure 2:
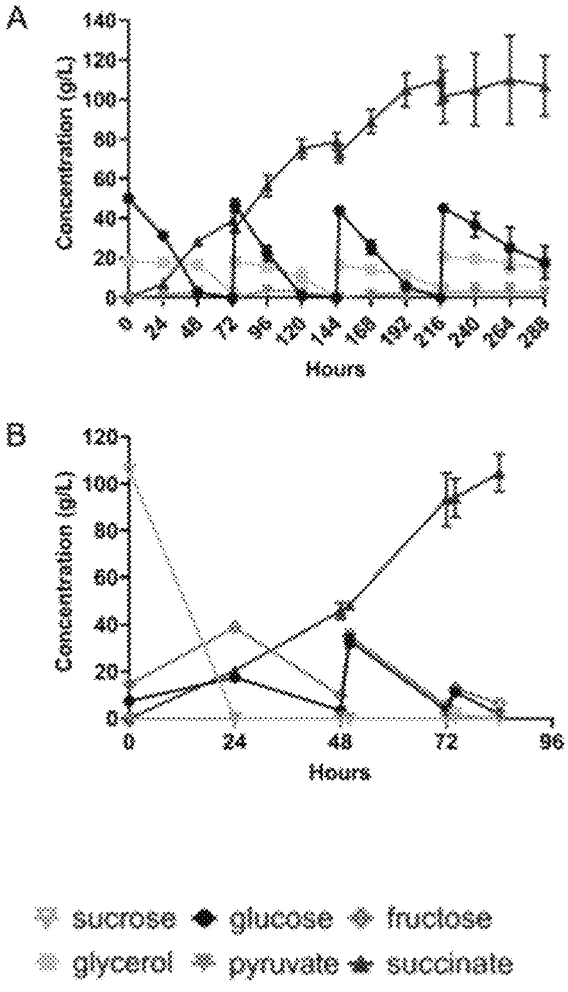
FIG. 2: Shows fermentations and recovery. Panel A. Fed-batch fermentation of strain g3473Δ/PaGDH-DAK/g3873A in minimal medium with glucose and glycerol. Panel B. Fed-batch fermentation of strain g3473Δ/PaGDH-DAK/ScSUC2 in sugarcane juice medium.
Figure 12:
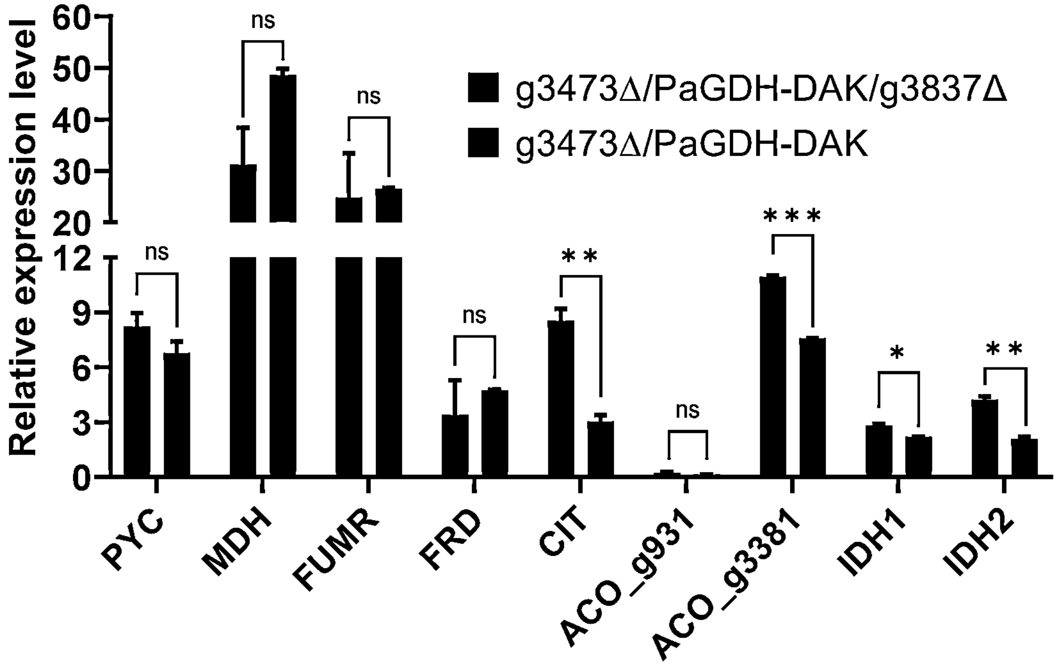
FIG. 12: shows qPCR analysis of expression levels of PYC, MDH, FUMR, FRD, CIT (citrate synthase), g931 and g3381 (aconitase), and IDH1 and IDH2 (isocitrate dehydrogenase) in strains g3473Δ/PaGDH-DAK and g3473Δ/PaGDH-DAK/g3837A. For each protein the left bar is g3473Δ/PaGDH-DAK/g3837A and the right bar is g3473Δ/PaGDH-DAK. Cells were grown in YP medium with glycerol as carbon source.
Figure 13:
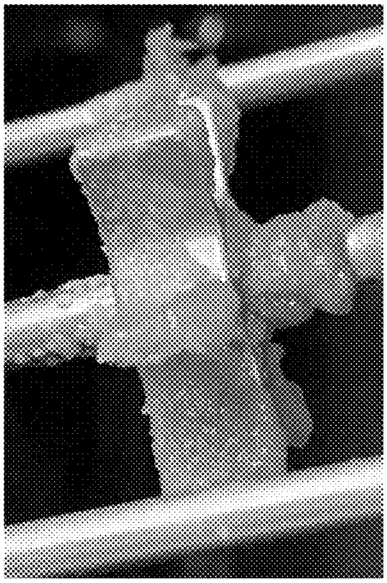
FIG. 13: Shows crystals after fed-batch fermentation using SC-URA medium.
Figure 14:
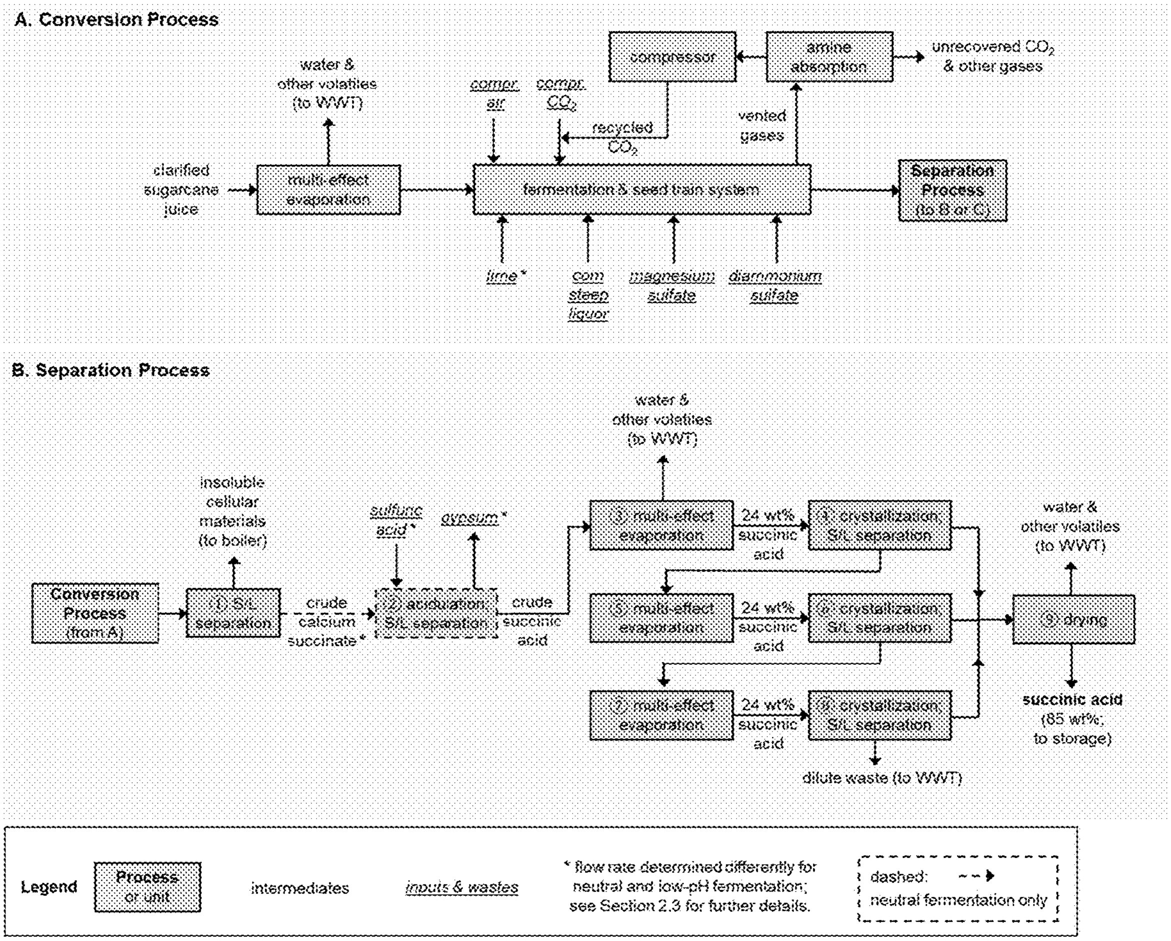
FIG. 14: Shows simplified block flow diagram of the designed biorefinery's Panel (A) conversion and Panel (B) separation processes. Acronyms denote compressed gas (compr.), wastewater treatment (WWT), and solid-liquid separation (S/L separation). A full process flowsheet is available online (BioSTEAM Development Group, 2023).
Figure 15:
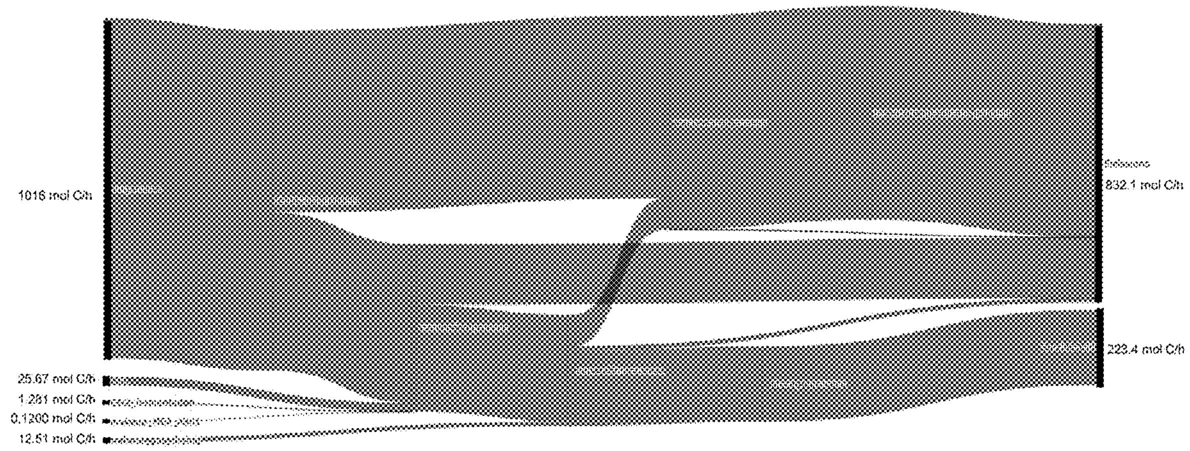
FIG. 15: Shows a Sankey diagram depicting the flow of carbon through the biorefinery for the pilot batch scenario.

We observed that knock out of g3837 maintained similar expressions of genes in the rTCA pathway but lowered the expression levels of CIT, a homolog of ACO, and IDHs (FIG. 12). Thus, the lower activities of genes in the TCA cycle might lead to higher SA titer obtained by strain g3473Δ/PaGDH-DAK/g3837Δ in bioreactor. The fed-batch fermentation of strain g3473Δ/PaGDH-DAK/g3837Δ in SC-URA medium with glucose and glycerol feeding produced 109.5 g/L of SA with yield of 0.65 g/g glucose equivalent and productivity of 0.54 g/L/h (FIG. 2*a*). At the end of the fermentation, we observed the formation of crystal, which was likely SA (FIG. 13). While other organic acids such as lactic and acetic acids are fully miscible in aqueous broth at pH 1-14, the solubility of SA decreases as the pH becomes more acidic[27].

Following the high fermentative performance of our recombinant *I. orientalis* strain using glucose and minimal SC-URA medium commonly used in the laboratory, we then tested the production of SA using a real industrial substrate, i.e. sugarcane juice. Sugarcane is the most energy efficient perennial C4 plant and has higher biomass yield compared to other crops such as switchgrass and *miscanthus*[28]. Furthermore, sugarcane juice, as a sucrose-based feedstock, is cheaper than glucose and starch-based substrates such as corn and cassava[29]. Since *I. orientalis* is unable to utilize sucrose, the invertase SUC2 from *S. cerevisiae* was expressed in g3473Δ/PaGDH-DAK.

In conclusion, by employing several metabolic engineering strategies, we have obtained an. *I. orientalis* strain that can produce more than 100 g/L of SA (at the maximum solubility of SA) using minimal media at low pH (pH 3). This is also the best overall performance to date for a yeast strain that used the carbon-fixing rTCA pathway. Furthermore, our TEA and LCA performed under uncertainty demonstrate that the currently achieved fermentation performance at the pilot scale enables an end-to-end bio-based SA production pathway that is more financially viable and far more environmentally beneficial than the fossil-based production pathway and highly competitive with other bio-based pathways. Overall, our study presents an end-to-end pipeline for economical production of SA from sugars at low pH.

Example 8. Materials and Methods

Strains, Media, and Materials

All strains used in this study are described in Table 1. *E. coli* DH5a was used to maintain and amplify plasmids and was grown in Luria Bertani medium (1% tryptone, 0.5% yeast extract, 1% NaCl) at 37° C. with ampicillin (100 μg/mL). *I. orientalis* SD108 and *S. cerevisiae* HZ848 were propagated at 30° C. in YPAD medium consisting of 1% yeast extract, 2% peptone, 0.01% adenine hemisulphate, and 2% glucose. Recombinant *I. orientalis* strains were cultured in Synthetic Complete (SC) dropout medium lacking uracil (SC-URA). Sugarcane juice medium was prepared by dissolving ammonium sulfate and magnesium sulfate at concentrations of 5 g/L and 1 g/L, respectively. LB broth, bacteriological grade agar, yeast extract, peptone, yeast nitrogen base (w/o amino acid and ammonium sulfate), and ammonium sulfate were purchased from Difco (BD, Sparks, MD), while complete synthetic medium was obtained from MP Biomedicals (Solon, OH). All restriction endonucleases and Q5 DNA polymerase were purchased from New England Biolabs (Ipswich, MA). QIAprep Spin Miniprep Kit was purchased from Qiagen (Valencia, CA), and Zymoclean Gel DNA Recovery Kit and Zymoprep Yeast Plasmid Miniprep Kits were purchased from Zymo Research (Irvine, CA). All other chemicals and consumables were purchased from Sigma (St. Louis, MO), VWR (Radnor, PA), and Fisher Scientific (Pittsburgh, PA). Oligonucleotides including gBlocks and primers were synthesized by Integrated DNA Technologies (IDT, Coralville, IA).

TABLE 1

Strains used in this study

| Strains | Features | Sources |
|---|---|---|
| *E. coli* DH5α | Cloning host | NEB |
| *S. cerevisiae* HZ848 | Host used for DNA assembly | Shao et al., 2009 |
| SD108/ura3Δ | *I. orientalis* SD108 with uracil autotrophy | Xiao et al., 2014 |
| SA | Io-ura3/ura3-::ura3-succinic acid biosynthetic pathway | Xiao et al., 2014 |
| SA/MAE1 | SD108 with overexpression of reductive TCA pathway and SpMAE1 | This study |
| SA/MAE1/pdcΔ/gpdΔ | SA/MAE1with GPD and PDC deletions | This study |
| SA/MAE1/pdcΔ/gpdΔ/X | SA/MAE1/pdcΔ/gpdΔ with overexpression of another copy of PYC, MDH, FUMR, FRD, or full reductive TCA pathway | This study |
| g3473Δ | SA/MAE1/pdcΔ/gpdΔ with g3473 deletion | |
| g3473Δ/g3068Δ | g3473Δ with g3068 deletion | This study |
| g3473Δ/ndeΔ | g3473Δ with NDE deletion | This study |
| g3473Δ/PaGDH-DAK | g3473Δ with overexpression of PaGDH and DAK | This study |
| g3473Δ/ndeΔ/ PaGDH-DAK | g3473Δ/ndeΔ with overexpression of PaGDH and DAK | This study |
| g3473Δ/PaGDH- DAK/ScSUC2 | g3473Δ/PaGDH-DAK with overexpression of ScSUC2 | This study |

Plasmids and Strains Construction

The plasmids, primers, gBlocks, and codon-optimized genes are listed in Tables 2, 3, 4, and 5, respectively. Genes were codon optimized and synthesized by Twist Bioscience (San Francisco, CA). Plasmids were generated by the DNA assembler method in *S. cerevisiae*[55], and Gibson assembly[56] and Golden Gate assembly[57] in *E. coli*. For DNA assembly, 100 ng of PCR-amplified fragments and restriction enzyme digested backbone were co-transformed into *S. cerevisiae* HZ848 via electroporation method. Transformants were plated on SC-URA plates and incubated at 30° C. for 48-72 hours. Yeast plasmids were isolated and transformed to *E. coli* for enrichment. *E. coli* plasmids were extracted and verified by restriction digestion. Details of strain construction procedures are described below. Lithium acetate-mediated method was used to transform yeast strains with plasmids and donor DNA fragments[58].

Construction of p102-MAE1: SpMAE1 was codon optimized and synthesized by TWIST and PCR-amplified using primers MAE1.F and MAE1.R. The amplified SpMAE1 was inserted into SfoI-digested p102 using HiFi DNA Assembly.

Construction of p101a-DAK: DAK was PCR-amplified from genomic DNA of SD108 using primers DAK.F and DAK.R. The amplified DAK was inserted into SfoI-digested p101a using HiFi DNA Assembly.

Construction of p102-PaGDH: PaGDH was codon optimized and synthesized by TWIST and PCR-amplified using primers PaGDH.F and PaGDH.R. The amplified PaGDH was inserted into SfoI-digested p102 using HiFi DNA Assembly.

Construction of p416-PaGDH-DAK: The cassette TDH3p-DAK-g3376t was PCR-amplified from plasmid p101a-DAK using primers p101a-DAK.F and p101a-DAK.R. The cassette g853p-PaGDH-g3767t was PCR-amplified from plasmid p102-PaGDH using primers p102-PaGDH.F and p102-PaGDH.F. Plasmid pRS416 was digested with XhoI and SacI. The cassettes TDH3p-DAK-g3376t and g853p-PaGDH-g3767t and the digested pRS416 were used for DNA assembler of pRS416-PaGDH-DAK.

Construction of p101a-CjFPS1: SpMAE1 was codon optimized and synthesized by TWIST and PCR-amplified using primers MAE1.F and MAE1.R. The amplified SpMAE1 was inserted into SfoI-digested p102 using HiFi DNA Assembly.

Construction of p101a-YIFPS1: SpMAE1 was codon optimized and synthesized by TWIST and PCR-amplified using primers MAE1.F and MAE1.R. The amplified SpMAE1 was inserted into SfoI-digested p102 using HiFi DNA Assembly. Construction of p101a-SUC2: SpMAE1 was codon optimized and synthesized by TWIST and PCR-amplified using primers MAE1.F and MAE1.R. The amplified SpMAE1 was inserted into SfoI-digested p102 using HiFi DNA Assembly.

Construction of pVT36b-PDC, pVT36b-GPD, pVT36b-g3473, pVT36b-g3068, and pVT36b-NDE: The gBlocks PDC, GPD, g3473, g3068, and NDE were inserted into pVT36b using Golden Gate Assembly with BsaI.

Construction of pVT36b-int1, pVT36b-int2, pVT36b-int3, and pVT36b-int5: Primers site[1].spacer.R and site[1].spacer.R were annealed using T4 Polynucleotide Kinase, and the product was then inserted into pVT36b using Golden Gate Assembly with BsaI to construct pVT36b.int1. Construction of pVT36b-int2, pVT36b-int3, and pVT36b-int5 were done similarly using the corresponding primer pairs.

Construction of strain SA/MAE1: The cassette g853p-SpMAE1-g3767t was PCR-amplified from plasmid p102-MAE1 and co-transformed with pVT36b-int2 into SD108. Yeast colonies were screened for integration of g853p-SpMAE1-g3767t cassette by PCR using primers MAE1.check.F and int2.down.R. Plasmid pVT36b-int2 was then cured using SC-FOA, leading to strain MAE1/ura3Δ.

Plasmid pRS416-SA-site[1] was digested with MluI to liberate the reductive TCA cassette. The reductive TCA cassette was co-transformed with pVT36b-int1 into MAE1/ura3Δ. Yeast colonies were screened for integration of reductive TCA cassette by PCR using primers SA.check.F and int1.down.R. Plasmid pVT36b-int1 was then cured using SC-FOA, resulting in strain SA/MAE1/ura3Δ. Uracil prototrophy was restored by integration of URA3p-URA3-PDC1t cassette, amplified using primers URA3.F and URA3.R from p101a, to strain SA/MAE1/ura3Δ, leading to strain SA/MAE1.

Construction of strain SA/MAE1/pdcΔ/gpdΔ: For PDC deletion, plasmid pVT36b-PDC was transformed into SA/MAE1/ura3Δ. For verification of deletion, the PDC was PCR-amplified using primers PDC.check.F and PDC.check.R from genomic DNA, and the PCR product was digested with EcoRI. Successful deletion of PDC resulted in 2 bands on the agarose gel. Plasmid pVT36b-PDC was then cured using SC-FOA, resulting in strain SA/MAE1/pdcΔ/ura3Δ. For GPD deletion, plasmid pVT36b-GPD was transformed into SA/MAE1/pdcΔ/ura3Δ. For verification of deletion, the GPD was PCR-amplified using primers GPD.check.F and GPD.check.R from genomic DNA, and the PCR product was digested with EcoRI. Successful deletion of GPD resulted in 2 bands on the agarose gel. Plasmid pVT36b-GPD was then cured using SC-FOA, resulting in strain SA/MAE1/pdcΔ/gpdΔ/ura3Δ. Uracil prototrophy was restored by integration of URA3p-URA3-PDC1t cassette, amplified using primers URA3.F and URA3.R from p101a, to strain SA/MAE1/pdcΔ/gpdΔ/ura3Δ, leading to strain SA/MAE1/pdcΔ/gpdΔ.

Construction strain g3473Δ: Plasmid pVT36b-g3473 was transformed into SA/MAE1/pdcΔ/gpdΔ/ura3Δ. For verification of deletion, g3473 was PCR-amplified from genomic DNA, and the PCR product was digested with XhoI. Successful deletion of g3473 resulted in 2 bands on the agarose gel. Plasmid pVT36b-GPD was then cured using SC-FOA, resulting in strain g3473Δ/ura3Δ. Uracil prototrophy was restored by integration of URA3p-URA3-PDC1t cassette, amplified using primers URA3.F and URA3.R from p101a, to strain g3473Δ/ura3Δ, leading to strain g34734.

Construction of strain g3473Δ/g3068A: Plasmid pVT36b-g3068 was transformed into g3473Δ. For verification of deletion, g3068 was PCR-amplified from genomic DNA, and the PCR product was digested with XhoI. Successful deletion of g3068 resulted in 2 bands on the agarose gel. Plasmid pVT36b-g3068 was then cured using SC-FOA, resulting in strain g3473Δ/g3068Δ/ura3Δ. Uracil prototrophy was restored by integration of URA3p-URA3-PDC1t cassette, amplified using primers URA3.F and URA3.R from p101a, to strain g3473Δ/g3068Δ/ura34, leading to strain g3473Δ/g30684.

Construction of strain g3473Δ/ndeΔ: Plasmid pVT36b-NDE was transformed into g3473Δ. For verification of deletion, NDE was PCR-amplified from genomic DNA, and the PCR product was digested with XhoI. Successful deletion of NDE resulted in 2 bands on the agarose gel. Plasmid pVT36b-NDE was then cured using SC-FOA, resulting in strain g3473Δ/ndeΔ/ura3Δ. Uracil prototrophy was restored by integration of URA3p-URA3-PDC1t cassette, amplified using primers URA3.F and URA3.R from p101a, to strain g3473Δ/ndeΔ/ura3Δ, leading to strain g3473Δ/ndeΔ.

Construction of strain g3473Δ/PaGDH-DAK: The cassette TDH3p-DAK-g3376t-g853p-PaGDH-g3767t was PCR amplified using primers glycerol.int3.F and glycerol.int3.R and co-transformed with pVT36b-int3 into g3473Δ. Yeast colonies were screened for integration of TDH3p-DAK-g3376t-g853p-PaGDH-g3767t cassette by PCR using primers glycerol.check.F and int3.down.R. Plasmid pVT36b-int3 was then cured using SC-FOA, leading to strain g3473Δ/PaGDH-DAK/ura3Δ. Uracil prototrophy was restored by integration of URA3p-URA3-PDC1t cassette, amplified using primers URA3.F and URA3.R from p101a, to strain g3473Δ/PaGDH-DAK/ura3Δ, leading to strain g3473Δ/PaGDH-DAK.

Construction of strain g3473Δ/ndeΔ/PaGDH-DAK: The cassette TDH3p-DAK-g3376t-g853p-PaGDH-g3767t was PCR amplified using primers glycerol.int3.F and glycerol.int3.R and co-transformed with pVT36b-int3 into g3473Δ/ndeΔ. Yeast colonies were screened for integration of TDH3p-DAK-g3376t-g853p-PaGDH-g3767t cassette by PCR using primers glycerol.check.F and int3.down.R. Plasmid pVT36b-int3 was then cured using SC-FOA, leading to strain g3473Δ/ndeΔ/PaGDH-DAK/ura3Δ. Uracil prototrophy was restored by integration of URA3p-URA3-PDC1t cassette, amplified using primers URA3.F and URA3.R from p101a, to strain g3473Δ/ndeΔ/PaGDH-DAK/ura3Δ, leading to strain g3473Δ/ndeΔ/PaGDH-DAK.

Construction of strain g3473Δ/PaGDH-DAK/CjFPS1: The cassette URA3p-URA3-PDC1t-TDH3p-CjFPS1-g3376t was PCR amplified using primers URA3.F and URA3.R from p101a-CjFPS1 and transformed into g3473Δ/

PaGDH-DAK, leading to strain g3473Δ/PaGDH-DAK/CjFPS1. Construction of strain g3473Δ/PaGDH-DAK/YIFPS1: The cassette URA3p-URA3-PDC1t-TDH3p-YIFPS1-g3376t was PCR amplified using primers URA3.F and URA3.R from p101a-YIFPS1 and transformed into g3473Δ/PaGDH-DAK, leading to strain g3473Δ/PaGDH-DAK/YIFPS1.

Construction of g3473Δ/PaGDH-DAK/ScSUC2: The cassette TDH3p-ScSUC2-g3376t was PCR amplified using primers p101a.int5.F and p101a.int5.R and co-transformed with pVT36b-int5 into g3473Δ/PaGDH-DAK/ura3Δ. Yeast colonies were screened for integration of TDH3p-ScSUC2-g3376t cassette by PCR using primers SUC2.check. F and int5.down.R. Plasmid PVT36b-int5 was then cured using SC-FOA, leading to strain g3473Δ/PaGDH-DAK/ScSUC2/ura3Δ. Uracil prototrophy was restored by integration of URA3p-URA3-PDC1t cassette, amplified using primers URA3.F and URA3.R from p101a, to strain g3473Δ/PaGDH-DAK/ScSUC2/ura3Δ, leading to strain g3473Δ/PaGDH-DAK/ScSUC2.

TABLE 2

Plasmids used in this study

| Plasmids | Features | Sources |
|---|---|---|
| pRS416 | *S. cerevisiae* plasmid containing URA3 marker and ARS/CEN | NEB |
| pVT36b | *I. orientalis* plasmid for gene deletion | Tran et al., 2019 |
| pRS415-E | pRS415 with URA3, PYC, MDH, FUMR and FRD expression cassettes added | Xiao et al., 2014 |
| p101a | Helper plasmid to clone genes into the TDH3p-g3376t cassette; constructed by DNA assembler | This study |

TABLE 2-continued

Plasmids used in this study

| Plasmids | Features | Sources |
|---|---|---|
| p102 | Helper plasmid to clone genes into the g853p-g3767t cassette; constructed by DNA assembler | This study |
| pRS416-SA-site1 | pRS416 harboring reductive TCA pathway flanked with homology arms for integration to site 1; constructed by DNA assembler | This study |
| p102-MAE1 | p102 with SpMAE1 insertion | This study |
| p101a-DAK | p101a with DAK insertion | This study |
| p102-PaGDH | p102 with PaGDH insertion | This study |
| p416-PaGDH-DAK | pRS416 harboring TDH3p-DAK-g3376t and g853p-PaGDH-g3767t cassettes; constructed by DNA assembler | This study |
| p101a-SUC2 | p101a with ScSUC2 insertion | This study |
| pVT36b-PDC | pVT36b with insertion of gBlock for PDC deletion | This study |
| pVT36b-GPD | pVT36b with insertion of gBlock for GPD deletion | This study |
| pVT36b-g3473 | pVT36b with insertion of gBlock for g3473 deletion | This study |
| pVT36b-g3068 | pVT36b with insertion of gBlock for g3068 deletion | This study |
| pVT36b-NDE | pVT36b with insertion of gBlock for NDE deletion | This study |
| pVT36b-int1 | pVT36b with insertion of spacer for integration at site 1 | This study |
| pVT36b-int2 | pVT36b with insertion of spacer for integration at site 2 | This study |
| pVT36b-int3 | pVT36b with insertion of spacer for integration at site 3 | This study |
| pVT36b-int5 | pVT36b with insertion of spacer for integration at site 5 | This study |

TABLE 3

Primers used in this study

| Primers | Sequences (5' to 3') | Sequence ID Number |
|---|---|---|
| MAE1.F | ATCTTAAAACACACACACAAAATGGGCGAGTTGAAAGAG | SEQ ID NO: 1 |
| MAE1.R | TATAGTTCGCCTCAGAATCTAGACGGACTCGTGCTC | SEQ ID NO: 2 |
| p102.site2.F | TCTTAAAAATATTGAACCGTCGAAACGTCCCAAACAAGGAAACGAAAAATGCACC ACACC | SEQ ID NO: 3 |
| p102.site2.R | AAAGGTGAGAATTCAAAATGTTATTTTTGATCATGTAAAGGGTAGCACGTGATGA AAAGG | SEQ ID NO: 4 |
| DAK.F | ACAAACAAACACAATTACAAAAAATGTCACAAGAAAAACATTGG | SEQ ID NO: 5 |
| DAK.R | GAACAAACATCTTGTTGTAGTTACGATTGGTATGCACTG | SEQ ID NO: 6 |
| PaGDH.F | TCTTAAAACACACACACAAAATGAAAGGTTTACTTTACTATGG | SEQ ID NO: 7 |
| PaGDH.R | TATAGTTCGCCTCAGAATCTAACTTACTTCATTGGGC | SEQ ID NO: 8 |
| p101a-DAK.F | CTGTGTAGTTAATTGAATTCTTAAGTTTCTTGATTTAACCTGATCCAAAAG | SEQ ID NO: 9 |
| p101a-DAK.R | CCAAGCGCGCAATTAACCCTCACTAAAGGGAACAAAAGCTGGTATCTGTCAACAA CGTAC | SEQ ID NO: 10 |
| p102-PaGDH.F | AATACGACTCACTATAGGGCGAATTGGGTACCGGGCCCCCCCCGAAAAATGCACC ACACC | SEQ ID NO: 11 |
| p102-PaGDH.R | GACATACCCCTTTTGGATCAGGTTAAATCAAGAAACTTAAGAATTCAATTAACTA CACAG | SEQ ID NO: 12 |

TABLE 3-continued

| Primers used in this study | | |
|---|---|---|
| Primers | Sequences (5' to 3') | Sequence ID Number |
| glycerol.int3.F | ATTCTTGTACAGCTTTGATGCGAGCATTAATAAGAAAGAAACTAGGGCGAATTGG GTACC | SEQ ID NO: 13 |
| glycerol.int3.R | GAGGATATTAATGGTACTTAAGAATAGTTGAATAGATATATGCATGATTACGCCA AGCGC | SEQ ID NO: 14 |
| SUC2.F | ACAAACAAACACAATTACAAAAAATGCTTTTGCAAGCTTTC | SEQ ID NO: 15 |
| SUC2.R | GAACAAACATCTTGTTGTAGCTATTTTACTTCCCTTACTTGG | SEQ ID NO: 16 |
| p101a.int5.F | TTATAAAAACTGATAAACCATGAGAGTGTACCGATAAGTAAACGGATCCTTGATT TAACC | SEQ ID NO: 17 |
| p101a.int5.R | ATTTTACCTTTTACAAATTACATCAAAAGGTTAATTTCTCTCTATCTGTCAACAA CGTAC | SEQ ID NO: 18 |
| CjFPS1.F | ACAAACAAACACAATTACAAAAAATGACAGGAGAATTACTTGCTAGTG | SEQ ID NO: 19 |
| CjFPS1.R | GAACAAACATCTTGTTGTAGTCAAGCGTCAAGACGACC | SEQ ID NO: 20 |
| YIFPS1.F | ACAAACAAACACAATTACAAAAAATGCTCAACCAGCCGAAAAAACC | SEQ ID NO: 21 |
| YIFPS1.R | GAACAAACATCTTGTTGTAGCTAACTACTGTCCGAGTCGTCG | SEQ ID NO: 22 |
| URA3.F | ACGCGTAAACAGGGAAGG | SEQ ID NO: 23 |
| URA3.R | ACGCGTAACACTTAGAATACG | SEQ ID NO: 24 |
| PDC.check.F | CATTGTTGGACCACGTCAAGG | SEQ ID NO: 25 |
| PDC.check.R | AACGAGAATGATTGGTTTTTCTG | SEQ ID NO: 26 |
| GPD.check.F | CCCCTGCTGAAAGATTATCTAC | SEQ ID NO: 27 |
| GPD.check.R | AATTAGCACCTGATAAGGCAC | SEQ ID NO: 28 |
| g3473.check.F | ATGACTTTACACAAAAATTCCAACG | SEQ ID NO: 29 |
| g3473.check.R | GGGAATTATCAGCAATTGCTC | SEQ ID NO: 30 |
| g3068.check.F | ATGTCTGATTTAGAGTCACAAC | SEQ ID NO: 31 |
| g3068.check.R | CTCTCCACTTATGTGACG | SEQ ID NO: 32 |
| NDE.check.F | GAGGTGACTTATTTAGAAGC | SEQ ID NO: 33 |
| NDE.check.R | ATTTCCTTTGAGCGTTACC | SEQ ID NO: 34 |
| int1.down.R | GAAATGCCAAGTGTTTGAGC | SEQ ID NO: 35 |
| int2.down.R | GCTGGTCTATAATAAATAGGG | SEQ ID NO: 36 |
| int3.down.R | ACTTTCTGTAACACCGTTTC | SEQ ID NO: 37 |
| int5.down.R | TAATCAAGAAAAGACAATGACC | SEQ ID NO: 38 |
| MAE1.check.F | CCAGCTTCGTTAGAGAAGG | SEQ ID NO: 39 SpMAE1 portion |
| SA.check.F | TAGGGTATAACATGAACTTGG | SEQ ID NO: 40 |
| glycerol.check.F | GAGGAATTTAGAAGATTTGACAG | SEQ ID NO: 41 |
| SUC2.check.F | GTTCTACATTGACAAGTTCC | SEQ ID NO: 42 |
| site1.spacer.F | TGCAAAGCGATAGTCTGTTTTGTC | SEQ ID NO: 43 |
| site1.spacer.R | AAACGACAAAACAGACTATCGCTT | SEQ ID NO: 44 |
| site2.spacer.F | TGCATAATTTCAACACCTTACTCC | SEQ ID NO: 45 |
| site2.spacer.R | AAACGGAGTAAGGTGTTGAAATTA | SEQ ID NO: 46 |
| site3.spacer.F | TGCATAAACACTAAGTTTCAAGCC | SEQ ID NO: 47 |

TABLE 3-continued

| Primers used in this study | | |
|---|---|---|
| Primers | Sequences (5' to 3') | Sequence ID Number |
| site3.spacer.R | AAACGGCTTGAAACTTAGTGTTTA | SEQ ID NO: 48 |
| site5.spacer.F | TGCATTAGACAGAATGAAGGCACC | SEQ ID NO: 49 |
| site5.spacer.R | AAACGGTGCCTTCATTCTGTCTAA | SEQ ID NO: 50 |

TABLE 4

| gBlocks | gBlocks used in this Sequences (5' to 3') | Sequence ID Number |
|---|---|---|
| PDC ri | CTTTGGTCTCCTGCATCAGCATAAGAACCTGCAATGGCATTGACGGCAGACAATTCACCGACACC<br>GAATTCTGATTAGGGATGCAAATCCATTGATTCTTGCATAACCATCAGCTTCGTAGCAATTCACC<br>GACACCAAAGGGTTTGGAGACCTTTC | SEQ ID NO: 70 |
| GPD ri | CTTTGGTCTCCTGCAAAGACTATCCGGAACATCCGTTCAAGGTGACGGTTGTTGGTTCCGGTAAC<br>GAATTCGTACAATTGCCAAGGTTATAGCGGAAAACACCGTTGAGAGACCTCGTCAATTGTTGGTT<br>CCGGTAACTGGGTTTGGAGACCTTTC | SEQ ID NO: 71 |
| g3473 xhoi | CTTTGGTCTCCTGCACAAGATTTACTGAGTTGTTCCCAACAAAGCAGTCGATGGCTGCCAACAAG<br>CTCGAGTTTAAGAATGATTGGTTTCAAACAATGGCTCTTGATTTTATCTGGGTTCCCACCTTTTG<br>AATCCTCTTCCGTTTGGAGACCTTTC | SEQ ID NO: 72 |
| g3068 | CTTTGGTCTCCTGCACCAGATTCACTGAGCTATTGCCAACAAAGCAACAGATGAAACAAAATAAA<br>CTCGAGCTTGAGAATGATGGGTCGTAGACAATGGCTGATGTTTCTGAGTGCCTTCTCATTTGTTG<br>AATCCATTGCCGTTTGGAGACCTTTC | SEQ ID NO: 73 |
| NDE | CTTTGGTCTCCTGCAGTAAATACCTTTGGCATTCCTGGTATTCCTGAATATGCTTCTTACCTTAA<br>CTCGAGTAAGACAAAAGTTATTCAACCAAATTGAAGCTTCTAGGTTGTTGCCAAAGAGAAGCAAA<br>TGATGCTACCGGTTTGGAGACCTTTC | SEQ ID NO: 74 |

TABLE 5

| Codon-optimized genes used in this study | | |
|---|---|---|
| Genes | Sequences (5' to 3') | Sequence ID Number |
| SpMAE1 | ATGGGCGAGTTGAAAGAGATTTTAAAGCAAAGATACCACGAATTATTAGATTGGAACGTTAAGG<br>CTCCACACGTTCCATTGTCCCAGAGATTGAAACACTTCACTTGGTCCTGGTTCGCTTGCACAAT<br>GGCGACCGGCGGAGTGGGACTTATCATCGGATCCTTTCCATTCAGATTCTACGGCTTGAACACG<br>ATCGGAAAGATCGTCTACATCTTACAGATTTTCTTATTCTCCCTTTTCGGTAGTTGTATGTTGT<br>TCAGATTCATCAAGTACCCATCGACAATTAAAGACTCTTGGAATCACCACCTCGAGAAATTATT<br>TATCGCAACCTGCTTATTGTCGATTTCAACCTTTATTGATATGCTCGCAATCTATGCTTACCCC<br>GACACTGGTGAATGGATGGTTTGGGTTATCCGTATTTTATACTATATCTATGTCGCTGTTTCCT<br>TCATCTACTGTGTCATGGCCTTCTTCACTATCTTTAACAATCACGTTTACACTATCGAGACAGC<br>CTCGCCAGCATGGATCTTACCCATCTTTCCACCAATGATCTGCGGAGTTATCGCCGGTGCTGTT<br>AACTCAACTCAGCCAGCGCACCAGCTTAAGAACATGGTGATTTTCGGAATTTTGTTCCAGGGTT<br>TGGGATTCTGGGTGTACCTCTTGTTGTTCGCAGTTAACGTTCTCAGATTCTTCACAGTCGGTTT<br>GGCTAAGCCACAGGACAGACCAGGAATGTTCATGTTCGTGGGACCCCCTGCCTTTAGTGGCTTA<br>GCTTTGATCAACATCGCAAGAGGCGCGATGGGTTCAAGACCCTACATCTTCGTCGGTGCAAATT<br>CTTCGGAATACTTAGGCTTCGTCTCCACTTTCATGGCAATCTTCATCTGGGGCTTGGCCGCATG<br>GTGCTATTGCTTAGCTATGGTCAGTTTCCTTGCTGGTTTCTTTACACGTGCGCCATTAAAATTC<br>GCATGCGGTTGGTTCGCCTTTATCTTTCCAAATGTTGGATTCGTGAACTGCACAATCGAAATTG<br>GCAAGATGATCGACTCAAAGGCATTTCAGATGTTCGGTCACATTATCGGTGTTATCTTGTGCAT<br>CCAATGGATTTTATTGATGTACTTGATGGTTAGAGCATTCCTTGTTAACGACTTGTGTTACCCA<br>GGTAAGGATGAGGACGCGCACCCACCACCTAAGCCTAACACTGGAGTTTTGAATCCCACTTTTC<br>CACCAGAGAAGGCGCCAGCTTCGTTAGAGAAGGTTGACACGCACGTTACTTCCACAGGTGGCGA<br>GTCCGACCCACCATCATCAGAGCACGAGTCCGTCTAG | SEQ ID NO: 56 |
| PaGDH | ATGAAAGGTTTACTTTACTATGGTACCAACGACATACGTTATAGTGAAACAGTACCTGAACCAG<br>AGATTAAAAACCCTAATGATGTTAAGATCAAAGTTTCTTATTGTGGGATATGTGGTACTGATTT<br>AAAAGAATTCACTTACTCAGGGGGACCCGTCTTTTTTCCTAAACAGGGAACAAAAGATAAGATT<br>TCCGGGTATGAATTACCATTATGTCCCGGACATGAGTTTTCAGGTACTGTCGTGGAAGTTGGTA<br>GTGGTGTCACGTCTGTTAAGCCTGGAGACAGAGTTGCTGTTGAAGCAACGTCACATTGCTCAGA<br>TCGTTCTAGATACAAGGACACTGTTGCTCAAGATTTGGGATTATGTATGGCATGTCAGTCAGGA<br>TCACCAAACTGTTGTGCCAGTTTGTCTTTTTGTGGTCTAGGAGGTGCCTCTGGTGGTTTCGCTG<br>AATATGTAGTCTACGGTGAAGATCACATGGTGAAGTTACCCGATTCAATCCCTGACGATATTGG | SEQ ID NO: 57 |

TABLE 5-continued

Codon-optimized genes used in this study

| Genes | Sequences (5' to 3') | Sequence ID Number |
|---|---|---|
| | TGCCTTGGTTGAACCGATCTCTGTTGCATGGCATGCAGTAGAAAGGGCTAGATTTCAGCCCGGT<br>CAAACAGCACTTGTGCTAGGCGGAGGTCCAATCGGTCTTGCAACCATACTTGCTCTACAAGGTC<br>ATCATGCAGGTAAGATTGTGTGTTCAGAACCAGCTCTAATCAGGAGACAATTTGCAAAAGAACT<br>TGGTGCTGAGGTCTTTGACCCTAGTACCTGTGATGACGCCAACGCTGTGTTGAAAGCAATGGTT<br>CCGGAAAATGAGGGTTTTCATGCAGCTTTCGATTGTTCTGGAGTACCACAGACCTTTACTACCT<br>CTATTGTGGCTACGGGTCCATCGGGAATTGCTGTCAATGTTGCAGTTTGGGGTGATCATCCAAT<br>CGGCTTTATGCCTATGAGTCTAACCTATCAAGAAAAATATGCAACTGGCTCAATGTGCTATACC<br>GTGAAAGATTTCCAGGAAGTTGTCAAAGCATTAGAAGATGGGTTGATTTCTCTTGACAAGGCAA<br>GGAAGATGATTACTGGCAAGGTTCATTTGAAGGATGGGGTCGAGAAGGGTTTTAAACAATTGAT<br>CGAACATAAAGAGAACAATGTTAAGATCCTAGTGACGCCCAATGAAGTAAGTTAG | |
| CjFPS1 | ATGACAGGAGAATTACTTGCTAGTGGTGAAGGCTGTAGTTCTGATATAGTATTAACTAACTCTA<br>CAGCAGCGCCTTCCTCTGGTCTTGAGAGAAGAGCAAACATTACTGACCACATCTCTTGTGAACA<br>TTTCACTGCTCTGCAAAGATTCAGATATGGATTCAGAGAGTACTTTGCTGAATTTATCGGTACC<br>ATGATCCTTGTGATGTTTGGTGACGGTGTTGTTGCCCAGTACACTCTGTCCAAGGGATCTGCTG<br>GTAACTATACAACCATTGCCTTTTCGTGGGCCACTGCCGTTTTCCTTGGTTACTGCTGTTCTGC<br>GGGTATCTCTGGTGCTCATTTGAACCCTGCTGTTACTCTTTCAGCTGCTACTTTCAGACAGTTC<br>CCATGGAGAAAGGTATTGGGTTACATGTTTGCCCAAGGTCTTGGTGGTTACATCGGCGCCCTTA<br>TCGTTTACGGTACCTATATCCAATCCATCAACAACTACTCTGGTGAAGGCCAGAGAATCGCCGT<br>CGGTGACAAATCCACAGGTGGAATCTTCTGTACTTTCCCACAACCTTACTTGAACACCAGGGTC<br>AGGTTACATCCGAGCTTGTCACCACTGCCCTTTTGCAGTTTGGTATTTTCTCCATGACTGATCC<br>TCACAATGCACCATTGGGTAACTTCTTCCCATTCGGATTATGGATCTTGATTTATGGATTGGGT<br>ACCTCTTTTGGTTACCAGACCGGTTATGCCATCAACTTTGCAAGAGATTTCACCCCAAGATTGG<br>CTGCTTTGACTGTCGGCTATGGTACCGAGATGTTCACCGCCTACTACCACTACTTCTGGGTGCC<br>AATGATCATCCCATTCATTGGTGCATTGCTCGGTGCTTTCATCTATGATTTCTTCATCTACCAA<br>GGCTTGGACTCGCCATTGAACCAGCCAAAGTTCGGCTACGACATCAGAAAGAAGAAGATCCAGG<br>AGTTTGAATTCAAATTGGAGAACTACAAGCTTGACTTCAACCCGGAGGCTAGCCACGGTCGTCT<br>TGACGCTTGA | SEQ ID NO: 58 |

TABLE 6

Hexokinase Proteins Identified

| Genes | Sequences (N to C) | Sequence ID Number |
|---|---|---|
| g3837 | MSQLDQKVKEIVESFEVEKELLQNLVTLFIRSAEYGLTHSSVGKAAMPMIPTYVTQIPTGKEKGVLLAAD<br>LGGTNFRVCSVKLNGDHTFELKQSKNPIPVDLMSSTTEELFSYLAGKIGQFVETHHNDIGDKMKLGFTFS<br>FPVEQTSLNSGTLIRWTKGFNIEDTVGKDIVAVLQDHLDRKNIPVHVAALANDTVGTLLARSYTGENKEG<br>LTSIGCIYGTGTNGAYNEKVENITKLPKEVVEELKSKGIDHMVINTEWGSFDNNLELLPTTKYDVEVDKI<br>SANPGYHLFEKRVSGMFLGEILRHILVDLYEQGLMFTQYPTINELPHRLKTPWLLHSEGLSIFEIDDSTN<br>LIATEIELKNMLRLPTTPEERKAIQKLTRAISKRAAHLAGVPIAALTMKIDAFKGHNVEVDVGVDGSVVE<br>FYPGFRTMMRDAIADTQIGAKGERRLHVNLSKDGSSVGAALCALSNNSL | SEQ ID NO: 67 |
| g1398 | MTQTLQAAFEKTKSELTVTTEKLEEITNHFVEELEKGISPAGGNIPMNPTWVMDYGSGSETGEYLAIDLG<br>GTNLRVIRVTLQGDSKFKSVNEKYPIPVPMRTGNKDDLFDFIAKSLDDFIKHQYGEDYKGEKLPLGFTFS<br>YPAHQNAINHGVLQTWTKGFDIPGVEGHDVVPMLQASLDKLNTPVEVVALINDTTGTLVASKYCDTETIM<br>GLIFGTGCNGAYYDFAKNIPKLEGKLASDINDETPMAINCEYGAFDNDWKVLPRTKYDIQIDQESPRPGQ<br>QFYEKMIAGYYLGEVLRLILLDYYSQGLVFINQDIKSLQVPFAMDTSFPSMIEEHGPEYAGKLFKDTFNI<br>TLTKEEEKVISDLCQIIGTRAARLSVCSIAGICRKMNYKSGHCAADGSVFNRYPYFKERAAAALNELFKW<br>NTDPKDYPIKLTHAEDGSGVGAAVIACLTEKRLLAGKSVGAKL | SEQ ID NO: 68 |
| g2945 | MTNSKLDLYTEKLHKDFHVSTVSLHKIIDYFIEELDRGLQDGTDPLGIPMNVAWWMEYPTGDETGDYLAL<br>DMGGTNLRVVIVHLKGKGQMETDQAFYKLPDGIRTVKDRNVLFDFMAEKLDQFLKDKHPEGIPENKVFPL<br>GFTFSYPATQSRINSGVLQRWTKGFDIPGVEGEDVVPLLTEKLKERNVPIKIVALINDTCGTLVASRYVD<br>PLTEMGCIFGTGVNGAYYEKVSNITKYKGRFPKDIPEDSPMLINCEYGSFDNAHKVIPRTRFDITIDETS<br>PRPGQQTFEKMTAGFYLGDLLRLTLLEAYTEGITFEDAPAEFVKCLNTPQCIDASFLSRIELDESDDLVT<br>AKKLFADEFKYPNATTDEVKFAKAAAQLISNRAARLSICGVAAVCKKRGYKKCHIAADGSVYLKYPNFAS<br>RAAEGLADVFGWGHEMPQSEHPIRIVTALDGSGVGAAIIAALAHKREVAGLSLGLED | SEQ ID NO: 69 |

Fermentation Experiments

For shake flask fermentations, single colonies of *I. orientalis* strains were inoculated into 2 mL of liquid YPAD medium with 20 g/L of glucose and cultured at 30° C. for 1 day. Then, the cells were subcultured in 2 mL of liquid SC-URA medium with 20 g/L of glucose and grown at 30° C. for 1 day to synchronize the cell growths. Cells were then transferred into 20 ml of SC-URA liquid medium with 50 g/L glucose, 50 g/L glucose and 20 g/L glycerol, or 70 g/L glucose in 125 mL Erlenmeyer flask. Cells were diluted to initial $OD_{600}$ of 0.2, and 10 g/L of calcium carbonate were supplemented in the fermentations. The cells were cultivated at 30° C. at 100 RPM (oxygen limited condition) or 250 RPM (aerobic condition). Samples were collected every 24 hours for HPLC analysis. Shake flask fermentations were conducted with three biological replicates.

For fed-batch fermentations in bench-top bioreactors (DASbox), single colonies of *I. orientalis* strains were inoculated into 2 mL liquid YPAD medium with 20 g/L of glucose and cultured for 1 day. Then, the cells were sub-cultured into 2 mL liquid SC-URA medium with 20 g/L of glucose and grown for 1 day. 1 mL of cells was then added into 100 ml of liquid SC-URA medium with 50 g/L glucose and 20 g/L glycerol or 100 ml of 2-fold diluted sugarcane juice in Eppendorf DASbox Mini Bioreactors (Eppendorf, Hamburg, Germany). The cells were cultivated at 30° C. with 800 RPM. pH was maintained at 3 using HCl and KOH. Industrial-grade $CO_2$ and $O_2$ gasses were continuously sparged into the bioreactors at flow rates of 0.33-0.67 vvm and 0.17 vvm (volume per working volume per min), respectively. One drop of Antifoam 204 was added to control foaming if necessary. For fermentations using pure glucose and glycerol, after the initial glucose and glycerol was depleted, additional glucose and glycerol were added to the bioreactors. For fermentation using sugarcane juice, after the initial sugars and glycerol were depleted, sugarcane juice, which was concentrated by boiling, was added to the bioreactors. Samples were collected every 24 hours for HPLC analysis. Fed-batch fermentations were conducted with two biological replicates.

Analytic Methods

Extracellular glucose, glycerol, pyruvate, succinate, and ethanol concentrations of fermentation broths were analyzed using the Agilent 1200 HPLC system equipped with a refractive index detector (Agilent Technologies, Wilmington, DE, USA) and Rezex ROA-Organic Acid H+ (8%) column (Phenomenex, Torrance, CA, USA). The column and detector were run at 50° C., and 0.005 N $H_2SO_4$ was used as the mobile phase at flow rate of 0.6 mL/min.

Metabolic Flux Analysis

To determine the fluxes of glucose consumption, pyruvate production, and succinate production, strain SA/MAE1/pdcΔ/gpdΔ was grown overnight in yeast nitrogen base (YNB) medium without amino acids consisting of 5% glucose and then inoculated in YNB medium at $OD_{600}$ of 0.1. At 0, 24, and 53 hours, $OD_{600}$ was measured, and the supernatant was collected. The supernatant was then diluted 50 fold in a solution of 40:40:20 methanol: acetonitrile: water. Glucose, pyruvate, and succinate were quantified with external calibration standard by LC-MS as described previously[59]. A conversion factor of 0.6 grams dry weight per $OD_{600}$ per liter was used to convert $OD_{600}$ to cell dry weight unit.

For $^{13}C$ isotope tracing analysis, yeast was cultured in media with [U-$^{13}C_6$] glucose or [1,2-$^{13}C_2$] glucose (Cambridge Isotope Laboratories, Tewksbury, MA, USA) at 50% enrichment. Strain SA/MAE1/pdcΔ/gpdΔ was first grown overnight and then inoculated into fresh media at $OD_{600}$ Of 1. The cultures were allowed to grow for about 36 hours to reach $OD_{600}$ of 6. For intracellular metabolite extraction, about 900 μL of cell culture was quickly vacuum filtered through a GVS Magna™ Nylon membrane filter with 0.5 μm pore size (Fisher Scientific, Pittsburgh, PA), quenched in 1 mL of ice-cold solution of 40:40:20 methanol: acetonitrile: water with 0.5% formic acid for about 2 minutes, and then neutralized with 88 μL of ammonium bicarbonate. The extracts were centrifuged at 20000 RPM, and the supernatants were analyzed by LC-MS. For amino acid analysis, the pellets from metabolite extractions were washed with water and hydrolyzed in 100 μL 2M HCl at 80° C. for 1 hour. Then, 10 μL of the hydrolysate supernatant was dried under pure nitrogen and redissolved in 100 μL of solution of 40:40:20 methanol: acetonitrile:water and analyzed by LC-MS. For LC-MS data analysis, the data was converted to mzXML by msconvert from ProteoWizard, and mass peaks were then picked by ElMaven software package (https://elucidatainc.github.io/ElMaven). $^{13}C$ natural isotope abundance was corrected using accucor R package (https://github.com/lparsons/accucor).

$^{13}C$ metabolic flux analysis was done with a customized core atom mapping model with redox balance in the INCA1.9 Suite[60]. Flux solution that best fits the mass isotope distribution of 26 metabolites was obtained under the constraint of glucose, pyruvate, and succinate fluxes and growth rate. Flux lower and upper bounds were obtained using parameter continuation.

REFERENCES

1. Lian, J., Mishra, S. & Zhao, H. Recent advances in metabolic engineering of *Saccharomyces cerevisiae*: new tools and their applications. *Metab. Eng.* 50, 85-108 (2018).
2. Du, J., Shao, Z. & Zhao, H. Engineering microbial factories for synthesis of value-added products. *J. Ind. Microbiol. Biotechnol.* 38 (8), 873-890 (2011).
3. Volk, M. J. et al. Metabolic Engineering: Methodologies and Applications. Chemical Reviews (2022). https://doi.org/10.1021/acs.chemrev.2c00403
4. Dai, Z. et al. Bio-based succinic acid: an overview of strain development, substrate utilization, and downstream purification. *Biofuels. Bioprod. Biorefin.* 14, 965-985 (2020).
5. Ahn, J. H., Jang, Y.-S. & Lee, S. Y. Production of succinic acid by metabolically engineered microorganisms. Curr. Opin. Biotechnol. 42, 54-66 (2016).
6. Ahn, J. H. et al. Enhanced succinic acid production by *Mannheimia* employing optimal malate dehydrogenase. *Nat. Commun.* 11 (1), 1970 (2020).
7. Wang, D. et al. High cell density fermentation via a metabolically engineered *Escherichia coli* for the enhanced production of succinic acid. *J. Chem. Technol. Biotechnol.* 86, 512-518 (2011).
8. Okino, S. et al. An efficient succinic acid production process in a metabolically engineered *Corynebacterium glutamicum* strain. *Appl. Microbiol. Biotechnol.* 81, 459-464 (2008).
9. Tran, V. G. & Zhao, H. Engineering robust microorganisms for organic acid production. *J. Ind. Microbiol. Biotechnol.* 0, kuab067 (2021).
10. Cui, Z. et al. Engineering of unconventional yeast *Yarrowia lipolytica* for efficient succinic acid production from glycerol at low pH. *Metab. Eng.* 42, 126-133 (2017).
11. Jiang, Z. et al. Engineering of *Yarrowia lipolytica* transporters for high-efficient production of biobased succinic acid from glucose. *Biotechnol. Biofuels* 14 (1), 145 (2021).
12. Yan, D. et al. Construction of reductive pathway in *Saccharomyces cerevisiae* for effective succinic acid fermentation at low pH value. *Bioresour. Technol.* 156, 232-239 (2014).
13. Xiao, H., Shao, Z., Jiang, Y., Dole, S. & Zhao, H. Exploiting Issatchenkia *orientalis* SD108 for succinic acid production. *Microb. cell factories* 13 (1), 1-11 (2014).
14. Isono, N., Hayakawa, H., Usami, A., Mishima, T. & Hisamatsu, M. A comparative study of ethanol production by *Issatchenkia orientalis* strains under stress conditions. *J. Biosci. Bioeng.* 113 (1), 76-78 (2012).

15. Park, H. J. et al. Low-pH production of d-lactic acid using newly isolated acid tolerant yeast *Pichia kudriavzevii* NG7. *Biotechnol. Bioeng.* 115, 2232-2242 (2018).
16. Cao, M. et al. A genetic toolbox for metabolic engineering of Issatchenkia *orientalis. Metab. Eng.* 59, 87-97 (2020).
17. Tran, V. G, Cao, M., Fatma, Z., Song, λ. & Zhao, H. Development of a CRISPR/Cas9-Based Tool for Gene Deletion in *Issatchenkia orientalis*. mSphere 4 (3), e00345-19 (2019).
18. Darbani, B., Stovicek, V., van der Hoek, S. A. & Borodina, I. Engineering Energetically Efficient Transport of Dicarboxylic Acids in Yeast *Saccharomyces cerevisiae. Proc. Natl. Acad. Sci. U.S.A.* 116, 19415-19420 (2019).
19. Suthers, P. F. et al. Genome-scale metabolic reconstruction of the non-model yeast *Issatchenkia orientalis* SD108 and its application to organic acids production. *Metab. Eng. Commun.* 11, e00148 (2020).
20. Chen, Z. & Liu, D. Toward glycerol biorefinery: metabolic engineering for the production of biofuels and chemicals from glycerol. *Biotechnol. Biofuels* 9, 205 (2016).
21. Liu, Y., Zhang, Y. G., Zhang, R. B., Zhang, F. & Zhu, J. Glycerol/glucose co-fermentation: one more proficient process to produce propionic acid by *Propionibacterium acidipropionici. Curr. Microbiol.* 62, 152-158 (2011).
22. Douglass, A. P. et al. Population genomics shows no distinction between pathogenic *Candida krusei* and environmental *Pichia* kudriavzevii: One species, four names. *PLoS Pathog.* 14 (7), e1007138 (2018).
23. Xi, Y. et al. Characterization of JEN family carboxylate transporters from the acid-tolerant yeast *Pichia kudriavzevii* and their applications in succinic acid production. *Microb. Biotechnol.* 14 (3), 1130-1147 (2021).
24. Klein, M. et al. Towards the exploitation of glycerol's high reducing power in *Saccharomyces cerevisiae*-based bioprocesses. *Metab. Eng.* 38, 464-472 (2016).
25. Lane, S. et al. Glucose repression can be alleviated by reducing phosphorylation rate in *Saccharomyces cerevisiae. Sci. Rep.* 8, 2613 (2018).
26. Jansen, M. L. & van Gulik, W. M. Towards large scale fermentative production of succinic acid. *Curr. Opin. Biotechnol.* 30, 190-197 (2014).
27. Li, Q. et al. One step recovery of succinic acid from fermentation broths by crystallization. *Sep. Purif. Technol.* 72 (3), 294-300 (2010).
28. Zale, J. et al. Metabolic engineering of sugarcane to accumulate energy-dense triacylglycerols in vegetative biomass. *Plant Biotechnol. J.* 14 (2), 661-9 (2016).
29. Zhang, J., Yu, L., Lin, M., Yan, Q. & Yang, S. T. n-Butanol production from sucrose and sugarcane juice by engineered *Clostridium tyrobutyricum* overexpressing sucrose catabolism genes and adhE2. *Bioresour. Technol.* 233, 51-57 (2017).
30. Taylor, R. et al. From the Sugar Platform to biofuels and biochemicals: Final report for the European Commission Directorate-General Energy (2015).
31. Li, Q.-Z. et al. Recovery processes of organic acids from fermentation broths in the biomass-based industry. *J. Microbiol. Biotechnol.* 26 (1), 1-8 (2016).
32. Cordova, L. T., Butler, J. & Alper, H. S. Direct production of fatty alcohols from glucose using engineered strains of *Yarrowia lipolytica. Metab. Eng. Commun.* 10, e00105 (2020).
32. Stylianou, E. et al. Bioprocess development using organic biowaste and sustainability assessment of succinic acid production with engineered *Yarrowia lipolytica* strain. *Biochem. Eng. J.* 174, 108099 (2021).
33. Li, C. et al. Efficient metabolic evolution of engineered *Yarrowia lipolytica* for succinic acid production using a glucose-based medium in an in situ fibrous bioreactor under low-pH condition. *Biotechnol. Biofuels* 11, 236 (2018).
34. Li, C., Gao, S., Yang, X. & Lin, C. S. K. Green and sustainable succinic acid production from crude glycerol by engineered *Yarrowia lipolytica* via agricultural residue-based in situ fibrous bed bioreactor. *Bioresour. Technol.* 249, 612-619 (2018).
35. Kumar, R., Basak, B. & Jeon, H.-B. Sustainable production and purification of succinic acid: A review of membrane-integrated green approach. *J. Clean. Prod.* 277, 123954 (2020).
36. Karp, M. et al. Post-Fermentation Recovery of Biobased Carboxylic Acids. *ACS Sustain. Chem. Eng.* 6 (11), 15273-15283 (2018).
37. Gupta, P., Kateja, N., Mishra, S., Kaur, H. & Rathore, S. A. Economic assessment of continuous processing for manufacturing of biotherapeutics. *Biotechnol. Prog.* 37 (2), e3108 (2021).
38. Alexandri, M. et al. Downstream separation and purification of succinic acid from fermentation broths using spent sulfite liquor as feedstock. *Sep. Purif. Technol.* 209, 666-675 (2019).
39. Lin, S. K. C. et al. Novel resin-based vacuum distillation-crystallization method for recovery of succinic acid crystals from fermentation broths. *Green Chem.* 12, 666-67 (2010).
40. Jokodola, O. E. et al. Process optimization for production and recovery of succinic acid using xylose-rich hydrolysates by *Actinobacillus succinogenes. Bioresour. Technol.* 344, Part B, 126224 (2022).
41. Luthfi, A. A. I. et al. Multiple crystallization as a potential strategy for efficient recovery of succinic acid following fermentation with immobilized cells. *Bioprocess Biosyst. Eng.* 43, 1153-1169 (2020).
42. Dickson, R. et al. Sustainable bio-succinic acid production: superstructure optimization, techno-economic, and lifecycle assessment. *Energy Environ. Sci.* 14, 3542-3558 (2021).
43. Dogbe, E. S., Mandegari, M. & Gorgens, J. F. Revitalizing the sugarcane industry by adding value to A-molasses in biorefineries. *Biofuels. Bioprod. Bioref.* 14, 1089-1104 (2020).
44. Efe, C., van der Wielen, L. A. M. & Straathof, A. J. J. Techno-economic analysis of succinic acid production using adsorption from fermentation medium. *Biomass Bioenerg.* 56, 479-492 (2013).
45. Ioannidou, S. M., Filippi, K., Kookos, I. K., Koutinas, A. & Ladakis, D. Techno-economic evaluation and life cycle assessment of a biorefinery using winery waste streams for the production of succinic acid and value-added co-products. *Bioresour. Technol.* 348, 126295 (2022).
46. Klein, B. C. et al. Process development and techno-economic analysis of bio-based succinic acid derived from pentoses integrated to a sugarcane biorefinery. *Biofuels. Bioprod. Bioref.* 11, 1051-1064 (2017).
47. Padi, R. K. & Chimphango, A. Feasibility of commercial waste biorefineries for cassava starch industries: Techno-economic assessment. *Bioresour. Technol.* 297, 122461 (2020).
48. Shaji, A., Shastri, Y., Kumar, V., Ranade, V. V. & Hindle, N. Economic and Environmental Assessment of Succinic Acid Production from Sugarcane Bagasse. *ACS Sustain. Chem. Eng.* 9, 12738-12746 (2021).

49. Claypool, J. T. & Raman, D. R. Development and validation of a technoeconomic analysis tool for early-stage evaluation of bio-based chemical production processes. *Bioresour. Technol.* 150, 486-495 (2013).

50. Ladakis, D., Stylianou, E., Ioannidou, S. M., Koutinas, A. & Pateraki, C. Biorefinery development, techno-economic evaluation and environmental impact analysis for the conversion of the organic fraction of municipal solid waste into succinic acid and value-added fractions. *Bioresour. Technol.* 354, 127172 (2022).

51. Cok, B., Tsiropoulos, I., Roes, A. L. & Patel, M. K. Succinic acid production derived from carbohydrates: An energy and greenhouse gas assessment of a platform chemical toward a bio-based economy. *Biofuels. Bioprod. Bioref.* 8, 16-29 (2014).

52. Dunn, J. B. et al. 2015. Life-cycle Analysis of Bioproducts and Their Conventional Counterparts in GREET (No. ANL/ESD-14/9 Rev.). Argonne National Lab. (ANL), Argonne, IL (United States). https://doi.org/10.2172/1250468.

53. Argonne National Laboratory, 2022. GREET 2022 Model. https://greet.es.anl.gov/54. Skorokhodova, A. Y., Morzhakova, A. A., Gulevich, A. Y. & Debabov, V. G. Manipulating pyruvate to acetyl-CoA conversion in *Escherichia coli* for anaerobic succinate biosynthesis from glucose with the yield close to the stoichiometric maximum. J. Biotechnol. 214, 33-42 (2015).

55. Shao, Z., Zhao, H. & Zhao, H. DNA assembler, an in vivo genetic method for rapid construction of biochemical pathways. *Nucleic Acids Res.* 37, e16 (2009).

56. Gibson, D. G. et al. Enzymatic assembly of DNA molecules up to several hundred kilobases. *Nat. Methods* 6, 343-345 (2009).

57. Engler, C., Kandzia, R. & Marillonnet, S. A one pot, one step, precision cloning method with high throughput capability. *PloS one* 3 (11), e3647 (2008).

58. Gietz, R. D., Schiestl, R. H., Willems, A. R. & Woods, R. A. Studies on the transformation of intact yeast cells by the LiAc/SS-DNA/PEG procedure. *Yeast* 11 (4), 355-360 (1995).

59. Wang, L. et al. Peak annotation and verification engine for untargeted LC-MS metabolomics. *Anal. Chem.* 91 (3), 1838-1846, (2019).

60. Young, J. D. INCA: a computational platform for isotopically non-stationary metabolic flux analysis. *Bioinformatics* 30 (9), 1333-1335 (2014).

61. Litsanov, B., Brocker, M. & Bott, M. (2012). Toward homosuccinate fermentation: metabolic engineering of *Corynebacterium glutamicum* for anaerobic production of succinate from glucose and formate. *Appl. Environ. Microbiol.* 78 (9), 3325-3337.

62. Wang, J. et al. A novel riboregulator switch system of gene expression for enhanced microbial production of succinic acid. *J. Ind. Microb. Biotechnol.* 45 (4), 253-269 (2018).

63. BioSTEAM Development Group. Bioindustrial-Park: BioSTEAM's Premier Repository for Biorefinery Models and Results [WWW Document]. URL: github.com/yoelcortes/Bioindustrial-Park (2023).

64. Cortes-Peña, Y., Kumar, D., Singh, V. & Guest, J. S. BioSTEAM: A Fast and Flexible Platform for the Design, Simulation, and Techno-Economic Analysis of Biorefineries under Uncertainty. *ACS Sustain. Chem. Eng.* 8, 3302-3310 (2020).

BioSTEAM Development Group, 2023. Bioindustrial-Park: BioSTEAM's Premier Repository for Biorefinery Models and Results [WWW Document]. URL github.com/yoelcortes/Bioindustrial-Park Argonne National Laboratory, 2022. GREET 2022 Model. https://greet.es.anl.gov/Bhagwat, S. S., Li, Y., Cortes-Pena, Y. R., Brace, E. C., Martin, T. A., Zhao, H., Guest, J. S., 2021. Sustainable Production of Acrylic Acid via 3-Hydroxypropionic Acid from Lignocellulosic Biomass. ACS Sustainable Chem. Eng. 9, 16659-16669. https://doi.org/10.1021/acssuschemeng. 1c05441 Cok, B., Tsiropoulos, I., Roes, A. L., Patel, M. K., 2014. Succinic acid production derived from carbohydrates: An energy and greenhouse gas assessment of a platform chemical toward a bio-based economy. Biofuels, Bioprod. Bioref. 8, 16-29. https://doi.org/10.1002/bbb. 1427

Cortes-Peña, Y., Kumar, D., Singh, V., Guest, J. S., 2020. BioSTEAM: A Fast and Flexible Platform for the Design, Simulation, and Techno-Economic Analysis of Biorefineries under 8 3302-3310. Uncertainty. ACS Sustainable Eng. Chem. https://doi.org/10.1021/acssuschemeng. 9b07040 Dickson, R., Mancini, E., Garg, N., Woodley, J. M., Gernaey, K. V., Pinelo, M., Liu, J., Mansouri, S. S., 2021. Sustainable bio-succinic acid production: superstructure optimization, techno-economic, and lifecycle assessment. Energy Environ. Sci. 14, 3542-3558. https://doi.org/10.1039/DOEE03545A Dunn, J. B., Adom, F., Sather, N., Han, J., Snyder, S., He, C., Gong, J., Yue, D., You, F., 2015. Life-cycle Analysis of Bioproducts and Their Conventional Counterparts in GREET (No. ANL/ESD-14/9 Rev.). Argonne National Lab. (ANL), Argonne, IL (United States). https://doi.org/10.2172/1250468

Taylor, R., Nattrass, L., Alberts, G., Robson, P., Chudziak, C., Bauen, A., Libelli, I. M., Lotti, G., Prussi, M., Nistri, R., Chiaramonti, D., lópez-Contreras, A. M., Bos, H. L., Eggink, G., Springer, J., Bakker, R., & van Ree, R., 2015. From the Sugar Platform to biofuels and biochemicals: Final report for the European Commission Directorate-General Energy.

We claim:

1. A recombinant *Issatchenkia* yeast comprising:
(a) heterologous polynucleotides encoding pyruvate carboxylase (PYC), malate dehydrogenase (MDH), fumarase (FUMR) and fumarate reductase (FDR);
(b) a heterologous polynucleotide encoding dicarboxylic acid transporter (MAE1);
(c) a deleted or non-functional pyruvate decarboxylase (PDC) gene;
(d) a deleted or non-functional glycerol 3-phosphate dehydrogenase (GPD) gene; and
(e) a heterologous polynucleotide encoding glycerol dehydrogenase (GDH).

2. The recombinant *Issatchenkia* yeast of claim 1, further comprising a deleted or non-functional JEN carboxylate transporter gene.

3. The recombinant *Issatchenkia* yeast of claim 1, further comprising a deleted or non-functional NADH dehydrogenase (NDE) gene.

4. The recombinant *Issatchenkia* yeast of claim 1, wherein the heterologous polynucleotide encoding glycerol dehydrogenase (GDH) is overexpressed.

5. The recombinant Issatchenkia yeast of claim 1, further comprising an over expressed dihydroxyacetone kinase gene (DAK).

6. The recombinant Issatchenkia yeast of claim 1, further comprising a deleted or non-functional g3837 hexokinase gene.

7. The recombinant Issatchenkia yeast of claim 1, further comprising a heterologous polynucleotide encoding invertase (SUC2).

8. The recombinant Issatchenkia yeast of claim 7, wherein the polynucleotide encoding invertase (SUC2) encodes a polypeptide having 85% or more sequence identity to SEQ ID NO:61.

9. The recombinant Issatchenkia yeast of claim 1, wherein the polynucleotide encoding pyruvate carboxylase (PYC), malate dehydrogenase (MDH), fumarase (FUMR) and fumarate reductase (FDR) encode polypeptides as shown in SEQ ID NO: 62, SEQ ID NO: 63, SEQ ID NO: 64, SEQ ID NO: 65, respectively, or polypeptides comprising 85% or more sequence identity to SEQ ID NO:62, SEQ ID NO:63, SEQ ID NO: 64, or SEQ ID NO:65.

10. The recombinant/ssatchenkia yeast of claim 1, wherein the polynucleotide encoding dicarboxylic acid transporter (MAE1) encodes a polypeptide having 85% or more sequence identity to SEQ ID NO: 59.

11. The recombinant Issatchenkia yeast of claim 1, wherein the polynucleotide encoding glycerol dehydrogenase (GDH) encodes a polypeptide having 85% or more sequence identity to SEQ ID NO:60.

12. A fermentation method for producing succinic acid comprising contacting a fermentation medium with the recombinant Issatchenkia yeast of claim 1; and
fermenting the fermentation medium and the recombinant Issatchenkia yeast wherein succinic acid is produced.

13. The method of claim 12, wherein the fermentation medium comprises glucose and glycerol.

14. The method of claim 12, wherein the fermentation medium comprises sugarcane juice, sugar beet feedstock, or sweet sorghum feedstock.

15. The method of claim 12, wherein the fermenting is a fed-batch process, a batch process, or a continuous process.

16. The method of claim 12, wherein a pH of the fermentation medium is about 2.0 to about 4.0.

17. The method of claim 12, wherein succinic acid is produced at more than 60 g/L.

18. The method of claim 12, wherein a yield of 0.40 g/g glucose equivalent or more is achieved.

19. The method of claim 12, wherein a productivity of 0.40 $g/L^{-1}/h^{-1}$ or more is achieved.

20. The method of claim 12, wherein no acid is added to the fermentation medium during the fermenting.

21. The method of claim 12, wherein no neutralization agents are added to the fermentation medium to control pH.

22. A recombinant Issatchenkia yeast comprising:
(a) heterologous polynucleotides encoding pyruvate carboxylase (PYC), malate dehydrogenase (MDH), fumarase (FUMR) and fumarate reductase (FDR);
(b) a heterologous polynucleotide encoding dicarboxylic acid transporter (MAE1);
(c) a deleted or non-functional pyruvate decarboxylase (PCD) gene;
(d) a deleted or non-functional glycerol 3-phosphate dehydrogenase (GPD) gene;
(e) a deleted or non-functional JEN carboxylate transporter gene;
(f) a heterologous polynucleotide encoding glycerol dehydrogenase (GDH);
(g) an overexpressed dihydroxyacetone kinase (DAK) gene; and
(h) a deleted or non-functional g3837 hexokinase or a heterologous polynucleotide encoding invertase (SUC2).

* * * * *

SEQUENCE LISTING

```
Sequence total quantity: 74
SEQ ID NO: 1            moltype = DNA  length = 39
FEATURE                 Location/Qualifiers
source                  1..39
                        mol_type = other DNA
                        organism = synthetic construct
SEQUENCE: 1
atcttaaaac acacacacaa aatgggcgag ttgaaagag                          39

SEQ ID NO: 2            moltype = DNA  length = 36
FEATURE                 Location/Qualifiers
```

```
source                  1..36
                        mol_type = other DNA
                        organism = synthetic construct
SEQUENCE: 2
tatagttcgc ctcagaatct agacggactc gtgctc                          36

SEQ ID NO: 3            moltype = DNA  length = 60
FEATURE                 Location/Qualifiers
source                  1..60
                        mol_type = other DNA
                        organism = synthetic construct
SEQUENCE: 3
tcttaaaaat attgaaccgt cgaaacgtcc caaacaagga aacgaaaaat gcaccacacc  60

SEQ ID NO: 4            moltype = DNA  length = 60
FEATURE                 Location/Qualifiers
source                  1..60
                        mol_type = other DNA
                        organism = synthetic construct
SEQUENCE: 4
aaaggtgaga attcaaaatg ttatttttga tcatgtaaag ggtagcacgt gatgaaaagg  60

SEQ ID NO: 5            moltype = DNA  length = 44
FEATURE                 Location/Qualifiers
source                  1..44
                        mol_type = other DNA
                        organism = synthetic construct
SEQUENCE: 5
acaaacaaac acaattacaa aaaatgtcac aagaaaaaca ttgg                 44

SEQ ID NO: 6            moltype = DNA  length = 39
FEATURE                 Location/Qualifiers
source                  1..39
                        mol_type = other DNA
                        organism = synthetic construct
SEQUENCE: 6
gaacaaacat cttgttgtag ttacgattgg tatgcactg                       39

SEQ ID NO: 7            moltype = DNA  length = 43
FEATURE                 Location/Qualifiers
source                  1..43
                        mol_type = other DNA
                        organism = synthetic construct
SEQUENCE: 7
tcttaaaaca cacacacaaa atgaaaggtt tactttacta tgg                  43

SEQ ID NO: 8            moltype = DNA  length = 37
FEATURE                 Location/Qualifiers
source                  1..37
                        mol_type = other DNA
                        organism = synthetic construct
SEQUENCE: 8
tatagttcgc ctcagaatct aacttacttc attgggc                         37

SEQ ID NO: 9            moltype = DNA  length = 51
FEATURE                 Location/Qualifiers
source                  1..51
                        mol_type = other DNA
                        organism = synthetic construct
SEQUENCE: 9
ctgtgtagtt aattgaattc ttaagtttct tgatttaacc tgatccaaaa g         51

SEQ ID NO: 10           moltype = DNA  length = 60
FEATURE                 Location/Qualifiers
source                  1..60
                        mol_type = other DNA
                        organism = synthetic construct
SEQUENCE: 10
ccaagcgcgc aattaaccct cactaaaggg aacaaaagct ggtatctgtc aacaacgtac  60

SEQ ID NO: 11           moltype = DNA  length = 60
FEATURE                 Location/Qualifiers
source                  1..60
                        mol_type = other DNA
                        organism = synthetic construct
SEQUENCE: 11
aatacgactc actatagggc gaattgggta ccgggccccc cccgaaaaat gcaccacacc  60

SEQ ID NO: 12           moltype = DNA  length = 60
```

```
FEATURE                 Location/Qualifiers
source                  1..60
                        mol_type = other DNA
                        organism = synthetic construct
SEQUENCE: 12
gacataccccc ttttggatca ggttaaatca agaaacttaa gaattcaatt aactacacag  60

SEQ ID NO: 13           moltype = DNA  length = 60
FEATURE                 Location/Qualifiers
source                  1..60
                        mol_type = other DNA
                        organism = synthetic construct
SEQUENCE: 13
attcttgtac agctttgatg cgagcattaa taagaaagaa actagggcga attgggtacc  60

SEQ ID NO: 14           moltype = DNA  length = 60
FEATURE                 Location/Qualifiers
source                  1..60
                        mol_type = other DNA
                        organism = synthetic construct
SEQUENCE: 14
gaggatatta atggtactta agaatagttg aatagatata tgcatgatta cgccaagcgc  60

SEQ ID NO: 15           moltype = DNA  length = 41
FEATURE                 Location/Qualifiers
source                  1..41
                        mol_type = other DNA
                        organism = synthetic construct
SEQUENCE: 15
acaaacaaac acaattacaa aaaatgcttt tgcaagcttt c                        41

SEQ ID NO: 16           moltype = DNA  length = 42
FEATURE                 Location/Qualifiers
source                  1..42
                        mol_type = other DNA
                        organism = synthetic construct
SEQUENCE: 16
gaacaaacat cttgttgtag ctattttact tcccttactt gg                       42

SEQ ID NO: 17           moltype = DNA  length = 60
FEATURE                 Location/Qualifiers
source                  1..60
                        mol_type = other DNA
                        organism = synthetic construct
SEQUENCE: 17
ttataaaaac tgataaacca tgagagtgta ccgataagta aacggatcct tgatttaacc  60

SEQ ID NO: 18           moltype = DNA  length = 60
FEATURE                 Location/Qualifiers
source                  1..60
                        mol_type = other DNA
                        organism = synthetic construct
SEQUENCE: 18
attttacctt ttacaaatta catcaaaagg ttaatttctc tctatctgtc aacaacgtac  60

SEQ ID NO: 19           moltype = DNA  length = 48
FEATURE                 Location/Qualifiers
source                  1..48
                        mol_type = other DNA
                        organism = synthetic construct
SEQUENCE: 19
acaaacaaac acaattacaa aaaatgacag gagaattact tgctagtg                 48

SEQ ID NO: 20           moltype = DNA  length = 38
FEATURE                 Location/Qualifiers
source                  1..38
                        mol_type = other DNA
                        organism = synthetic construct
SEQUENCE: 20
gaacaaacat cttgttgtag tcaagcgtca agacgacc                            38

SEQ ID NO: 21           moltype = DNA  length = 46
FEATURE                 Location/Qualifiers
source                  1..46
                        mol_type = other DNA
                        organism = synthetic construct
SEQUENCE: 21
acaaacaaac acaattacaa aaaatgctca accagccgaa aaaacc                   46
```

```
SEQ ID NO: 22          moltype = DNA  length = 42
FEATURE                Location/Qualifiers
source                 1..42
                       mol_type = other DNA
                       organism = synthetic construct
SEQUENCE: 22
gaacaaacat cttgttgtag ctaactactg tccgagtcgt cg                    42

SEQ ID NO: 23          moltype = DNA  length = 18
FEATURE                Location/Qualifiers
source                 1..18
                       mol_type = other DNA
                       organism = synthetic construct
SEQUENCE: 23
acgcgtaaac agggaagg                                               18

SEQ ID NO: 24          moltype = DNA  length = 21
FEATURE                Location/Qualifiers
source                 1..21
                       mol_type = other DNA
                       organism = synthetic construct
SEQUENCE: 24
acgcgtaaca cttagaatac g                                           21

SEQ ID NO: 25          moltype = DNA  length = 21
FEATURE                Location/Qualifiers
source                 1..21
                       mol_type = other DNA
                       organism = synthetic construct
SEQUENCE: 25
cattgttgga ccacgtcaag g                                           21

SEQ ID NO: 26          moltype = DNA  length = 23
FEATURE                Location/Qualifiers
source                 1..23
                       mol_type = other DNA
                       organism = synthetic construct
SEQUENCE: 26
aacgagaatg attggttttt ctg                                         23

SEQ ID NO: 27          moltype = DNA  length = 22
FEATURE                Location/Qualifiers
source                 1..22
                       mol_type = other DNA
                       organism = synthetic construct
SEQUENCE: 27
cccctgctga aagattatct ac                                          22

SEQ ID NO: 28          moltype = DNA  length = 21
FEATURE                Location/Qualifiers
source                 1..21
                       mol_type = other DNA
                       organism = synthetic construct
SEQUENCE: 28
aattagcacc tgataaggca c                                           21

SEQ ID NO: 29          moltype = DNA  length = 25
FEATURE                Location/Qualifiers
source                 1..25
                       mol_type = other DNA
                       organism = synthetic construct
SEQUENCE: 29
atgactttac acaaaaattc caacg                                       25

SEQ ID NO: 30          moltype = DNA  length = 21
FEATURE                Location/Qualifiers
source                 1..21
                       mol_type = other DNA
                       organism = synthetic construct
SEQUENCE: 30
gggaattatc agcaattgct c                                           21

SEQ ID NO: 31          moltype = DNA  length = 22
FEATURE                Location/Qualifiers
source                 1..22
                       mol_type = other DNA
                       organism = synthetic construct
SEQUENCE: 31
atgtctgatt tagagtcaca ac                                          22
```

```
SEQ ID NO: 32          moltype = DNA  length = 18
FEATURE                Location/Qualifiers
source                 1..18
                       mol_type = other DNA
                       organism = synthetic construct
SEQUENCE: 32
ctctccactt atgtgacg                                                     18

SEQ ID NO: 33          moltype = DNA  length = 20
FEATURE                Location/Qualifiers
source                 1..20
                       mol_type = other DNA
                       organism = synthetic construct
SEQUENCE: 33
gaggtgactt atttagaagc                                                   20

SEQ ID NO: 34          moltype = DNA  length = 19
FEATURE                Location/Qualifiers
source                 1..19
                       mol_type = other DNA
                       organism = synthetic construct
SEQUENCE: 34
atttcctttg agcgttacc                                                    19

SEQ ID NO: 35          moltype = DNA  length = 20
FEATURE                Location/Qualifiers
source                 1..20
                       mol_type = other DNA
                       organism = synthetic construct
SEQUENCE: 35
gaaatgccaa gtgtttgagc                                                   20

SEQ ID NO: 36          moltype = DNA  length = 21
FEATURE                Location/Qualifiers
source                 1..21
                       mol_type = other DNA
                       organism = synthetic construct
SEQUENCE: 36
gctggtctat aataaatagg g                                                 21

SEQ ID NO: 37          moltype = DNA  length = 20
FEATURE                Location/Qualifiers
source                 1..20
                       mol_type = other DNA
                       organism = synthetic construct
SEQUENCE: 37
actttctgta acaccgtttc                                                   20

SEQ ID NO: 38          moltype = DNA  length = 22
FEATURE                Location/Qualifiers
source                 1..22
                       mol_type = other DNA
                       organism = synthetic construct
SEQUENCE: 38
taatcaagaa aagacaatga cc                                                22

SEQ ID NO: 39          moltype = DNA  length = 19
FEATURE                Location/Qualifiers
source                 1..19
                       mol_type = other DNA
                       organism = synthetic construct
SEQUENCE: 39
ccagcttcgt tagagaagg                                                    19

SEQ ID NO: 40          moltype = DNA  length = 21
FEATURE                Location/Qualifiers
source                 1..21
                       mol_type = other DNA
                       organism = synthetic construct
SEQUENCE: 40
tagggtataa catgaacttg g                                                 21

SEQ ID NO: 41          moltype = DNA  length = 23
FEATURE                Location/Qualifiers
source                 1..23
                       mol_type = other DNA
                       organism = synthetic construct
SEQUENCE: 41
```

```
gaggaatta gaagatttga cag                                            23

SEQ ID NO: 42          moltype = DNA  length = 20
FEATURE                Location/Qualifiers
source                 1..20
                       mol_type = other DNA
                       organism = synthetic construct
SEQUENCE: 42
gttctacatt gacaagttcc                                               20

SEQ ID NO: 43          moltype = DNA  length = 24
FEATURE                Location/Qualifiers
source                 1..24
                       mol_type = other DNA
                       organism = synthetic construct
SEQUENCE: 43
tgcaaagcga tagtctgttt tgtc                                          24

SEQ ID NO: 44          moltype = DNA  length = 24
FEATURE                Location/Qualifiers
source                 1..24
                       mol_type = other DNA
                       organism = synthetic construct
SEQUENCE: 44
aaacgacaaa acagactatc gctt                                          24

SEQ ID NO: 45          moltype = DNA  length = 24
FEATURE                Location/Qualifiers
source                 1..24
                       mol_type = other DNA
                       organism = synthetic construct
SEQUENCE: 45
tgcataattt caacacctta ctcc                                          24

SEQ ID NO: 46          moltype = DNA  length = 24
FEATURE                Location/Qualifiers
source                 1..24
                       mol_type = other DNA
                       organism = synthetic construct
SEQUENCE: 46
aaacggagta aggtgttgaa atta                                          24

SEQ ID NO: 47          moltype = DNA  length = 24
FEATURE                Location/Qualifiers
source                 1..24
                       mol_type = other DNA
                       organism = synthetic construct
SEQUENCE: 47
tgcataaaca ctaagtttca agcc                                          24

SEQ ID NO: 48          moltype = DNA  length = 24
FEATURE                Location/Qualifiers
source                 1..24
                       mol_type = other DNA
                       organism = synthetic construct
SEQUENCE: 48
aaacggcttg aaacttagtg ttta                                          24

SEQ ID NO: 49          moltype = DNA  length = 24
FEATURE                Location/Qualifiers
source                 1..24
                       mol_type = other DNA
                       organism = synthetic construct
SEQUENCE: 49
tgcattagac agaatgaagg cacc                                          24

SEQ ID NO: 50          moltype = DNA  length = 24
FEATURE                Location/Qualifiers
source                 1..24
                       mol_type = other DNA
                       organism = synthetic construct
SEQUENCE: 50
aaacggtgcc ttcattctgt ctaa                                          24

SEQ ID NO: 51          moltype =   length =
SEQUENCE: 51
000

SEQ ID NO: 52          moltype =   length =
```

```
SEQUENCE: 52
000

SEQ ID NO: 53          moltype =   length =
SEQUENCE: 53
000

SEQ ID NO: 54          moltype =   length =
SEQUENCE: 54
000

SEQ ID NO: 55          moltype =   length =
SEQUENCE: 55
000

SEQ ID NO: 56          moltype = DNA  length = 1317
FEATURE                Location/Qualifiers
source                 1..1317
                       mol_type = unassigned DNA
                       organism = unidentified
SEQUENCE: 56
atgggcgagt tgaaagagat tttaaagcaa agataccacg aattattaga ttggaacgtt  60
aaggctccac acgttccatt gtcccagaga ttgaaacact tcacttggtc ctggttcgct  120
tgcacaatgg cgaccggcgg agtgggactt atcatcggat cctttccatt cagattctac  180
ggcttgaaca cgatcggaaa gatcgtctac atcttacaga ttttcttatt ctcccttttc  240
ggtagttgta tgttgttcag attcatcaag tacccatcga caattaaaga ctcttggaat  300
caccacctcg agaaattatt tatcgcaacc tgcttattgt cgatttcaac ctttattgat  360
atgctcgcaa tctatgctta ccccgacact ggtgaatgga tggtttgggt tatccgtatt  420
ttatactata tctatgtcgc tgtttccttc atctactgtg tcatggcctt cttcactatc  480
tttaacaatc acgtttacac tatcgagaca gcctcgccag catggatctt acccatcttt  540
ccaccaatga tctgcggagt tatcgccggt gctgttaact caactcagcc agcgcaccag  600
cttaagaaca tggtgatttt cggaattttg ttccagggtt tgggattctg ggtgtacctc  660
ttgttgttcg cagttaacgt tctcagattc ttcacagtcg gtttggctaa gccacaggac  720
agaccaggaa tgttcatgtt cgtgggaccc cctgccttta gtggcttagc tttgatcaac  780
atcgcaagag gcgcgatggg ttcaagaccc tacatcttcg tcggtgcaaa ttcttcggaa  840
tacttaggct tcgtctccac tttcatggca atcttcatct ggggcttggc cgcatggtgc  900
tattgcttag ctatggtcag tttccttgct ggtttcttta cacgtgcgcc attaaaattc  960
gcatgcggtt ggttcgcctt tatctttcca aatgttggat tcgtgaactg cacaatcgaa  1020
attggcaaga tgatcgactc aaaggcattt cagatgttcg gtcacattat cggtgttatc  1080
ttgtgcatcc aatggatttt attgatgtac ttgatggtta gagcattcct tgttaacgac  1140
ttgtgttacc caggtaagga tgaggacgcg cacccaccac ctaagcctaa cactggagtt  1200
ttgaatccca cttttccacc agagaaggcg ccagcttcgt tagagaaggt tgacacgcac  1260
gttacttcca caggtggcga gtccgaccca ccatcatcag agcacgagtc cgtctag     1317

SEQ ID NO: 57          moltype = DNA  length = 1143
FEATURE                Location/Qualifiers
source                 1..1143
                       mol_type = unassigned DNA
                       organism = unidentified
SEQUENCE: 57
atgaaaggtt tactttacta tggtaccaac gacatacgtt atagtgaaac agtacctgaa  60
ccagagatta aaaaccctaa tgatgttaag atcaaagttt cttattgtgg gatatgtggt  120
actgatttaa aagaattcac ttactcaggg ggacccgtct tttttcctaa acagggaaca  180
aaagataaga tttccgggta tgaattacca ttatgtcccg gacatgagtt ttcaggtact  240
gtcgtggaag ttggtagtgg tgtcacgtct gttaagcctg gagacagagt tgctgttgaa  300
gcaacgtcac attgctcaga tcgttctaga tacaaggaca ctgttgctca agatttggga  360
ttatgtatgg catgtcagtc aggatcacca aactgttgtg ccagtttgtc tttttgtggt  420
ctaggaggtg cctctggtgg tttcgctgaa tatgtagtct acggtgaaga tcacatggtg  480
aagttacccg attcaatccc tgacgatatt ggtgccttgg ttgaaccgat ctctgttgca  540
tggcatgcag tagaaagggc tagatttcag cccggtcaaa cagcacttgt gctaggcgga  600
ggtccaatcg gtcttgcaac catacttgct ctacaaggtc atcatgcagg taagattgtg  660
tgttcagaac cagctctaat caggagacaa tttgcaaaag aacttggtgc tgaggtcttt  720
gaccctagta cctgtgatga cgccaacgct gtgttgaaag caatggttcc ggaaaatgag  780
ggttttcatg cagctttcga ttgttctgga gtaccacaga cctttactac ctctattgtg  840
gctacgggtc catcgggaat tgctgtcaat gttgcagttt ggggtgatca tccaatcggc  900
tttatgccta tgagtctaac ctatcaagaa aaatatgcaa ctggctcaat gtgctatacc  960
gtgaaagatt tccaggaagt tgtcaaagca ttagaagatg ggttgatttc tcttgacaag  1020
gcaaggaaga tgattactgg caaggttcat ttgaaggatg ggtcgagaa gggttttaaa  1080
caattgatcg aacataaaga gaacaatgtt aagatcctag tgacgcccaa tgaagtaagt  1140
tag                                                                1143

SEQ ID NO: 58          moltype = DNA  length = 1035
FEATURE                Location/Qualifiers
source                 1..1035
                       mol_type = genomic DNA
                       organism = Cyberlindnera jadinii
SEQUENCE: 58
atgacaggag aattacttgc tagtggtgaa ggctgtagtt ctgatatagt attaactaac  60
tctacagcag cgccttcctc tggtcttgag agaagagcaa acattactga ccacatctct  120
```

```
tgtgaacatt tcactgctct gcaaagattc agatatggat tcagagagta ctttgctgaa  180
tttatcggta ccatgatcct tgtgatgttt ggtgacggtg ttgttgccca gtacactctg  240
tccaagggat ctgctggtaa ctatacaacc attgcctttt cgtgggccac tgccgttttc  300
cttggttact gctgttctgc gggtatctct ggtgctcatt tgaaccctgc tgttactctt  360
tcagctgcta ctttcagaca gttcccatgg agaaaggtat tgggttacat gtttgcccaa  420
ggtcttggtg gttacatcgg cgccccttatc gtttacggta cctatatcca atccatcaac  480
aactactctg gtgaaggcca gagaatcgcc gtcggtgaca aatccacagg tggaatcttc  540
tgtactttcc cacaacctta cttgaacacc aagggtcagg ttacatccga gcttgtcacc  600
actgcccttt tgcagtttgg tattttctcc atgactgatc ctcacaatgc accattgggt  660
aacttcttcc cattcggatt atggatcttg atttatggat tgggtacctc ttttggttac  720
cagaccggtt atgccatcaa ctttgcaaga gatttcaccc caagattggc tgctttgact  780
gtcggctatg gtaccgagat gttcaccgcc tactaccact acttctgggt gccaatgatc  840
atcccattca ttggtgcatt gctcggtgct ttcatctatg atttcttcat ctaccaaggc  900
ttggactcgc cattgaacca gccaaagttc ggctacgaca tcagaaagaa gaagatccag  960
gagtttgaat tcaaattgga gaactacaag cttgacttca acccggaggc tagccacggt  1020
cgtcttgacg cttga                                                  1035
```

```
SEQ ID NO: 59          moltype = AA  length = 438
FEATURE                Location/Qualifiers
source                 1..438
                       mol_type = protein
                       organism = Schizosaccharomyces pombe
SEQUENCE: 59
MGELKEILKQ RYHELLDWNV KAPHVPLSQR LKHFTWSWFA CTMATGGVGL IIGSFPFRFY  60
GLNTIGKIVY ILQIFLFSLF GSCMLFRFIK YPSTIKDSWN HHLEKLFIAT CLLSISTFID  120
MLAIYAYPDT GEWMVWVIRI LYYIYVAVSF IYCVMAFFTI FNNHVYTIET ASPAWILPIF  180
PPMICGVIAG AVNSTQPAHQ LKNMVIFGIL FQGLGFWVYL LLFAVNVLRF FTVGLAKPQD  240
RPGMFMFVGP PAFSGLALIN IARGAMGSRP YIFVGANSSE YLGFVSTFMA IFIWGLAAWC  300
YCLAMVSFLA GFFTRAPLKF ACGWFAFIFP NVGFVNCTIE IGKMIDSKAF QMFGHIIGVI  360
LCIQWILLMY LMVRAFLVND LCYPGKDEDA HPPPKPNTGV LNPTFPPEKA PASLEKVDTH  420
VTSTGGESDP PSSEHESV                                                438
```

```
SEQ ID NO: 60          moltype = AA  length = 380
FEATURE                Location/Qualifiers
source                 1..380
                       mol_type = protein
                       organism = Ogataea parapolymorpha
SEQUENCE: 60
MKGLLYYGTN DIRYSETVPE PEIKNPNDVK IKVSYCGICG TDLKEFTYSG GPVFFPKQGT  60
KDKISGYELP LCPGHEFSGT VVEVGSGVTS VKPGDRVAVE ATSHCSDRSR YKDTVAQDLG  120
LCMACQSGSP NCCASLSFCG LGGASGGFAE YVVYGEDHMV KLPDSIPDDI GALVEPISVA  180
WHAVERARFQ PGQTALVLGG GPIGLATILA LQGHHAGKIV CSEPALIRRQ FAKELGAEVF  240
DPSTCDDANA VLKAMVPENE GFHAAFDCSG VPQTFTTSIV ATGPSGIAVN VAVWGDHPIG  300
FMPMSLTYQE KYATGSMCYT VKDFQEVVKA LEDGLISLDK ARKMITGKVH LKDGVEKGFK  360
QLIEHKENNV KILVTPNEVS                                              380
```

```
SEQ ID NO: 61          moltype = AA  length = 532
FEATURE                Location/Qualifiers
source                 1..532
                       mol_type = protein
                       organism = Saccharomyces cerevisiae
SEQUENCE: 61
MLLQAFLFLL AGFAAKISAS MTNETSDRPL VHFTPNKGWM NDPNGLWYDE KDAKWHLYFQ  60
YNPNDTVWGT PLFWGHATSD DLTNWEDQPI AIAPKRNDSG AFSGSMVVDY NNTSGFFNDT  120
IDPRQRCVAI WTYNTPESEE QYISYSLDGG YTFTEYQKNP VLAANSTQFR DPKVFWYEPS  180
QKWIMTAAKS QDYKIEIYSS DDLKSWKLES AFANEGFLGY QYECPGLIEV PTEQDPSKSY  240
WVMFISINPG APAGGSFNQY FVGSFNGTHF EAFDNQSRVV DFGKDYYALQ TFFNTDPTYG  300
SALGIAWASN WEYSAFVPTN PWRSSMSLVR KFSLNTEYQA NPETELINLK AEPILNISNA  360
GPWSRFATNT TLTKANSYNV DLSNSTGTLE FELVYAVNTT QTISKSVFAD LSLWFKGLED  420
PEEYLRMGFE VSASSFFLDR GNSKVKFVKE NPYFTNRMSV NNQPFKSEND LSYYKVYGLL  480
DQNILELYFN DGDVVSTNTY FMTTGNALGS VNMTTGVDNL FYIDKFQVRE VK          532
```

```
SEQ ID NO: 62          moltype = AA  length = 1179
FEATURE                Location/Qualifiers
source                 1..1179
                       mol_type = protein
                       organism = Pichia kudriavzevii
SEQUENCE: 62
MSTVEDHSSL HKLRKESEIL SNANKILVAN RGEIPIRIFR SAHELSMHTV AIYSHEDRLS  60
MHRLKADEAY AIGKTGQYSP VQAYLQIDEI IKIAKEHDVS MIHPGYGFLS ENSEFAKKVE  120
ESGMIWVGPP AEVIDSVGDK VSARNLAIKC DVPVVPGTDG PIEDIEQAKQ FVEQYGYPVI  180
IKAAFGGGGR GMRVVREGDD IVDAFQRASS EAKSAFGNGT CFIERFLDKP KHIEVQLLAD  240
NYGNTIHLFE RDCSVQRRHQ KVVEIAPAKT LPVEVRNAIL KDAVTLAKTA NYRNAGTAEF  300
LVDSQNRHYF IEINPRIQVE HTITEEITGV DIVAAQIQIA AGASLEQLGL LQNKITTRGF  360
AIQCRITTED PAKNFAPDTG KIEVYRSAGG NGVRLDGGNG FAGAVISPHY DSMLVKCSTS  420
GSNYEIARRK MIRALVEFRI RGVKTNIPFL LALLTHPVFI SGDCWTTFID DTPSLFEMVS  480
SKNRAQKLLA YIGDLCVNGS SIKGQIGFPK LNKEAEIPDL LDPNDEVIDV SKPSTNGLRP  540
YLLKYGPDAF SKKVRGFDGC MIMDTTWRDA HQSLLATRVR TIDLLRIAPT TSHALQNAFA  600
LECWGGATFD VAMRFLYEDP WERLRQLRKA VPNIPFQMLL RGANGVAYSS LPDNAIDHFV  660
```

-continued

```
KQAKDNGVDI FRVFDALNDL EQLKVGVDAV KKAGGVVEAT VCYSGDMLIP GKKYNLDYYL  720
ETVGKIVEMG THILGIKDMA GTLKPKAAKL LIGSIRSKYP DLVIHVHTHD SAGTGISTYV  780
ACALAGADIV DCAINSMSGL TSQPSMSAFI AALDGDIETG VPEHFARQLD AYWAEMRLLY  840
SCFEADLKGP DPEVYKHEIP GGQLTNLIFQ AQQVGLGEQW EETKKKYEDA NMLLGDIVKV  900
TPTSKVVGDL AQFMVSNKLE KEDVEKLANE LDFPDSVLDF FEGLMGTPYG GFPEPLRTNV  960
ISGKRRKLKG RPGLELEPFN LEEIRENLVS RFGPGITECD VASYNMYPKV YEQYRKVVEK  1020
YGDLSVLPTK AFLAPPTIGE EVHVEIEQGK TLIIKLLAIS DLSKSHGTRE VYFELNGEMR  1080
KVTIEDKTAA IETVTRAKAD GHNPNEVGAP MAGVVVEVRV KHGTEVKKGD PLAVLSAMKM  1140
EMVISAPVSG RVGEVFVNEG DSVDMGDLLV KIAKDEAPA                        1179

SEQ ID NO: 63          moltype = AA  length = 333
FEATURE                Location/Qualifiers
source                 1..333
                       mol_type = protein
                       organism = Pichia kudriavzevii
SEQUENCE: 63
MVKVTILGAA GGIGQPLSLL LRLNPWIDEL ALFDIVNTPG VSCDLSHIPA SQVVNGYAPK  60
SKSDTETIKT ALKGADIVVI PAGIPRKPGM TRNDLFKINA GIVKSLIHSA GTTCPDAFIC  120
VISNPVNSTV PIAVEELKRL NVFNPHKVFG ITTLDNFRLE EFLSGELGGI VKPNDLYGDV  180
VAIGGHSGDS IVPILNSWNL NFINDGDSYN KLVKRVQFGG DEVVKAKDGK GSATLSMATA  240
AYRFVNNLLD AIVNNKKVKE VAFVKIDQLP TTRVPYFVVD ETQYFSLPII LGRQGIERVT  300
FPESLTEQEV RMTKHAVAKV KVDVNKGFNF VHG                              333

SEQ ID NO: 64          moltype = AA  length = 471
FEATURE                Location/Qualifiers
source                 1..471
                       mol_type = protein
                       organism = Pichia kudriavzevii
SEQUENCE: 64
MFSTTSIAKR IEKDAFGDIE VPNEKYWGAQ TQRSLQNFKI GGKREVMPEP IIKSFGILKK  60
ATAKINAESG ALDPKLSEAI QQAATEVYEG KLMDHFPLVV FQTGSGTQSN MNANEVISNR  120
AIEILGGELG SKTPVHPNDH VNMSQSSNDT FPTVMHIAAV TEVSSHLLPE LTALRDALQK  180
KSDEFKNIIK IGRTHLQDAT PLTLGQEFSG YVQQCTNGIK RIEIALEHLR YLAQGGTAVG  240
TGLNTKKGFA EKVANEVTKL TGLQFYTAPN KFEALAAHDA VVEMSGALNT VAVSLFKIAQ  300
DIRYLGSGPR CGYGELALPE NEPGSSIMPG KVNPTQNEAL TMLCTQVFGN HSCITFAGAS  360
GQFELNVFKP VMISNLLSSI RLLGDGCNSF RIHCVEGIIA NTDKIDKLLH ESLMLVTALN  420
PHIGYDKASK IAKNAHKKGL TLKQSALELG YLTEEQFNEW VRPENMIGPK D           471

SEQ ID NO: 65          moltype = AA  length = 1139
FEATURE                Location/Qualifiers
source                 1..1139
                       mol_type = protein
                       organism = Trypanosoma brucei
SEQUENCE: 65
MVDGRSSASI VAVDPERAAR ERDAAARALL QDSPLHTTMQ YATSGLELTV PYALKVVASA  60
DTFDRAKEVA DEVLRCAWQL ADTVLNSFNP NSEVSLVGRL PVGQKHQMSA PLKRVMACCQ  120
RVYNSSAGCF DPSTAPVAKA LREIALGKER NNACLEALTQ ACTLPNSFVI DFEAGTISRK  180
HEHASLDLGG VSKGYIVDYV IDNINAAGFQ NVFFDWGGDC RASGMNARNT PWVVGITRPP  240
SLDMLPNPPK EASYISVISL DNEALATSGD YENLIYTADD KPLTCTYDWK GKELMKPSQS  300
NIAQVSVKCY SAMYADALAT ACFIKRDPAK VRQLLDGWRY VRDTVRDYRV YVRENERVAK  360
MFEIATEDAE MRKRRISNTL PARVIVVGGG LAGLSAAIEA AGCGAQVVLM EKEAKLGGNS  420
AKATSGINGW GTRAQAKASI VDGGKYFERD TYKSGIGGNT DPALVKTLSM KSADAIGWLT  480
SLGVPLTVLS QLGGHSRKRT HRAPDKKDGT PLPIGFTIMK TLEDHVRGNL SGRITIMENC  540
SVTSLLSETK ERPDGTKQIR VTGVEFTQAG SGKTTILADA VILATGGFSN DKTADSLLRE  600
HAPHLVNFPT TNGPWATGDG VKLAQRLGAQ LVDMDKVQLH PTGLINPKDP ANPTKFLGPE  660
ALRGSGGVLL NKQGKRFVNE LDLRSVVSKA IMEQGAEYPG SGGSMFAYCV LNAAAQKLFG  720
VSSHEFYWKK MGLFVKADTM RDLAALIGCP VESVQQTLEE YERLSISQRS CPITRKSVYP  780
CVLGTKGPYY VAFVTPSIHY TMGGCLISPS AEIQMKNTSS RAPLSHSNPI LGLFGAGEVT  840
GGVHGGNRLG GNSLLECVVF GRIAGDRAST ILQRKSSALS FKVWTTVVLR EVREGGVYGA  900
GSRVLRFNLP GALQRSGLSL GQFIAIRGDW DGQQLIGYYS PITLPDDLGM IDILARSDKG  960
TLREWISALE PGDAVEMKAC GGLVIERRLS DKHFVFMGHI INKLCLIAGG TGVAPMLQII  1020
KAAFMKPFID TLESVHLIYA AEDVTELTYR EVLEERRRES RGKFKKTFVL NRPPPLWTDG  1080
VGFIDRGILT NHVQPPSDNL LVAICGPPVM QRIVKATLKT LGYNMNLVRT VDETEPSGS   1139

SEQ ID NO: 66          moltype = AA  length = 607
FEATURE                Location/Qualifiers
source                 1..607
                       mol_type = protein
                       organism = Pichia kudriavzevii
SEQUENCE: 66
MSQEKHWNYT KDIVRTSISG VCAANPYLKY IESERVVYNS HSPENGEEKV TVVSGGGSGH  60
EPLHLGFVGD ALLDVAVAGS IFASPSVKQV LSGIHSKPSK KGTVVVVKNY TGDILHFGLA  120
IERARSQGIN AGLLIVQDDV SVGKTKNGKV GRRGLAGTAL VHKLVGAKSF VDGCKASLDD  180
VMDLGQRVID NMVTIGASLD RVVIPTVHGE EKQDDSDDED EKIDELGKDE IEIGMGIHNE  240
HGIKRVSPIP TVDQLAETLL AYLLDPNDKE RYYVDFDKDD DVVLLINNLG STSVLELYAI  300
QAIVNEKLFS IYNIKPVRIY TGTFVTSLDG PGISITLLNV TKAGGDEILR LLDLPTNAPG  360
WNSAIQSSDW KTLGEQLVKE APEIHYATSS IKLDPELVKK ILLKGCEEVK KVEPKVTLYD  420
TVAGDGDCGE TLLAGADSIT NSLRDNSIDL TDAVRFFEEL GDVVESAMGG TSGGLYSIFI  480
SSMSSFLKQQ EKSRGAFTVS EEDFADTLEA GLKGLQRYTR ARVGDRTLMD ALIPFVETFK  540
```

```
STGDINKAAQ AAHDGAESTR KLAAKFGRAS YVAEEEFRRF DSEGGLPDPG AIGLAALING  600
FVSAYQS                                                             607

SEQ ID NO: 67          moltype = AA  length = 469
FEATURE                Location/Qualifiers
source                 1..469
                       mol_type = protein
                       organism = unidentified
SEQUENCE: 67
MSQLDQKVKE IVESFEVEKE LLQNLVTLFI RSAEYGLTHS SVGKAAMPMI PTYVTQIPTG  60
KEKGVLLAAD LGGTNFRVCS VKLNGDHTFE LKQSKNPIPV DLMSSTTEEL FSYLAGKIGQ  120
FVETHHNDIG DKMKLGFTFS FPVEQTSLNS GTLIRWTKGF NIEDTVGKDI VAVLQDHLDR  180
KNIPVHVAAL ANDTVGTLLA RSYTGENKEG LTSIGCIYGT GTNGAYNEKV ENITKLPKEV  240
VEELKSKGID HMVINTEWGS FDNNLELLPT TKYDVEVDKI SANPGYHLFE KRVSGMFLGE  300
ILRHILVDLY EQGLMFTQYP TINELPHRLK TPWLLHSEGL SIFEIDDSTN LIATEIELKN  360
MLRLPTTPEE RKAIQKLTRA ISKRAAHLAG VPIAALTMKI DAFKGHNVEV DVGVDGSVVE  420
FYPGFRTMMR DAIADTQIGA KGERRLHVNL SKDGSSVGAA LCALSNNSL               469

SEQ ID NO: 68          moltype = AA  length = 463
FEATURE                Location/Qualifiers
source                 1..463
                       mol_type = protein
                       organism = unidentified
SEQUENCE: 68
MTQTLQAAFE KTKSELTVTT EKLEEITNHF VEELEKGISP AGGNIPMNPT WVMDYPSGSE  60
TGEYLAIDLG GTNLRVIRVT LQGDSKFKSV NEKYPIPVPM RTGNKDDLFD FIAKSLDDFI  120
KHQYGEDYKG EKLPLGFTFS YPAHQNAINH GVLQTWTKGF DIPGVEGHDV VPMLQASLDK  180
LNTPVEVVAL INDTTGTLVA SKYCDTETIM GLIFGTGCNG AYYDFAKNIP KLEGKLASDI  240
NDETPMAINC EYGAFDNDWK VLPRTKYDIQ IDQESPRPGQ QFYEKMIAGY YLGEVLRLIL  300
LDYYSQGLVF INQDIKSLQV PFAMDTSFPS MIEEHGPEYA GKLFKDTFNI TLTKEEEKVI  360
SDLCQIIGTR AARLSVCSIA GICRKMNYKS GHCAADGSVF NRYPYFKERA AAALNELFKW  420
NTDPKDYPIK LTHAEDGSGV GAAVIACLTE KRLLAGKSVG AKL                     463

SEQ ID NO: 69          moltype = AA  length = 477
FEATURE                Location/Qualifiers
source                 1..477
                       mol_type = protein
                       organism = unidentified
SEQUENCE: 69
MTNSKLDLYT EKLHKDFHVS TVSLHKIIDY FIEELDRGLQ DGTDPLGIPM NVAWVMEYPT  60
GDETGDYLAL DMGGTNLRVV IVHLKGKGQM ETDQAFYKLP DGIRTVKDRN VLFDFMAEKL  120
DQFLKDKHPE GIPENKVFPL GFTFSYPATQ SRINSGVLQR WTKGFDIPGV EGEDVVPLLT  180
EKLKERNVPI KIVALINDTC GTLVASRYVD PLTEMGCIFG TGVNGAYYEK VSNITKYKGR  240
FPKDIPEDSP MLINCEYGSF DNAHKVIPRT RFDITIDETS PRPGQQTFEK MTAGFYLGDL  300
LRLTLLEAYT EGITFEDAPA EFVKCLNTPQ CIDASFLSRI ELDESDDLVT AKKLFADEFK  360
YPNATTDEVK FAKAAAQLIS NRAARLSICG VAAVCKKRGY KKCHIAADGS VYLKYPNFAS  420
RAAEGLADVF GWGHEMPQSE HPIRIVTALD GSGVGAAIIA ALAHKREVAG LSLGLED      477

SEQ ID NO: 70          moltype = DNA  length = 156
FEATURE                Location/Qualifiers
source                 1..156
                       mol_type = unassigned DNA
                       organism = unidentified
SEQUENCE: 70
ctttggtctc ctgcatcagc ataagaacct gcaatggcat tgacggcaga caattcaccg  60
acaccgaatt ctgattaggg atgcaaatcc attgattctt gcataaccat cagcttcgta  120
gcaattcacc gacaccaaag ggtttggaga cctttc                             156

SEQ ID NO: 71          moltype = DNA  length = 156
FEATURE                Location/Qualifiers
source                 1..156
                       mol_type = unassigned DNA
                       organism = unidentified
SEQUENCE: 71
ctttggtctc ctgcaaagac tatccggaac atccgttcaa ggtgacggtt gttggttccg  60
gtaacgaatt cgtacaattg ccaaggttat agcggaaaac accgttgaga gacctcgtca  120
attgttggtt ccggtaactg ggtttggaga cctttc                             156

SEQ ID NO: 72          moltype = DNA  length = 156
FEATURE                Location/Qualifiers
source                 1..156
                       mol_type = unassigned DNA
                       organism = unidentified
SEQUENCE: 72
ctttggtctc ctgcacaaga tttactgagt tgttcccaac aaagcagtcg atggctgcca  60
acaagctcga gtttaagaat gattggtttc aaacaatggc tcttgatttt atctgggttc  120
ccacctttttg aatcctcttc cgtttggaga cctttc                             156

SEQ ID NO: 73          moltype = DNA  length = 156
```

-continued

```
FEATURE                 Location/Qualifiers
source                  1..156
                        mol_type = unassigned DNA
                        organism = unidentified
SEQUENCE: 73
ctttggtctc ctgcaccaga ttcactgagc tattgccaac aaagcaacag atgaaacaaa  60
ataaactcga gcttgagaat gatgggtcgt agacaatggc tgatgtttct gagtgccttc  120
tcatttgttg aatccattgc cgtttggaga cctttc                            156

SEQ ID NO: 74           moltype = DNA  length = 156
FEATURE                 Location/Qualifiers
source                  1..156
                        mol_type = unassigned DNA
                        organism = unidentified
SEQUENCE: 74
ctttggtctc ctgcagtaaa tacctttggc attcctggta ttcctgaata tgcttcttac  60
cttaactcga gtaagacaaa agttattcaa ccaaattgaa gcttctaggt tgttgccaaa  120
gagaagcaaa tgatgctacc ggtttggaga cctttc                            156
```